(12) United States Patent
Gaiger et al.

(10) Patent No.: US 7,063,854 B1
(45) Date of Patent: Jun. 20, 2006

(54) COMPOSITION AND METHODS FOR WT1 SPECIFIC IMMUNOTHERAPY

(75) Inventors: Alexander Gaiger, Seattle, WA (US); Martin A. Cheever, Mercer Island, WA (US)

(73) Assignees: Corixa Corporation, Seattle, WA (US); University of Washington, Seattle, WA (US)

( * ) Notice: Subject to any disclaimer, the term of this patent is extended or adjusted under 35 U.S.C. 154(b) by 0 days.

(21) Appl. No.: 09/164,223

(22) Filed: Sep. 30, 1998

(51) Int. Cl.
*A61K 38/16* (2006.01)
*A61K 38/17* (2006.01)
*C07K 14/435* (2006.01)
*C07K 14/47* (2006.01)

(52) U.S. Cl. .............................. 424/277.1; 424/184.1; 424/185.1; 424/278.1; 514/2; 514/13; 514/12; 514/885; 530/324; 530/325; 530/326

(58) Field of Classification Search ............. 424/184.1, 424/185.1, 277.1, 278.1; 514/2, 13, 12, 885; 530/326, 325, 324
See application file for complete search history.

(56) References Cited

U.S. PATENT DOCUMENTS

| | | | |
|---|---|---|---|
| 5,350,840 A | 9/1994 | Call et al. | .................. 536/23.1 |
| 5,633,142 A | 5/1997 | Herlyn et al. | .............. 435/7.23 |
| 5,670,317 A | 9/1997 | Ladanyi et al. | ................. 435/6 |
| 5,693,522 A | 12/1997 | Chada et al. | ............ 435/2.402 |
| 5,726,288 A * | 3/1998 | Call et al. | .................... 530/350 |
| 6,034,235 A | 3/2000 | Sugiyama et al. | ......... 536/24.5 |
| 6,096,313 A * | 8/2000 | Jager et al. | .............. 424/184.1 |
| 6,277,832 B1 | 8/2001 | Sugiyama et al. | ............ 514/44 |
| 6,316,599 B1 | 11/2001 | Call et al. | ................ 530/387.7 |

FOREIGN PATENT DOCUMENTS

| | | |
|---|---|---|
| EP | 1004319 A1 | 5/2000 |
| EP | 1103564 A1 | 5/2001 |
| JP | 11-89596 A | 4/1999 |
| JP | 11-89599 A | 4/1999 |
| WO | WO 91/07509 | 5/1991 |
| WO | WO 94/21287 | 9/1994 |
| WO | 95/06725 | 3/1995 |
| WO | 95/29995 | 11/1995 |
| WO | WO 96/38176 | 12/1996 |
| WO | WO 99/03506 | 1/1999 |
| WO | 99/58135 | 11/1999 |
| WO | WO 00/06602 | 2/2000 |
| WO | WO 00/18795 | 4/2000 |
| WO | WO 01/60970 | 8/2001 |
| WO | WO 01/94629 | 12/2001 |
| WO | WO 02/00677 | 1/2002 |

OTHER PUBLICATIONS

Boon, Int. J Cawlyn, 54:177-180, 1993.*
Menke et al., "Wilms' Tumor 1 splice variants have opposite effects on the tumorigenicity of adenovirus-transformed baby-rat kidney cells," *Oncogene 12*: 537-546, 1996.

Yamagami et al., "Growth Inhibition of Human Leukemic Cells by WT1 (Wilms Tumor Gene) Antisense Oligodeoxynucleotides: Implications for the Involvement of WT1 in Leukemogenesis," *Blood 87*(7): 2878-2884, 1996.
Mundlos et al., "Nuclear localization of the protein encoded by the Wilms' tumor gene WT1 in embryonic and adult tissues," *Development 119*: 1329-1341, 1993.
Kudoh et al., "$G_1$ phase arrest induced by Wilms tumor protein WT1 is abrogated by cyclin/CDK complexes," *Proc. Natl. Acad. Sci. USA 92*: 4517-4521, 1995.
Ramani and Cowell, "The Expression Pattern Of Wilms' Tumour Gene (WT1) Product In Normal Tissues And Paediatric Renal Tumours," *Journal Of Pathology 179*: 162-168, 1996.
Menssen et al., "Wilms' Tumor Gene Expression in Human CD34 Hematopoietic Progenitors During Fetal Development and Early Clonogenic Growth," *Blood 89* (9): 3486-3487, 1997 (letter).
Call et al., "Isolation and Characterization of a Zinc Finger Polypeptide Gene at the Human Chromosome 11 Wilms' Tumor Locus," *Cell 60*: 509-520, 1990.
Telerman et al., "Identification of the cellular protein encoded by the human Wilms' tumor (WT1) gene," *Oncogene 7*:2545-2548, 1992.
Sharma et al., "Molecular Cloning of Rat Wilms' Tumor Complementary DNA and a Study of Messenger RNA Expression in the Urogenital System and the Brain," *Cancer Research 52*: 6407-6412, 1992.
Wang et al., "The Wilms' Tumor Gene Product, WT1, Represses Transcription of the Platelet-derived Growth Factor A-chain Gene," *The Journal Of Biological Chemistry 267*(31): 21999-22002, 1992.
Tadokoro et al., "Genomic Organization of the Human WT1 Gene," *Jpn. J. Cancer Res. 83*: 1198-1203, 1992.
Haber et al., "A dominant mutation in the Wilms tumor gene WT1 cooperates with the viral oncogene E1A in transformation of primary kidney cells," *Proc. Natl. Acad. Sci. USA 89*:6010-6014, 1992.
Inoue et al., "WT1 as a New Prognostic Factor and a New Marker for the Detection of Minimal Residual Disease in Acute Leukemia," *Blood 84*:3071-3079, 1994.
Tsurutani et al., "cDNA cloning and developmental expression of the porcine homologue of WT1," *Gene 211*(2): 215-220, 1998.

(Continued)

*Primary Examiner*—Ronald B. Schwadron
(74) *Attorney, Agent, or Firm*—Seed IP Law Group PLLC

(57) ABSTRACT

Compositions and methods for the therapy of malignant diseases, such as leukemia and cancer, are disclosed. The compositions comprise one or more of a WT1 polynucleotide, a WT1 polypeptide, an antigen-presenting cell presenting a WT1 polypeptide, an antibody that specifically binds to a WT1 polypeptide; or a T cell that specifically reacts with a WT1 polypeptide. Such compositions may be used, for example, for the prevention and treatment of metastatic diseases.

2 Claims, 12 Drawing Sheets

OTHER PUBLICATIONS

Huang et al., "Tissue, Developmental, and Tumor-Specific Expression of Divergent Transcripts in Wilms Tumor," *Science 250*: 991-994, 1990.

Phelan et al., "Wilms' Tumor Gene, WT1, mRNA Is Down-regulated during Induction of Erythroid and Megakaryocytic Differentiation of K562 Cells," Cell Growth & Differentiation 5: 677-686, 1994.

Sekiya et al., "Downregulation of Wilms' Tumor Gene (wt1) During Myelomonocytic Differentiation in HL60 Cells," *Blood 83*(7): 1876-1882, 1994.

Brieger et al., "The Expression of the Wilms' Tumor Gene in Acute Myelocytic Luekemias as Possible Marker for Leukemia Blast Cells," *Leukemia 8*(12): 2138-2143, 1994.

Pritchard-Jones et al., "The Wilms tumour (WT1) gene is mutated in a secondary leukaemia in a WAGR patient," *Human Molecular Genetics 3*(9): 1633-1637, 1994.

Tadokoro et al., "Intragenic homozygous delection of the WT1 gene in Wilms' tumor," *Oncogene 7*: 1215-1221, 1992.

Armstrong et al., "The expression of the Wilms' tumour gene, WT1, in the developing mammalian embryo," *Mechanisms of Development 40*: 85-97, 1992.

Wang et al., "The Wilms' Tumor Gene Product WT1 Activates or Suppresses Transcription through Separate Functional Domains," *The Journal Of Biological Chemistry 268*(13): 9172-9175, 1993.

Wang et al., "A second transcriptionally active DNA-binding site for the Wilms tumor gene product, WT1," *Proc. Natl. Acad. Sci. USA 90*: 8896-8900, 1993.

Rauscher, "The WT1 Wilms tumor gene product: a developmentally regulated transcription factor in the kidney that functions as a tumor suppressor," *FASEB J. 7*: 896-903, 1993.

Harrington et al., "Inhibition of Colony-stimulating Factor-1 Promoter Activity by the Product of the Wilms' Tumor Locus," *The Journal Of Biological Chemistry 268*(28): 21271-21275, 1993.

Tadokoro et al., "PCR Detection of 9 Polymorphisms in the WT1 Gene," *Human Molecular Genetics 2*(12): 2205-2206, 1993.

Tadokoro et al., "Taq1 RFLPs at the Wilms' tumor gene (WT1)," *Nucleic Acids Research 19*(9): 2514, 1991.

Kreidberg et al., "WT-1 Is Required for Early Kidney Development," *Cell 74*: 679-691, 1993.

Miyagi et al., "Expression of the Candidate Wilms' Tumor Gene, WT1, in Human Leukemia Cells," *Leukemia 7*(7): 970-977, 1993.

Brenner et al., "RNA polymerase chain reaction detects different levels of four alternatively spliced WT1 transcripts in Wilms' tumors," *Oncogene 7*: 1431-1433, 1992.

Rupprecht et al., "The Wilms' Tumor Suppressor Gene WT1 Is Negatively Autoregulated," *The Journal Of Biological Chemistry 269*(8): 6198-6206, 1994.

Wang et al., "WT1, the Wilms' tumor suppressor gene product, represses transcription through an interactive nuclear protein," *Oncogene 10*(6): 1243-1247, 1995.

Wu et al., "GATA-1 Transactivates the WT1 Hematopoietic Specific Enhancer," *The Journal Of Biological Chemistry 270*(11): 5944-5949, 1995.

Brieger et al., "The Wilms' tumor gene is frequently expressed in acute myeloblastic leukemias and may provide a marker for residual blast cells detectable by PCR," *Annals of Oncology 6*: 811-816, 1995.

Hamilton et al., "High affinity binding sites for the Wilms' tumour suppressor protein WT1," *Nucleic Acids Research 23*(2): 277-284, 1995.

Reddy et al., "WT1-mediated Transcriptional Activation Is Inhibited by Dominant Negative Mutant Proteins," *The Journal Of Biological Chemistry 270*(18): 10878-10884, 1995.

Nichols et al., "WT1 Induces Expression of Insulin-like Growth Factor 2 in Wilms' Tumor Cells," *Cancer Research 55*: 4540-4543, 1995.

Luo et al., "The tumor suppressor gene WT1 inhibits ras-mediated transformation," *Oncogene 11*: 743-750, 1995.

Goodyer et al., "Repression of the retinoic acid receptor-α gene by the Wilms' tumor suppressor gene product, wt1," *Oncogene 10*: 1125-1129, 1995.

King-Underwood et al., "Mutations in the Wilms' Tumor Gene WT1 in Leukemias," *Blood 91*: 2961-2968, 1998.

Patmasiriwat et al., "Expression pattern of WT1 and GATA-1 in AML with chromosome 16q22 abnormalities," *Leukemia 10*: 1127-1133, 1996.

Inoue et al., "Long-Term Follow-Up of Minimal Residual Disease in Leukemia Patients by Monitoring WT1 (Wilms Tumor Gene) Expression Levels," *Blood 88*:2267-2278, 1996.

Frazier et al., "Expression of the Tumor Suppressor Gene WT1 in Both Human and Mouse Bone Marrow," *Blood 86*: 4704-4706, 1995 (letter).

Algar et al., "A WT1 antisense oligonucleotide inhibits proliferation and induces apoptosis in myeloid leukaemia cell lines," *Oncogene 12*: 1005-1014, 1996.

Ye et al., "Regulation of WT1 by phosphorylation: inihibition of DNA binding, alteration of transcriptional activity and cellular translocation," *The EMBO Journal 15*(20): 5606-5615, 1996.

Adachi et al., "Midkine as a novel target gene for the Wilms' tumor suppressor gene (WT1)," *Oncogene 13*: 2197-2203, 1996.

Kudoh et al., "Constitutive expression of the Wilms tumor suppressor gene WT1 in F9 embryonal carcinoma cells induces apoptotic cell death in response to retinoic acid," *Oncogene 13*: 1431-1439, 1996.

Svedberg et al., "Constitutive expression of the Wilms' tumor gene (WT1) in the leukemic cell line U937 blocks parts of the differentiation program," *Oncogene 15*: 1-8, 1997.

Bergmann et al., "High Levels of Wilms' Tumor Gene (wt1) mRNA in Acute Myeloid Leukemias Are Associated With a Worse Long-Term Outcome," *Blood 90*(3): 1217-1225, 1997.

Inoue et al., "Aberrant Overexpression of the Wilms Tumor Gene (WT1) in Human Leukemia," *Blood 89*(4): 1405-1412, 1997.

Menssen et al., "Detection By Monoclonal Antibodies Of The Wilms' Tumor (WT1) Nuclear Protein In Patients With Acute Leukemia," *Int. J. Cancer 70*: 518-523, 1997.

Schmid et al., "Prognostic significance of WT1 gene expression at diagnosis in adult de novo acute myeloid leukemia," *Leukemia 11*: 639-643, 1997.

Drummond et al., "Repression of the Insulin-Like Growth Factor Gene by the Wilms Tumor Suppressor WT1," *Science 257*: 674-677, 1992.

Harrington et al., "Inhibition of Colony-stimulating Factor-1 Promoter Activity by the Product of the Wilms' Tumor Locus," *The Journal Of Biological Chemistry 268*(28): 21271-21275, 1993.

Werner et al., "Inhibition of Cellular Proliferation by the Wilms' Tumor Suppressor WT1 Is Associated with Suppression of Insulin-Like Growth Factor I Receptor Gene Expression," *Molecular and Cellular Biology 15*: 3516-3522, 1995.

Haber et al., "An Internal Deletion with an 11p13 Zinc Finger Gene Contributes to the Development of Wilms' Tumor," *Cell 61*: 1257-1269, 1990.

Haber et al., "Alternative splicing and genomic structure of the Wilms tumor gene WT1," *Proc. Natl. Acad. Sci. USA 88*: 9618-9622, 1991.

Madden et al., "Transcriptional Repression Mediated by the WT1 Wilms Tumor Gene Product," *Science 253*: 1550-1552, 1991.

Rauscher et al., "Binding of the Wilms' Tumor Locus Zinc Finger Protein to the EGR-1 Consensus Sequence," *Science 250*: 1259-1262, 1990.

Nakagama et al., "Sequence and Structural Requirements for High-Affinity DNA Binding by the WT1 Gene Product," *Molecular and Cellular Biology 15*(3): 1489-1498, 1995.

Pritchard-Jones et al., "The candidate Wilms' tumour gene is involved in genitourinary development," *Nature 346*: 194-197, 1990.

Morris et al., "Characterization of the zinc finger protein encoded by the WT1 Wilms' tumor locus," *Oncogene 6*: 2339-2348, 1991.

Pelletier et al., "Germline Mutations in the Wilms' Tumor Suppressor Gene Are Associated with Abnormal Urogenital Development in Denys-Drash Syndrome," *Cell 67*: 437-447, 1991.

Buckler et al., "Isolation, Characterization, and Expression of the Murine Wilms' Tumor Gene (WT1) During Kidney Development," *Molecular and Cellular Biology 11*: 1707-1712, 1991.

Pelletier et al., "Expression of the Wilms' tumor gene WT1 in the murine urogenital system," *Genes & Development 5*: 1345-1356, 1991.

Miwa et al., "Expression of the Wilms' Tumor Gene (WT1) in Human Leukemias," *Leukemia 6*(5): 405-409, 1992.

Ogawa et al., "Successful donor leukocyte transfusion at molecular relapse for a patient with acute myeloid leukemia who was treated with allogeneic bone marrow transplantation: importance of the monitoring of minimal residual disease by WT1 assay," *Bone Marrow Transplantation 21*: 525-527, 1998.

Inoue et al., "Wilms' Tumor Gene (WT1) Competes With Differentiation-Inducing Signal in Hematopoetic Progenitor Cells," *Blood 91*(8): 2969-2976, 1998.

King-Underwood and Pritchard-Jones, "Wilms' Tumor (WT1) Gene Mutations Occur Mainly in Acute Myeloid Leukemia and May Confer Drug Resistance," *Blood 91*(8): 2961-2968, 1998.

Maurer et al., "The Wilms' tumor gene is expressed in a subset of CD34 progenitors and downregulated early in the course of differentiation in vitro," *Experimental Hematology 25*: 945-950, 1997.

Charles et al., "Expression of the Wilms' tumour gene WT1 in the developing human and in paediatric renal tumours: an immunohistochemical study," *J. Clin. Pathol.: Mol. Pathol. 50*: 138-144, 1997.

Silberstein et al., "Altered expression of the WT1 Wilms tumor suppressor gene in human breast cancer," *Proc. Natl. Acad. Sci. USA 94*: 8132-8137, 1997.

Charles et al., "Immunohistochemical detection of the Wilms' tumour gene WT1 in desmoplastic small round cell tumour," *Histopathology 30*: 312-314, 1997.

Carapeti et al., "Dominant-negative mutations of the Wilms' tumour predisposing gene (WT1) are infrequent in CML blast crisis and de novo acute leukaemia," *Eur. J. Haematol. 58*: 346-349, 1997.

Murata et al., "The Wilms tumor suppressor gene WT1 induces G1 arrest and apoptosis in myeloblastic leukemia M1 cells," *FEBS Letters 409*: 41-45, 1997.

Bergmann et al., "Wilms Tumor Gene Expression in Acute Myeloid Leukemias," *Leukemia and Lymphoma 25*: 435-443, 1997.

Osaka et al., "WT1 Contributes To Leukemogenesis: Expression Patterns In 7,12-Dimethylbenz[a]Anthracene (DMBA)-Induced Leukemia," *International Journal of Cancer 72*: 696-699, 1997.

Parker et al., "Scheme for Ranking Potential HLA-A2 Binding Peptides Based on Independent Binding of Individual Peptide Side-Chains," *Journal of Immunology 152*: 163-175, 1994.

Feller and de la Cruz, "Tsites (Version 1.1) A computer program to determine T cell epitopes using four predictive algorithms," *Nature 349*: 720-721, 1991.

Pogue et al., "Amino-terminal alteration of the HLA-A*0201-restricted human immunodeficiency virus pol peptide increases complex stability and in vitro immunogenicity," *Proc. Natl. Acad. Sci. USA 92*: 8166-8170, 1995.

Bellantuono et al., "Selective elmination of leukemic progenitors by allorestricted CTL specific for WILMS Tumor Antigen-1 (WT-1)," *Blood,* 94(10):532A-533A, Nov. 15, 1999.

Deavin et al., "Statistical comparison of established T-cell eptiope predictors against a large database of human and murine antigens," *Molecular Immunology,* 33(2):145-155, 1996.

Gaiger et al., "WT1: A new leukemia and cancer antigen A," *Proceedings of the Annual Meeting of the American Association for Cancer Research,* 40:424, 1999.

Gaiger et al., "Immunity to WT1 in animal models and leukemia patients," *Blood,* 94(10):78, Nov. 15, 1999.

Rauscher et al., "Characterization of monoclonal antibodies directed to the amino-terminus of the WT1, Wilms' tumor suppressor," *Hybridoma,* 17(2):191-198, Apr. 1998.

Rothbard and Taylor, "A sequence pattern common to T cell epitopes," *EMBO Journal,* 7(1):93-100, 1988.

Sadovnikova et al., "Generation of human tumor-reative cytotoxic T-cells against peptides presented by non-self HLA class I molecules," *Eur.J. Immunol.,* 28:193-200, 1998.

Toes et al., "Efficient tumor eradication by adoptively transferred cytotoxic T-cell clones in allogeneic hosts," *Int. J. Cancer,* 66:686-691, 1996.

Rackley et al., "Expression of the Wilms' Tumor Suppressor Gene WT1 during Mouse Embryogenesis," *Cell Growth & Differentiation 4*: 1023-1031, 1993.

Menssen et al., "Presence of Wilms' tumor gene (wt1) transcripts and the WT1 nuclear protein in the majority of human acute leukemias," *Leukemia 9*: 1060-1067, 1995.

Larsson et al., "Subnuclear Localization of WT1 in Splicing or Transcription Factor Domains Is Regulated by Alternative Splicing," *Cell 81*: 391-401, 1995.

Oka, Y. et al., "Wilms Tumor Gene Peptide-Based Immunotherapy for Patients with Overt Leukemia from Myelodysplastic Syndrome (MDS) or MDS with Myelofibrosis," *International Journal of Hematology* 78: 56-61, 2003.
GenBank Database, Accession No. A39692, Feb. 16, 1997.
GenBank Database, Accession No. AAA36810, Jun. 15, 1990.
GenBank Database, Accession No. AAA62825, Oct. 27, 1994.
GenBank Database, Accession No. AAB33427, May 12, 1995.
GenBank Database, Accession No. AAB33443, Jul. 11, 1995.
GenBank Database, Accession No. AAC60039, Nov. 8, 1996.
GenBank Database, Accession No. BAA94794, Apr. 21, 2000.
GenBank Database, Accession No. CAA35956, May 29, 1991.
GenBank Database, Accession No. CAA43819, Dec. 3, 1993.
GenBank Database, Accession No. CAA59736, Feb. 13, 1996.
GenBank Database, Accession No. 151960, Nov. 5, 1999.
GenBank Database, Accession No. M30393, Jun. 15, 1990.
GenBank Database, Accession No. NM_000378, Nov. 5, 2000.
GenBank Database, Accession No. NM_024424, Mar. 20, 2001.
GenBank Database, Accession No. NM_024426, Mar. 20, 2001.
GenBank Database, Accession No. NP_000369, Nov. 5, 2000.
GenBank Database, Accession No. NP_077742, Mar. 20, 2001.
GenBank Database, Accession No. NP_077743, Mar. 20, 2001.
GenBank Database, Accession No. NP_077744, Mar. 20, 2001.
GenBank Database, Accession No. NP_113722, Apr. 6, 2003.
GenBank Database, Accession No. O62651, Nov. 1, 1998.
GenBank Database, Accession No. P50902, Oct. 1, 1996.
GenBank Database, Accession No. S75264, Jul. 11, 1995.
GenBank Database, Accession No. X51630, May 29, 1991.
Geneseq Database, Accession No. AAT45130, Aug. 19, 1997.
Geneseq Database, Accession No. AAT45131, Aug. 20, 1997.
Geneseq Database, Accession No. AAT45132, Aug. 20, 1997.
Geneseq Database, Accession No. AAT45133, Aug. 20, 1997.
Geneseq Database, Accession No. AAT45134, Aug. 20, 1997.
Geneseq Database, Accession No. AAT45135, Aug. 20, 1997.
Geneseq Database, Accession No. AAT45136, Aug. 20, 1997.
Geneseq Database, Accession No. AAT45137, Aug. 20, 1997.
Geneseq Database, Accession No. AAT45138, Aug. 20, 1997.
Geneseq Database, Accession No. AAT45139, Aug. 20, 1997.
Geneseq Database, Accession No. AAT45140, Aug. 20, 1997.
Geneseq Database, Accession No. AAT45141, Aug. 20, 1997.
Geneseq Database, Accession No. AAT45142, Aug. 20, 1997.
Geneseq Database, Accession No. AAT97855, Mar. 9, 1998.
Geneseq Database, Accession No. AAT97856, Mar. 9, 1998.
Geneseq Database, Accession No. AAT97857, Mar. 9, 1998.
Geneseq Database, Accession No. AAT97858, Mar. 9, 1998.
Geneseq Database, Accession No. AAT97859, Mar. 9, 1998.
Geneseq Database, Accession No. AAT97860, Mar. 9, 1998.
Geneseq Database, Accession No. AAT97861, Mar. 9, 1998.
Geneseq Database, Accession No. AAT97862, Mar. 9, 1998.
Geneseq Database, Accession No. AAT97863, Mar. 9, 1998.
Geneseq Database, Accession No. AAT97864, Mar. 9, 1998.
Geneseq Database, Accession No. AAT97865, Mar. 9, 1998.
Geneseq Database, Accession No. AAT97866, Mar. 9, 1998.
Geneseq Database, Accession No. AAT97867, Mar. 9, 1998.
Geneseq Database, Accession No. AAT97868, Mar. 9, 1998.
Geneseq Database, Accession No. AAX15839, May 11, 1999.
Geneseq Database, Accession No. AAX15840, May 11, 1999.
Geneseq Database, Accession No. AAX15841, May 11, 1999.
Geneseq Database, Accession No. AAX15842, May 11, 1999.
Geneseq Database, Accession No. AAX15843, May 11, 1999.
Geneseq Database, Accession No. AAX15844, May 11, 1999.
Geneseq Database, Accession No. AAX15845, May 11, 1999.
Geneseq Database, Accession No. AAX15846, May 11, 1999.
Geneseq Database, Accession No. AAX15847, May 11, 1999.
Geneseq Database, Accession No. AAX15848, May 11, 1999.
Geneseq Database, Accession No. AAX15849, May 11, 1999.
Geneseq Database, Accession No. AAX15850, May 11, 1999.
Geneseq Database, Accession No. AAX15851, May 11, 1999.
Geneseq Database, Accession No. AAX15852, May 11, 1999.
Geneseq Database, Accession No. AAX15853, May 11, 1999.
Geneseq Database, Accession No. AAX15854, May 11, 1999.
Geneseq Database, Accession No. AAX15855, May 11, 1999.
Geneseq Database, Accession No. AAX23927, Jun. 25, 1999.
Geneseq Database, Accession No. AAX23928, Jun. 25, 1999.
Geneseq Database, Accession No. AAX23929, Jun. 25, 1999.
Geneseq Database, Accession No. AAX23930, Jun. 25, 1999.
Geneseq Database, Accession No. AAX23931, Jun. 25, 1999.
Geneseq Database, Accession No. AAX34315, Jul. 6, 1999.
Geneseq Database, Accession No. AAX34316, Jul. 6, 1999.

Geneseq Database, Accession No. AAX34317, Jul. 6, 1999.
Geneseq Database, Accession No. AAX34318, Jul. 6, 1999.
Geneseq Database, Accession No. AAX34319, Jul. 6, 1999.
Geneseq Database, Accession No. AAX34320, Jul. 6, 1999.
Geneseq Database, Accession No. AAX34321, Jul. 6, 1999.
Geneseq Database, Accession No. AAY80196, May 24, 2000.
Geneseq Database, Accession No. AAY80197, May 24, 2000.
Geneseq Database, Accession No. AAY80198, May 24, 2000.
Genseq Database, Accession No. AAY80199, May 24, 2000.
Genseq Database, Accession No. AAY80200, May 24, 2000.
Genseq Database, Accession No. AAY80201, May 24, 2000.
Genseq Database, Accession No. AAY80202, May 24, 2000.
Genseq Database, Accession No. AAY80203, May 24, 2000.
Genseq Database, Accession No. ABP42234, Aug. 22, 2002.

* cited by examiner

HU: MGSDVRDLNALLPAVPSLGGGGGCALPVSGAAQWAPVLDFAPPGASAYGSL
MO: MGSDVRDLNALLPAVSSLGGGGGCGLPVSGAAQWAPVLDFAPPGASAYGSL

HU: GGPAPPPAPPPPPPPPPHSFIKQEPSWGGAEPHEEQCLSAFTVHFSGQFTGTAG
MO: GGPAPPPAPPPPPPPPPHSFIKQEPSWGGAEPHEEQCLSAFTLHFSGQFTGTAG

HU: ACRYGPFGPPPPSQASSGQARMFPNAPYLPSCLESQPAIRNQGYSTVTFDGTPS
MO: ACRYGPFGPPPPSQASSGQARMFPNAPYLPSCLESQPTIRNQGYSTVTFDGAPS

HU: YGHTPSHHAAQFPNHSFKHEDPMGQQGSLGEQQYSVPPPVYGCHTPTDSCTG
MO: YGHTPSHHAAQFPNHSFKHEDPMGQQGSLGEQQYSVPPPVYGCHTPTDSCTG

HU: SQALLLRTPYSSDNLYQMTSQLECMTWNQMNLGATLKGVAAGSSSSVKWTE
MO: SQALLLRTPYSSDNLYQMTSQLECMTWNQMNLGATLKGMAAGSSSSVKWTE

HU: GQSNHSTGYESDNHTTPILCGAQYRIHTHGVFRGIQDVRRVPGVAPTLVRSAS
MO: GQSNHGIGYESDNHTAPILCGAQYRIHTHGVFRGIQDVRRVSGVAPTLVRSAS

HU: ETSEKRPFMCAYPGCNKRYFKLSHLQMHSRKHTGEKPYQCDFKDCERRFSR
MO: ETSEKRPFMCAYPGCNKRYFKLSHLQMHSRKHTGEKPYQCDFKDCERRFSR

HU: SDQLKRHQRRHTGVKPFQCKTCQRKFSRSDHLKTHTRTHTGKTSEKPFSCR
MO: SDQLKRHQRRHTGVKPFQCKTCQRKFSRSDHLKTHTRTHTGKTSEKPFSCR

HU: WPSCQKKFARSDELVRHHNMHQRNMTKLQLAL
MO: WHSCQKKFARSDELVRHHNMHQRNMTKLHVAL

*Fig. 1*

```
       5   10  15  20  25  30  35  40  45  50  55  60  65  70  75
    MGSDVRDLNALLPAVPSLGGGGGCALPVSGAAQWAPVLDFAPPGASAYGSLGGPAPPPAPPPPPPPPHSFIKQE
    .....AAAAAAAAAAAAAAAAAA.......AAAAAA.........AAAAAAAAAAAA..................
    ..............................RRRR.........................................
    ............................................................................
    ............................................................................
    ............................................................................

80   85   90   95  100  105  110  115  120  125  130  135  140  145  150
    PSWGGAEPHEEQCLSAFTVHFSGQFTGTAGACRYGPFGPPPPSQASSGQARMFPNAPYLPSCLESQPAIRNQGYS
    ................AAA.....AAAA.....................AAA......AAAAAA..........
    .............................RRRR....................RRRRR...............
    ..............................................DDDDDDDDD...................
    ............................................................................

155  160  165  170  175  180  185  190  195  200  205  210  215  220  225
    TVTFDGTPSYGHTPSHHAAQFPNHSFKHEDPMGQQGSLGEQQYSVPPPVYGCHTPTDSCTGSQALLLRTPYSSDN
    .................AAAAA...................AAAAAA...............AA
    ..............RRRR..........................................................
    ..........................................................DDDDDDDDDDDDDD...
    ............................................................................

230  235  240  245  250  255  260  265  270  275  280  285  290  295  300
    LYQMTSQLECMTWNQMNLGATLKGVAAGSSSSVKWTEGQSNHSTGYESDNHTTPILCGAQYRIHTHGVFRGIQDV
    AAAAAAAA...........AAA.AAA..................................AAAAAAAAAAA
    ..............RRRRRRRRRR.....RRRR..............................RRRR.....
    DDDDDD...............DDDDDDDDDD............................................
    ..................................................................ddddd........

305  310  315  320  325  330  335  340  345  350  355  360  365  370  375
    RRVPGVAPTLVRSASETSEKRPFMCAYPGCNKRYFKLSHLQMHSRKHTGEKPYQCDFKDCERRFSRSDQLKRHQR
    AAAAA..AAAAAAAAAAA............................................AAAA.AAAAAAAAA.
    ....RRRRR.......................RRRR.......................................
    .......DDDDDD...............................................................
    ............................................................................

380  385  390  395  400  405  410  415  420  425  430  435  440  445  450
    RHTGVKPFQCKTCQRKFSRSDHLKTHTRTHTGKTSEKPFSCRWPSCQKKFARSDELVRHHNMHQRNMTKLQLAL
    ...........AAAA.AAAA..AA.....AAAA..........AAA....AAAAAAAA...AAA........
    ..............................................................RRRR..RRRR.................
    ............................................................................
    ..............ddddddddddddd.................................................
```

*Fig. 8A*

```
              5   10   15   20   25   30   35   40   45   50   55   60   65   70   75
         MGSDVRDLNALLPAVSSLGGGGCGLPVSGAAQWAPVLDFAPPGASAYGSLGGPAPPPAPPPPPPPPHSFIKQE
         .....AAAAAAAAAAAAAAAAAA.......AAAAAA.........AAAAAAAAAAAA....................
         ................................RRRR........................................
         ..............................................................................
         ..............................................................................

80   85   90   95  100  105  110  115  120  125  130  135  140  145  150
         PSWGGAEPHEEQCLSAFTLHFSGQFTGTAGACRYGPFGPPPPSQASSGQARMFPNAPYLPSCLESQPTIRNQGYS
         ...................AAAA....................AAA......AAAAAA...........
         ..................RRRR.....................RRRRR....................
         ..............................DDDDDDDD..............................
         ......................................................................

155  160  165  170  175  180  185  190  195  200  205  210  215  220  225
         TVTFDGAPSYGHTPSHHAAQFPNHSFKHEDPMGQQGSLGEQQYSVPPPVYGCHTPTDSCTGSQALLLRTPYSSDN
         ...............AAAAA........................AAAAAA...............AA
         ..............RRRR...................................................
         ..................................................DDDDDDDDDDDDDD...
         ......................................................................

230  235  240  245  250  255  260  265  270  275  280  285  290  295  300
         LYQMTSQLECMTWNQMNLGATLKGMAAGSSSSVKWTEGQSNHGIGYESDNHTAPILCGAQYRIHTHGVFRGIQDV
         AAAAAAAA............AAA.AAA.................................AAAAAAAAAAA
         ...................RRRRRRRRRR.....RRRR........................RRRR.....
         DDDDDD............DDDDDDDDDD.............................................
         ......................................................................ddddd.........

305  310  315  320  325  330  335  340  345  350  355  360  365  370  375
         RRVSGVAPTLVRSASETSEKRPFMCAYPGCNKRYFKLSHLQMHSRKHTGEKPYQCDFKDCERRFSRSDQLKRHQR
         AAAAA..AAAAAAAAAA..........................................AAAA.AAAAAAAAAA.
         ....RRRRR.....................RRRR..........................................
         ..DDDDDDDDDD.................................................................
         ......................................................................

380  385  390  395  400  405  410  415  420  425  430  435  440  445  450
         RHTGVKPFQCKTCQRKFSRSDHLKTHTRTHTGKTSEKPFSCRWHSCQKKFARSDELVRHHNMHQRNMTKLHVAL
         .............AAAA.AAAA..AA.....AAAA..........AA...AAAAAAAA...AAAA......
         ................................................RRRR..RRRR.................
         ......................................................................
         ..............dddddddddddd...........................................
```

*Fig. 8B*

COMPOSITION AND METHODS FOR WT1 SPECIFIC IMMUNOTHERAPY

STATEMENT REGARDING FEDERALLY SPONSORED RESEARCH OR DEVELOPMENT

This invention was made with U.S. Government support. The Government may have certain rights in this invention.

TECHNICAL FIELD

The present invention relates generally to the immunotherapy of malignant diseases such as leukemia and cancers. The invention is more specifically related to compositions for generating or enhancing an immune response to WT1, and to the use of such compositions for preventing and/or treating malignant diseases.

BACKGROUND OF THE INVENTION

Cancer and leukemia are significant health problems in the United States and throughout the world. Although advances have been made in detection and treatment of such diseases, no vaccine or other universally successful method for prevention or treatment of cancer and leukemia is currently available. Management of the diseases currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and the high mortality continues to be observed in many cancer patients.

Immunotherapies have the potential to substantially improve cancer and leukemia treatment and survival. Recent data demonstrate that leukemia can be cured by immunotherapy in the context of bone marrow transplantation (e.g., donor lymphocyte infusions). Such therapies may involve the generation or enhancement of an immune response to a tumor-associated antigen (TAA). However, to date, relatively few TAAs are known and the generation of an immune response against such antigens has, with rare exceptions, not been shown to be therapeutically beneficial.

Accordingly, there is a need in the art for improved methods for leukemia and cancer prevention and therapy. The present invention fulfills these needs and further provides other related advantages.

SUMMARY OF THE INVENTION

Briefly stated, this invention provides compositions and methods for the diagnosis and therapy of diseases such as leukemia and cancer. In one aspect, the present invention provides polypeptides comprising an immunogenic portion of a native WT1, or a variant thereof that differs in one or more substitutions, deletions, additions and/or insertions such that the ability of the variant to react with antigen-specific antisera and/or T-cell lines or clones is not substantially diminished. Within certain embodiments, the polypeptide comprises no more than 16 consecutive amino acid residues of a native WT1 polypeptide. Within other embodiments, the polypeptide comprises an immunogenic portion of amino acid residues 1–174 of a native WT1 polypeptide or a variant thereof, wherein the polypeptide comprises no more than 16 consecutive amino acid residues present within amino acids 175 to 345 of the native WT1 polypeptide. The immunogenic portion preferably binds to an MHC class I and/or class II molecule. Within certain embodiments, the polypeptide comprises a sequence selected from the group consisting of (a) sequences recited in any one or more of Tables II–XLVI, (b) variants of the foregoing sequences that differ in one or more substitutions, deletions, additions and/or insertions such that the ability of the variant to react with antigen-specific antisera and/or T-cell lines or clones is not substantially diminished and (c) mimetics of the polypeptides recited above, such that the ability of the mimetic to react with antigen-specific antisera and/or T cell lines or clones is not substantially diminished.

Within other embodiments, the polypeptide comprises a sequence selected from the group consisting of (a) ALL-PAVPSL (SEQ ID NO:34), GATLKGVAA (SEQ ID NO:88), CMTWNQMNL (SEQ ID NOs: 49 and 258), SCLESQPTI (SEQ ID NOs: 199 and 296), SCLESQPAI (SEQ ID NO:198), NLYQMTSQL (SEQ ID NOs: 147 and 284), ALLPAVSSL (SEQ ID NOs: 35 and 255), RMFP-NAPYL (SEQ ID NOs: 185 and 293), (b) variants of the foregoing sequences that differ in one or more substitutions, deletions, additions and/or insertions such that the ability of the variant to react with antigen-specific antisera and/or T-cell lines or clones is not substantially diminished and (c) mimetics of the polypeptides recited above, such that the ability of the mimetic to react with antigen-specific antisera and/or T cell lines or clones is not substantially diminished. Mimetics may comprises amino acids in combination with one or more amino acid mimetics or may be entirely nonpeptide mimetics.

Within further aspects, the present invention provides polypeptides comprising a variant of an immunogenic portion of a WT1 protein, wherein the variant differs from the immunogenic portion due to substitutions at between 1 and 3 amino acid positions within the immunogenic portion such that the ability of the variant to react with antigen-specific antisera and/or T-cell lines or clones is enhanced relative to a native WT1 protein.

The present invention further provides WT1 polynucleotides that encode a WT1 polypeptide as described above.

Within other aspects, the present invention provides pharmaceutical compositions and vaccines. Pharmaceutical compositions may comprise a polypeptide or mimetic as described above and/or one or more of (i) a WT1 polynucleotide; (ii) an antibody or antigen-binding fragment thereof that specifically binds to a WT1 polypeptide; (iii) a T cell that specifically reacts with a WT1 polypeptide or (iv) an antigen-presenting cell that expresses a WT1 polypeptide, in combination with a pharmaceutically acceptable carrier or excipient. Vaccines comprise a polypeptide as described above and/or one or more of (i) a WT1 polynucleotide, (ii) an antigen-presenting cell that expresses a WT1 polypeptide or (iii) an anti-idiotypic antibody, and a non-specific immune response enhancer. Within certain embodiments, less than 23 consecutive amino acid residues, preferably less than 17 amino acid residues, of a native WT1 polypeptide are present within a WT1 polypeptide employed within such pharmaceutical compositions and vaccines. The immune response enhancer may be an adjuvant. Preferably, an immune response enhancer enhances a T cell response.

The present invention further provides methods for enhancing or inducing an immune response in a patient, comprising administering to a patient a pharmaceutical composition or vaccine as described above. In certain embodiments, the patient is a human.

The present invention further provides methods for inhibiting the development of a malignant disease in a patient, comprising administering to a patient a pharmaceutical composition or vaccine as described above. Malignant diseases include, but are not limited to leukemias (e.g., acute myeloid, acute lymphocytic and chronic myeloid) and cancers (e.g., breast, lung, thyroid or gastrointestinal cancer or a melanoma). The patient may, but need not, be afflicted with the malignant disease, and the administration of the pharmaceutical composition or vaccine may inhibit the onset of such a disease, or may inhibit progression and/or metastasis of an existing disease.

The present invention further provides, within other aspects, methods for removing cells expressing WT1 from bone marrow and/or peripheral blood or fractions thereof, comprising contacting bone marrow, peripheral blood or a fraction of bone marrow or peripheral blood with T cells that specifically react with a WT1 polypeptide, wherein the step of contacting is performed under conditions and for a time sufficient to permit the removal of WT1 positive cells to less than 10%, preferably less than 5% and more preferably less than 1%, of the number of myeloid or lymphatic cells in the bone marrow, peripheral blood or fraction. Bone marrow, peripheral blood and fractions may be obtained from a patient afflicted with a disease associated with WT1 expression, or may be obtained from a human or non-human mammal not afflicted with such a disease.

Within related aspects, the present invention provides methods for inhibiting the development of a malignant disease in a patient, comprising administering to a patient bone marrow, peripheral blood or a fraction of bone marrow or peripheral blood prepared as described above. Such bone marrow, peripheral blood or fractions may be autologous, or may be derived from a related or unrelated human or non-human animal (e.g., syngeneic or allogeneic).

In other aspects, the present invention provides methods for stimulating (or priming) and/or expanding T cells, comprising contacting T cells with a WT1 polypeptide under conditions and for a time sufficient to permit the stimulation and/or expansion of T cells. Such T cells may be autologous, allogeneic, syngeneic or unrelated WT1-specific T cells, and may be stimulated in vitro or in vivo. Expanded T cells may, within certain embodiments, be present within bone marrow, peripheral blood or a fraction of bone marrow or peripheral blood, and may (but need not) be clonal. Within certain embodiments, T cells may be present in a mammal during stimulation and/or expansion. WT1-specific T cells may be used, for example, within donor lymphocyte infusions.

Within related aspects, methods are provided for inhibiting the development of a malignant disease in a patient, comprising administering to a patient T cells prepared as described above. Such T cells may, within certain embodiments, be autologous, syngeneic or allogeneic.

The present invention further provides, within other aspects, methods for monitoring the effectiveness of an immunization or therapy for a malignant disease associated with WT1 expression in a patient. Such methods are based on monitoring antibody, CD4+ T cell and/or CD8+ T cell responses in the patient. Within certain such aspects, a method may comprise the steps of: (a) incubating a first biological sample with one or more of: (i) a WT1 polypeptide; (ii) a polynucleotide encoding a WT1 polypeptide; or (iii) an antigen presenting cell that expresses a WT1 polypeptide, wherein the first biological sample is obtained from a patient prior to a therapy or immunization, and wherein the incubation is performed under conditions and for a time sufficient to allow immunocomplexes to form; (b) detecting immunocomplexes formed between the WT1 polypeptide and antibodies in the biological sample that specifically bind to the WT1 polypeptide; (c) repeating steps (a) and (b) using a second biological sample obtained from the same patient following therapy or immunization; and (d) comparing the number of immunocomplexes detected in the first and second biological samples, and therefrom monitoring the effectiveness of the therapy or immunization in the patient.

Within certain embodiments of the above methods, the step of detecting comprises (a) incubating the immunocomplexes with a detection reagent that is capable of binding to the immunocomplexes, wherein the detection reagent comprises a reporter group, (b) removing unbound detection reagent, and (c) detecting the presence or absence of the reporter group. The detection reagent may comprise, for example, a second antibody, or antigen-binding fragment thereof, capable of binding to the antibodies that specifically bind to the WT1 polypeptide or a molecule such as Protein A. Within other embodiments, a reporter group is bound to the WT1 polypeptide, and the step of detecting comprises removing unbound WT1 polypeptide and subsequently detecting the presence or absence of the reporter group.

Within further aspects, methods for monitoring the effectiveness of an immunization or therapy for a malignant disease associated with WT1 expression in a patient may comprise the steps of: (a) incubating a first biological sample with one or more of: (i) a WT1 polypeptide; (ii) a polynucleotide encoding a WT1 polypeptide; or (iii) an antigen presenting cell that expresses a WT1 polypeptide, wherein the biological sample comprises CD4+ and/or CD8+ T cells and is obtained from a patient prior to a therapy or immunization, and wherein the incubation is performed under conditions and for a time sufficient to allow specific activation, proliferation and/or lysis of T cells; (b) detecting an amount of activation, proliferation and/or lysis of the T cells; (c) repeating steps (a) and (b) using a second biological sample comprising CD4+ and/or CD8+ T cells, wherein the second biological sample is obtained from the same patient following therapy or immunization; and (d) comparing the amount of activation, proliferation and/or lysis of T cells in the first and second biological samples, and therefrom monitoring the effectiveness of the therapy or immunization in the patient.

The present invention further provides methods for inhibiting the development of a malignant disease associated with WT1 expression in a patient, comprising the steps of: (a) incubating CD4$^+$ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide, such that the T cells proliferate; and (b) administering to the patient an effective amount of the proliferated T cells, and therefrom inhibiting the development of a malignant disease in the patient. Within certain embodiments, the step of incubating the T cells may be repeated one or more times.

Within other aspects, the present invention provides methods for inhibiting the development of a malignant disease associated with WT1 expression in a patient, comprising the steps of: (a) incubating CD4$^+$ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide, such that the T cells proliferate; (b) cloning one or more cells that proliferated; and (c) administering to the patient an effective amount of the cloned T cells.

Within other aspects, methods are provided for determining the presence or absence of a malignant disease associated with WT1 expression in a patient, comprising the steps of: (a) incubating CD4$^+$ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide; and (b) detecting the presence or absence of specific activation of the T cells, therefrom determining the presence or absence of a malignant disease associated with WT1 expression. Within certain embodiments, the step of detecting comprises detecting the presence or absence of proliferation of the T cells.

Within further aspects, the present invention provides methods for determining the presence or absence of a malignant disease associated with WT1 expression in a patient, comprising the steps of: (a) incubating a biological sample obtained from a patient with one or more of: (i) a WT1 polypeptide; (ii) a polynucleotide encoding a WT1 polypeptide; or (iii) an antigen presenting cell that expresses a WT1 polypeptide, wherein the incubation is performed under conditions and for a time sufficient to allow immunocomplexes to form; and (b) detecting immunocomplexes formed between the WT1 polypeptide and antibodies in the biological sample that specifically bind to the WT1 polypeptide; and therefrom determining the presence or absence of a malignant disease associated with WT1 expression.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 depicts a comparison of the mouse (MO) and human (HU) WT1 protein sequences (SEQ ID NOS: 320 and 319 respectively).

FIG. 6A illustrates the lysis of target cells by allogeneic cell lines and FIG. 6B shows the lysis of peptide coated cell lines. In each case, the % lysis (as determined by standard chromium release assays) is shown at three indicated effector:target ratios. Results are provided for lymphoma cells (LSTRA and E10), as well as E10+p235–243 (E10+P235).

FIG. 7A illustrates that T-cells of non-immunized B6 mice to not kill WT1 positive tumor cell lines. FIG. 7B illustrates the lysis of the target cells by allogeneic cell lines. FIGS. 7C and 7D demonstrate the lysis of WT1 positive tumor cell lines, as compared to WT1 negative cell lines in two different experiments. In addition, FIGS. 7C and 7D show the lysis of peptide-coated cell lines (WT1 negative cell line E10 coated with the relevant WT1 peptide P117) In each case, the % lysis (as determined by standard chromium release assays) is shown at three indicated effector:target ratios. Results are provided for lymphoma cells (E10), prostate cancer cells (TrampC), a transformed fibroblast cell line (BLK SV40), as well as E10+p117.

FIGS. 8A and 8B present the results of TSITES Analysis of human WT1 (SEQ ID NO:319) for peptides that have the potential to elicit Th responses. Regions indicated by "A" are AMPHI midpoints of blocks, "R" indicates residues matching the Rothbard/Taylor motif, "D" indicates residues matching the IAd motif, and 'd' indicates residues matching the IEd motif.

DETAILED DESCRIPTION OF THE INVENTION

Figure 2:
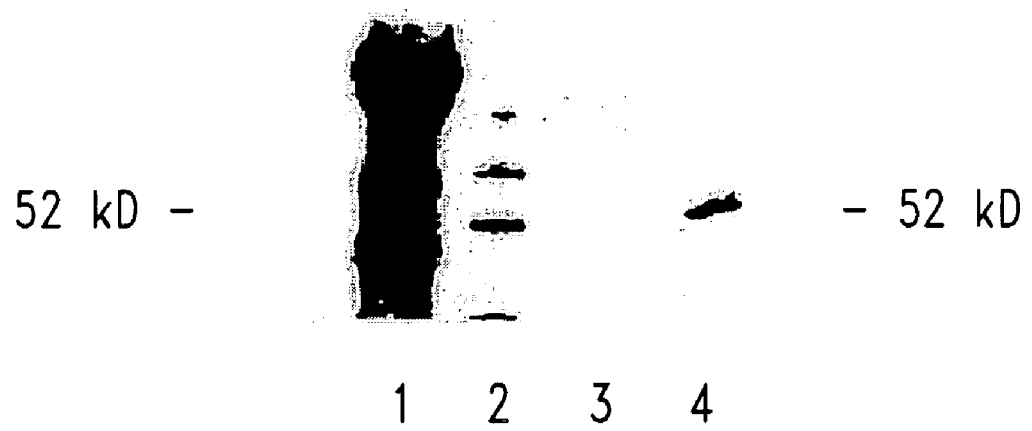
FIG. 2 is a Western blot illustrating the detection of WT1 specific antibodies in patients with hematological malignancy (AML). Lane 1 shows molecular weight markers; lane 2 shows a positive control (WT1 positive human leukemia cell line immunoprecipitated with a WT1 specific antibody); lane 3 shows a negative control (WT1 positive cell line immunoprecipitated with mouse sera); and lane 4 shows a WT1 positive cell line immunoprecipitated with sera of a patient with AML. For lanes 2–4, the immunoprecipitate was separated by gel electrophoresis and probed with a WT1 specific antibody.

As noted above, the present invention is generally directed to compositions and methods for the immunotherapy and diagnosis of malignant diseases. The compositions described herein may include WT1 polypeptides, WT1 polynucleotides, antigen-presenting cells (APC, e.g., dendritic cells) that express a WT1 polypeptide, agents such as antibodies that bind to a WT1 polypeptide and/or immune system cells (e.g., T cells) specific for WT1. WT1 Polypeptides of the present invention generally comprise at least a portion of a Wilms Tumor gene product (WT1) or a variant thereof. Nucleic acid sequences of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a portion of a WT1 polypeptide. T cells that may be employed within such compositions are generally T cells (e.g., CD4$^+$ and/or CD8$^+$) that are specific for a WT1 polypeptide. Certain methods described herein further employ antigen-presenting cells that express a WT1 polypeptide as provided herein.

The present invention is based on the discovery that an immune response raised against a Wilms Tumor (WT) gene product (e.g., WT1) can provide prophylactic and/or therapeutic benefit for patients afflicted with malignant diseases characterized by increased WT1 gene expression. Such diseases include, but are not limited to, leukemias (e.g., acute myeloid leukemia (AML), chronic myeloid leukemia (CML), acute lymphocytic leukemia (ALL) and childhood ALL), as well as many cancers such as lung, breast, thyroid and gastrointestinal cancers and melanomas. The WT1 gene was originally identified and isolated on the basis of a cytogenetic deletion at chromosome 11p13 in patients with Wilms' tumor (see Call et al., U.S. Pat. No. 5,350,840). The gene consists of 10 exons and encodes a zinc finger transcription factor, and sequences of mouse and human WT1 proteins are provided in FIG. 1 and SEQ ID NOs: 319 and 320.

WT1 Polypeptides

Within the context of the present invention, a WT1 polypeptide is a polypeptide that comprises at least an immunogenic portion of a native WT1 (i.e., a WT1 protein expressed by an organism that is not genetically modified), or a variant thereof, as described herein. A WT1 polypeptide may be of any length, provided that it comprises at least an immunogenic portion of a native protein or a variant thereof. In other words, a WT1 polypeptide may be an oligopeptide (i.e., consisting of a relatively small number of amino acid residues, such as 8–1 0 residues, joined by peptide bonds), a full length WT1 protein (e.g., present within a human or non-human animal, such as a mouse) or a polypeptide of intermediate size. Within certain embodiments, the use of WT1 polypeptides that contain a small number of consecutive amino acid residues of a native WT1 polypeptide is preferred. Such polypeptides are preferred for certain uses in which the generation of a T cell response is desired. For example, such a WT1 polypeptide may contain less than 23, preferably no more than 18, and more preferably no more than 15 consecutive amino acid residues, of a native WT1 polypeptide. Polypeptides comprising nine consecutive amino acid residues of a native WT1 polypeptide are generally suitable for such purposes. Additional sequences derived from the native protein and/or heterologous sequences may be present within any WT1 polypeptide, and such sequences may (but need not) possess further immunogenic or antigenic properties. Polypeptides as provided herein may further be associated (covalently or noncovalently) with other polypeptide or non-polypeptide compounds.

An "immunogenic portion," as used herein is a portion of a polypeptide that is recognized (i.e., specifically bound) by a B-cell and/or T-cell surface antigen receptor. Certain preferred immunogenic portions bind to an MHC class I or class II molecule. As used herein, an immunogenic portion is said to "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β2-microglobulin (β2m) into MHC class I/β2 m/peptide heterotrimeric complexes (see Parker et al., J. Immunol. 152:163, 1994). Alternatively, functional peptide competition assays that are known in the art may be employed. Certain immunogenic portions have one or more of the sequences recited within one or more of Tables II–XIV. Representative immunogenic portions include, but are not limited to, RDLNALLPAVPSLGGGG (human WT1 residues 6–22; SEQ ID NO:1), PSQASSGQARMFPNAPYLPSCLE (human and mouse WT1 residues 117–139; SEQ ID NOs: 2 and 3 respectively), GATLKGVAAGSSSSVKWTE (human WT1 residues 244–262; SEQ ID NO:4), GATLKGVAA (human WT1 residues 244–252; SEQ ID NO:88), CMTWNQMNL (human and mouse WT1 residues 235–243; SEQ ID NOs: 49 and 258 respectively), SCLESQPTI (mouse WT1 residues 136–144; SEQ ID NO:296), SCLESQPAI (human WT1 residues 136–144; SEQ ID NO:198), NLYQMTSQL (human and mouse WT1 residues 225–233; SEQ ID NOs: 147 and 284 respectively); ALLPAVSSL (mouse WT1 residues 10–18; SEQ ID NO:255); or RMFPNAPYL (human and mouse WT1 residues 126–134; SEQ ID NOs: 185 and 293 respectively). Further immunogenic portions are provided herein, and others may generally be identified using well known techniques, such as those summarized in Paul, *Fundamental Immunology*, 3rd ed., 243–247 (Raven Press, 1993) and references cited therein. Representative techniques for identifying immunogenic portions include screening polypeptides for the ability to react with antigen-specific antisera and/or T-cell lines or clones. An immunogenic portion of a native WT1 polypeptide is a portion that reacts with such antisera and/or T-cells at a level that is not substantially less than the reactivity of the full length WT1 (e.g., in an ELISA and/or T-cell reactivity assay). In other words, an immunogenic portion may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988.

Alternatively, immunogenic portions may be identified using computer analysis, such as the Tsites program (see Rothbard and Taylor, *EMBO J.* 7:93–100, 1988; Deavin et al., *Mol. Immunol.* 33:145–155, 1996), which searches for peptide motifs that have the potential to elicit Th responses. CTL peptides with motifs appropriate for binding to murine and human class I or class II MHC may be identified according to BIMAS (Parker et al., *J. Immunol.* 152:163, 1994) and other HLA peptide binding prediction analyses. To confirm immunogenicity, a peptide may be tested using an HLA A2 transgenic mouse model and/or an in vitro stimulation assay using dendritic cells, fibroblasts or peripheral blood cells.

As noted above, a composition may comprise a variant of a native WT1 protein. A polypeptide "variant," as used herein, is a polypeptide that differs from a native polypeptide in one or more substitutions, deletions, additions and/or insertions, such that the immunogenicity of the polypeptide is retained (i.e., the ability of the variant to react with antigen-specific antisera and/or T-cell lines or clones is not substantially diminished relative to the native polypeptide). In other words, the ability of a variant to react with antigen-specific antisera and/or T-cell lines or clones may be enhanced or unchanged, relative to the native polypeptide, or may be diminished by less than 50%, and preferably less than 20%, relative to the native polypeptide. Such variants may generally be identified by modifying one of the above polypeptide sequences and evaluating the reactivity of the modified polypeptide with antisera and/or T-cells as described herein. It has been found, within the context of the present invention, that a relatively small number of substitutions (e.g., 1 to 3) within an immunogenic portion of a WT1 polypeptide may serve to enhance the ability of the polypeptide to elicit an immune response. Suitable substitutions may generally be identified by using computer programs, as described above, and the effect confirmed based on the reactivity of the modified polypeptide with antisera and/or T-cells as described herein. Accordingly, within certain preferred embodiments, a WT1 polypeptide comprises a variant in which 1 to 3 amino acid resides within an immunogenic portion are substituted such that the ability to react with antigen-specific antisera and/or T-cell lines or clones is statistically greater than that for the unmodified polypeptide. Such substitutions are preferably located within an MHC binding site of the polypeptide, which may be identified as described above. Preferred substitutions allow increased binding to MHC class I or class II molecules.

Certain variants contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, WT1 polypeptides may be conjugated to a signal (or leader) sequence at the N-terminal end of the protein which co-translationally or post-translationally directs transfer of the protein. A polypeptide may also, or alternatively, be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

WT1 polypeptides may be prepared using any of a variety of well known techniques. Recombinant polypeptides encoded by a WT1 polynucleotide as described herein may be readily prepared from the polynucleotide. In general, any of a variety of expression vectors known to those of ordinary skill in the art may be employed to express recombinant WT1 polypeptides. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. The concentrate may then be applied to a suitable purification matrix such as an affinity matrix or an ion exchange resin. Finally, one or more reverse phase HPLC steps can be employed to further purify a recombinant polypeptide. Such techniques may be used to prepare native polypeptides or variants thereof. For example, polynucleotides that encode a variant of a native polypeptide may generally be prepared using standard mutagenesis techniques, such as oligonucleotide-directed site-specific mutagenesis, and sections of the DNA sequence may be removed to permit preparation of truncated polypeptides.

Certain portions and other variants may also be generated by synthetic means, using techniques well known to those of ordinary skill in the art. For example, polypeptides having fewer than about 500 amino acids, preferably fewer than about 100 amino acids, and more preferably fewer than about 50 amino acids, may be synthesized. Polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

In general, polypeptides and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Within further aspects, the present invention provides mimetics of WT1 polypeptides. Such mimetics may comprise amino acids linked to one or more amino acid mimetics (i.e., one or more amino acids within the WT1 protein may be replaced by an amino acid mimetic) or may be entirely nonpeptide mimetics. An amino acid mimetic is a compound that is conformationally similar to an amino acid such that it can be substituted for an amino acid within a WT1 polypeptide without substantially diminishing the ability to react with antigen-specific antisera and/or T cell lines or clones. A nonpeptide mimetic is a compound that does not contain amino acids, and that has an overall conformation that is similar to a WT1 polypeptide such that the ability of the mimetic to react with WT1-specific antisera and/or T cell lines or clones is not substantially diminished relative to the ability of a WT1 polypeptide. Such mimetics may be designed based on standard techniques (e.g., nuclear magnetic resonance and computational techniques) that evaluate the three dimensional structure of a peptide sequence. Mimetics may be designed where one or more of the side chain functionalities of the WT1 polypeptide are replaced by groups that do not necessarily have the same size or volume, but have similar chemical and/or physical properties which produce similar biological responses. It should be understood that, within embodiments described herein, a mimetic may be substituted for a WT1 polypeptide.

WT1 Polynucleotides

Any polynucleotide that encodes a WT1 polypeptide as described herein is a WT1 polynucleotide encompassed by the present invention. Such polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

WT1 polynucleotides may encode a native WT1 protein, or may encode a variant of WT1 as described herein. Polynucleotide variants may contain one or more substitutions, additions, deletions and/or insertions such that the immunogenicity of the encoded polypeptide is not diminished, relative to a native WT1 protein. The effect on the immunogenicity of the encoded polypeptide may generally be assessed as described herein. Preferred variants contain nucleotide substitutions, deletions, insertions and/or additions at no more than 20%, preferably at no more than 10%, of the nucleotide positions that encode an immunogenic portion of a native WT1 sequence. Certain variants are substantially homologous to a native gene, or a portion thereof. Such polynucleotide variants are capable of hybridizing under moderately stringent conditions to a naturally occurring DNA sequence encoding a WT1 polypeptide (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS). Such hybridizing DNA sequences are also within the scope of this invention.

It will be appreciated by those of ordinary skill in the art that, as a result of the degeneracy of the genetic code, there are many nucleotide sequences that encode a WT1 polypeptide. Some of these polynucleotides bear minimal homology to the nucleotide sequence of any native gene. Nonetheless, polynucleotides that vary due to differences in codon usage are specifically contemplated by the present invention.

Once an immunogenic portion of WT1 is identified, as described above, a WT1 polynucleotide may be prepared using any of a variety of techniques. For example, a WT1 polynucleotide may be amplified from cDNA prepared from cells that express WT1. Such polynucleotides may be amplified via polymerase chain reaction (PCR). For this approach, sequence-specific primers may be designed based on the sequence of the immunogenic portion and may be purchased or synthesized. For example, suitable primers for PCR amplification of a human WT1 gene include: first step—P118: 1434–1414: 5' GAG AGT CAG ACT TGA AAG CAGT 3' (SEQ ID NO:5) and P135: 5' CTG AGC CTC AGC AAA TGG GC 3' (SEQ ID NO:6); second step—P136: 5' GAG CAT GCA TGG GCT CCG ACG TGC GGG 3' (SEQ ID NO:7) and P137: 5' GGG GTA CCC ACT GAA CGG TCC CCG A 3' (SEQ ID NO:8). Primers for PCR amplification of a mouse WT1 gene include: first step—P138: 5' TCC GAG CCG CAC CTC ATG 3' (SEQ ID NO:9) and P139: 5' GCC TGG GAT GCT GGA CTG 3' (SEQ ID NO:10), second step—P140: 5' GAG CAT GCG ATG GGT TCC GAC GTG CGG 3' (SEQ ID NO:11) and P141: 5' GGG GTA CCT CAA AGC GCC ACG TGG AGT TT 3' (SEQ ID NO:12).

An amplified portion may then be used to isolate a full length gene from a human genomic DNA library or from a suitable cDNA library, using well known techniques. Alternatively, a full length gene can be constructed from multiple PCR fragments. WT1 polynucleotides may also be prepared by synthesizing oligonucleotide components, and ligating components together to generate the complete polynucleotide.

WT1 polynucleotides may also be synthesized by any method known in the art, including chemical synthesis (e.g., solid phase phosphoramidite chemical synthesis). Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a WT1 polypeptide, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells such as dendritic cells with a cDNA construct encoding a WT1 polypeptide, and administering the transfected cells to the patient).

Polynucleotides that encode a WT1 polypeptide may generally be used for production of the polypeptide, in vitro or in vivo. WT1 polynucleotides that are complementary to a coding sequence (i.e., antisense polynucleotides) may also be used as a probe or to inhibit WT1 expression. cDNA constructs that can be transcribed into antisense RNA may also be introduced into cells of tissues to facilitate the production of antisense RNA.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art. cDNA constructs within such a vector may be used, for example, to transfect human or animal cell lines for use in establishing WT1 positive tumor models which may be used to perform tumor protection and adoptive immunotherapy experiments to demonstrate tumor or leukemia-growth inhibition or lysis of such cells.

Other therapeutic formulations for polynucleotides include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antibodies and Fragments Thereof

The present invention further provides binding agents, such as antibodies and antigen-binding fragments thereof, that specifically bind to a WT1 polypeptide. As used herein, an agent is said to "specifically bind" to a WT1 polypeptide if it reacts at a detectable level (within, for example, an ELISA) with a WT1 polypeptide, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind, in the context of the present invention, when the binding constant for complex formation exceeds about $10^3$ L/mol. The binding constant maybe determined using methods well known in the art.

Any agent that satisfies the above requirements may be a binding agent. In a preferred embodiment, a binding agent is an antibody or an antigen-binding fragment thereof. Certain antibodies are commercially available from, for example, Santa Cruz Biotechnology (Santa Cruz, Calif.). Alternatively, antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies and fragments thereof may be coupled to one or more therapeutic agents. Suitable agents in this regard include radioactive tracers and chemotherapeutic agents, which may be used, for example, to purge autologous bone marrow in vitro). Representative therapeutic agents include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein. For diagnostic purposes, coupling of radioactive agents may be used to facilitate tracing of metastases or to determine the location of WT1-positive tumors.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used. A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of WT1. Such antibodies may be raised against an antibody, or antigen-binding fragment thereof, that specifically binds to an immunogenic portion of WT1, using well known techniques. Anti-idiotypic antibodies that mimic an immunogenic portion of WT1 are those antibodies that bind to an antibody, or antigen-binding fragment thereof, that specifically binds to an immunogenic portion of WT1, as described herein.

T Cells

Immunotherapeutic compositions may also, or alternatively, comprise T cells specific for WT1. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell Wash. (see also U.S. Pat. No. 5,240,856; U.S. Pat. No. 5,215,926; WO 89/06280; WO 91/16116 and WO 92/07243). Alternatively, T cells may be derived from related or unrelated humans, non-human animals, cell lines or cultures.

T cells may be stimulated with WT1 polypeptide, polynucleotide encoding a WT1 polypeptide and/or an antigen presenting cell (APC) that expresses a WT1 polypeptide. Such stimulation is performed under conditions and for a time sufficient to permit the generation of T cells that are specific for the WT1 polypeptide. Preferably, a WT1 polypeptide or polynucleotide is present within a delivery vehicle, such as a microsphere, to facilitate the generation of antigen-specific T cells. Briefly, T cells, which may be isolated from a patient or a related or unrelated donor by routine techniques (such as by Ficoll/Hypaque density gradient centrifugation of peripheral blood lymphocytes), are incubated with WT1 polypeptide. For example, T cells may be incubated in vitro for 2–9 days (typically 4 days) at 37° C. with WT1 polypeptide (e.g., 5 to 25 µg/ml) or cells synthesizing a comparable amount of WT1 polypeptide. It may be desirable to incubate a separate aliquot of a T cell sample in the absence of WT1 polypeptide to serve as a control.

T cells are considered to be specific for a WT1 polypeptide if the T cells kill target cells coated with a WT1 polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a WT1 polypeptide may be quantified. Contact with a WT1 polypeptide (200 ng/ml–100 µg/ml, preferably 100 ng/ml–25 µg/ml) for 3–7 days should result in at least a two fold increase in proliferation of the T cells and/or contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998). WT1 specific T cells may be expanded using standard techniques. Within preferred embodiments, the T cells are derived from a patient or a related or unrelated donor and are administered to the patient following stimulation and expansion.

T cells that have been activated in response to a WT1 polypeptide, polynucleotide or WT1-expressing APC may be $CD4^+$ and/or $CD8^+$. Specific activation of $CD4^+$ or $CD8^+$ T cells may be detected in a variety of ways. Methods for detecting specific T cell activation include detecting the proliferation of T cells, the production of cytokines (e.g., lymphokines), or the generation of cytolytic activity (i.e., generation of cytotoxic T cells specific for WT1). For $CD4^+$ T cells, a preferred method for detecting specific T cell activation is the detection of the proliferation of T cells. For $CD8^+$ T cells, a preferred method for detecting specific T cell activation is the detection of the generation of cytolytic activity.

For therapeutic purposes, $CD4^+$ or $CD8^+$ T cells that proliferate in response to the WT1 polypeptide, polynucleotide or APC can be expanded in number either in vitro or in vivo. Proliferation of such T cells in vitro may be accomplished in a variety of ways. For example, the T cells can be re-exposed to WT1 polypeptide, with or without the addition of T cell growth factors, such as interleukin-2, and/or stimulator cells that synthesize a WT1 polypeptide. The addition of stimulator cells is preferred where generating $CD8^+$ T cell responses. T cells can be grown to large numbers in vitro with retention of specificity in response to intermittent restimulation with WT1 polypeptide. Briefly, for the primary in vitro stimulation (IVS), large numbers of lymphocytes (e.g., greater than $4 \times 10^7$) may be placed in flasks with media containing human serum. WT1 polypeptide (e.g., peptide at 10 μg/ml) may be added directly, along with tetanus toxoid (e.g., 5 μg/ml). The flasks may then be incubated (e.g., 37° C. for 7 days). For a second IVS, T cells are then harvested and placed in new flasks with $2-3 \times 10^7$ irradiated peripheral blood mononuclear cells. WT1 polypeptide (e.g., 10 μg/ml) is added directly. The flasks are incubated at 37° C. for 7 days. On day 2 and day 4 after the second IVS, 2–5 units of interleukin-2 (IL-2) may be added. For a third IVS, the T cells may be placed in wells and stimulated with the individual's own EBV transformed B cells coated with the peptide. IL-2 may be added on days 2 and 4 of each cycle. As soon as the cells are shown to be specific cytotoxic T cells, they may be expanded using a 10 day stimulation cycle with higher IL-2 (20 units) on days 2, 4 and 6.

Alternatively, one or more T cells that proliferate in the presence of WT1 polypeptide can be expanded in number by cloning. Methods for cloning cells are well known in the art, and include limiting dilution. Responder T cells may be purified from the peripheral blood of sensitized patients by density gradient centrifugation and sheep red cell rosetting and established in culture by stimulating with the nominal antigen in the presence of irradiated autologous filler cells. In order to generate $CD4^+$ T cell lines, WT1 polypeptide is used as the antigenic stimulus and autologous peripheral blood lymphocytes (PBL) or lymphoblastoid cell lines (LCL) immortalized by infection with Epstein Barr virus are used as antigen presenting cells. In order to generate $CD8^+$ T cell lines, autologous antigen-presenting cells transfected with an expression vector which produces WT1 polypeptide may be used as stimulator cells. Established T cell lines may be cloned 2–4 days following antigen stimulation by plating stimulated T cells at a frequency of 0.5 cells per well in 96-well flat-bottom plates with $1 \times 10^6$ irradiated PBL or LCL cells and recombinant interleukin-2 (rIL2) (50 U/ml). Wells with established clonal growth may be identified at approximately 2–3 weeks after initial plating and restimulated with appropriate antigen in the presence of autologous antigen-presenting cells, then subsequently expanded by the addition of low doses of rIL2 (10 U/ml) 2–3 days following antigen stimulation. T cell clones may be maintained in 24-well plates by periodic restimulation with antigen and rIL2 approximately every two weeks.

Within certain embodiments, allogeneic T-cells may be primed (i.e., sensitized to WT1) in vivo and/or in vitro. Such priming may be achieved by contacting T cells with a WT1 polypeptide, a polynucleotide encoding such a polypeptide or a cell producing such a polypeptide under conditions and for a time sufficient to permit the priming of T cells. In general, T cells are considered to be primed if, for example, contact with a WT1 polypeptide results in proliferation and/or activation of the T cells, as measured by standard proliferation, chromium release and/or cytokine release assays as described herein. A stimulation index of more than two fold increase in proliferation or lysis, and more than three fold increase in the level of cytokine, compared to negative controls, indicates T-cell specificity. Cells primed in vitro may be employed, for example, within a bone marrow transplantation or as donor lymphocyte infusion.

Pharmaceutical Compositions and Vaccines

Within certain aspects, polypeptides, polynucleotides, antibodies and/or T cells may be incorporated into pharmaceutical compositions or vaccines. Alternatively, a pharmaceutical composition may comprise an antigen-presenting cell (e.g., a dendritic cell) transfected with a WT1 polynucleotide such that the antigen presenting cell expresses a WT1 polypeptide. Pharmaceutical compositions comprise one or more such compounds or cells and a physiologically acceptable carrier or excipient. Certain vaccines may comprise one or more such compounds or cells and a non-specific immune response enhancer, such as an adjuvant or a liposome (into which the compound is incorporated). Pharmaceutical compositions and vaccines may additionally contain a delivery system, such as biodegradable microspheres which are disclosed, for example, in U.S. Pat. Nos. 4,897,268 and 5,075,109. Pharmaceutical compositions and vaccines within the scope of the present invention may also contain other compounds, which may be biologically active or inactive.

Within certain embodiments, pharmaceutical compositions and vaccines are designed to elicit T cell responses specific for a WT1 polypeptide in a patient, such as a human. In general, T cell responses may be favored through the use of relatively short polypeptides (e.g., comprising less than 23 consecutive amino acid residues of a native WT1 polypeptide, preferably 4–16 consecutive residues, more preferably 8–16 consecutive residues and still more preferably 8–10 consecutive residues. Alternatively, or in addition, a vaccine may comprise a non-specific immune response enhancer that preferentially enhances a T cell response. In other words, the immune response enhancer may enhance the level of a T cell response to a WT1 polypeptide by an amount that is proportionally greater than the amount by which an antibody response is enhanced. For example, when compared to a standard oil based adjuvant, such as CFA, an immune response enhancer that preferentially enhances a T cell response may enhance a proliferative T cell response by at least two fold, a lytic response by at least 10%, and/or T cell activation by at least two fold compared to WT1-megative control cell lines, while not detectably enhancing an antibody response. The amount by which a T cell or antibody response to a WT1 polypeptide is enhanced may generally be determined using any representative technique known in the art, such as the techniques provided herein.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacterial and viral expression systems and mammalian expression systems. Appropriate nucleic acid expression systems contain the necessary DNA, cDNA or RNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

As noted above, a pharmaceutical composition or vaccine may comprise an antigen-presenting cell that expresses a WT1 polypeptide. For therapeutic purposes, as described herein, the antigen presenting cell is preferably an autologous dendritic cell. Such cells may be prepared and transfected using standard techniques, such as those described by Reeves et al., *Cancer Res.* 56:5672–5677, 1996; Tuting et al., *J. Immunol.* 160:1139–1147, 1998; and Nair et al., *Nature Biotechnol.* 16:364–369, 1998). Expression of a WT1 polypeptide on the surface of an antigen-presenting cell may be confirmed by in vitro stimulation and standard proliferation as well as chromium release assays, as described herein.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. For certain topical applications, formulation as a cream or lotion, using well known components, is preferred.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers, such as adjuvants, may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable non-specific immune response enhancers include alum-based adjuvants (e.g., Alhydrogel, Rehydragel, aluminum phosphate, Algammulin, aluminum hydroxide); oil based adjuvants (Freund's adjuvant (FA), Specol, RIBI, TiterMax, Montanide ISA50 or Seppic MONTANIDE ISA 720; cytokines (e.g., GM-CSF or Flt3-ligand); microspheres; nonionic block copolymer-based adjuvants; dimethyl dioctadecyl ammoniumbromide (DDA) based adjuvants AS-1, AS-2 (Smith Kline Beecham); Ribi Adjuvant system based adjuvants; QS21 (Aquila); saponin based adjuvants (crude saponin, the saponin Quil A); muramyl dipeptide (MDP) based adjuvants such as SAF (Syntex adjuvant in its microfluidized form (SAF-m)); dimethyl-dioctadecyl ammonium bromide (DDA); human complement based adjuvants *m. vaccae* and derivatives; immune stimulating complex (iscom) based adjuvants; inactivated toxins; and attenuated infectious agents (such as *M tuberculosis*).

As noted above, within certain embodiments, immune response enhancers are chosen for their ability to preferentially elicit or enhance a T cell response (e.g., CD4$^+$ and/or CD8$^+$) to a WT1 polypeptide. Such immune response enhancers are well known in the art, and include (but are not limited to) Montanide ISA50, Seppic MONTANIDE ISA 720, cytokines (e.g., GM-CSF, Flat3-ligand), microspheres, dimethyl dioctadecyl ammoniumbromide (DDA) based adjuvants, AS-1 (Smith Kline Beecham), AS-2 (Smith Kline Beecham), Ribi Adjuvant system based adjuvants, QS21 (Aquila), saponin based adjuvants (crude saponin, the saponin Quil A), Syntex adjuvant in its microfluidized form (SAF-m), MV, ddMV (Genesis), immune stimulating complex (iscom) based adjuvants and inactivated toxins.

The compositions and vaccines described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide, antibody or cell dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Therapy of Malignant Diseases

In further aspects of the present invention, the compositions and vaccines described herein may be used to inhibit the development of malignant diseases (e.g., progressive or metastatic diseases or diseases characterized by small tumor burden such as minimal residual disease). In general, such methods may be used to prevent, delay or treat a disease associated with WT1 expression. In other words, therapeutic methods provided herein may be used to treat an existing WT1-associated disease, or may be used to prevent or delay the onset of such a disease in a patient who is free of disease or who is afflicted with a disease that is not yet associated with WT1 expression.

As used herein, a disease is "associated with WT1 expression" if diseased cells (e.g., tumor cells) at some time during the course of the disease generate detectably higher levels of a WT1 polypeptide than normal cells of the same tissue. Association of WT1 expression with a malignant disease does not require that WT1 be present on a tumor. For example, overexpression of WT1 may be involved with initiation of a tumor, but the protein expression may subsequently be lost. Alternatively, a malignant disease that is not characterized by an increase in WT1 expression may, at a later time, progress to a disease that is characterized by increased WT1 expression. Accordingly, any malignant disease in which diseased cells formerly expressed, currently express or are expected to subsequently express increased levels of WT1 is considered to be "associated with WT1 expression."

Immunotherapy may be performed using any of a variety of techniques, in which compounds or cells provided herein function to remove WT1-expressing cells from a patient. Such removal may take place as a result of enhancing or inducing an immune response in a patient specific for WT1 or a cell expressing WT1. Alternatively, WT1-expressing cells may be removed ex vivo (e.g., by treatment of autologous bone marrow, peripheral blood or a fraction of bone marrow or peripheral blood). Fractions of bone marrow or peripheral blood may be obtained using any standard technique in the art.

Within such methods, pharmaceutical compositions and vaccines may be administered to a patient. As used herein, a "patient" refers to any warm-blooded animal, preferably a human. A patient may or may not be afflicted with a malignant disease. Accordingly, the above pharmaceutical compositions and vaccines may be used to prevent the onset of a disease (i.e., prophylactically) or to treat a patient afflicted with a disease (e.g., to prevent or delay progression and/or metastasis of an existing disease). A patient afflicted with a disease may have a minimal residual disease (e.g., a low tumor burden in a leukemia patient in complete or partial remission or a cancer patient following reduction of the tumor burden after surgery radiotherapy and/or chemotherapy). Such a patient may be immunized to inhibit a relapse (i.e., prevent or delay the relapse, or decrease the severity of a relapse). Within certain preferred embodiments, the patient is afflicted with a leukemia (e.g., AML, CML, ALL or childhood ALL), a myelodysplastic syndrome (MDS) or a cancer (e.g., gastrointestinal, lung, thyroid or breast cancer or a melanoma), where the cancer or leukemia is WT1 positive (i.e., reacts detectably with an anti-WT1 antibody, as provided herein or expresses WT1 mRNA at a level detectable by RT-PCR, as described herein) or suffers from an autoimmune disease directed against WT1-expressing cells.

The compositions provided herein may be used alone or in combination with conventional therapeutic regimens such as surgery, irradiation, chemotherapy and/or bone marrow transplantation (autologous, syngeneic, allogeneic or unrelated). As discussed in greater detail below, binding agents and T cells as provided herein may be used for purging of autologous stem cells. Such purging may be beneficial prior to, for example, bone marrow transplantation or transfusion of blood or components thereof. Binding agents, T cells, antigen presenting cells (APC) and compositions provided herein may further be used for expanding and stimulating (or priming) autologous, allogeneic, syngeneic or unrelated WT1-specific T-cells in vitro and/or in vivo. Such WT1-specific T cells may be used, for example, within donor lymphocyte infusions.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. In some tumors, pharmaceutical compositions or vaccines may be administered locally (by, for example, rectocoloscopy, gastroscopy, videoendoscopy, angiography or other methods known in the art). Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response that is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent complete or partial remissions, or longer disease-free and/or overall survival) in vaccinated patients as compared to non-vaccinated patients. In general, for pharmaceutical compositions and vaccines comprising one or more polypeptides, the amount of each polypeptide present in a dose ranges from about 100 µg to 5 mg. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent complete or partial remissions, or longer disease-free and/or overall survival) in treated patients as compared to non-treated patients. Increases in preexisting immune responses to WT1 generally correlate with an improved clinical outcome. Such immune responses may generally be evaluated using standard proliferation, cytotoxicity or cytokine assays, which may be performed using samples obtained from a patient before and after treatment.

Within further aspects, methods for inhibiting the development of a malignant disease associated with WT1 expression involve the administration of autologous T cells that have been activated in response to a WT1 polypeptide or WT1-expressing APC, as described above. Such T cells may be $CD4^+$ and/or $CD8^+$, and may be proliferated as described above. The T cells may be administered to the individual in an amount effective to inhibit the development of a malignant disease. Typically, about $1\times10^9$ to $1\times10^{11}$ T cells/$M^2$ are administered intravenously, intracavitary or in the bed of a resected tumor. It will be evident to those skilled in the art that the number of cells and the frequency of administration will be dependent upon the response of the patient.

Within certain embodiments, T cells may be stimulated prior to an autologous bone marrow transplantation. Such stimulation may take place in vivo or in vitro. For in vitro stimulation, bone marrow and/or peripheral blood (or a fraction of bone marrow or peripheral blood) obtained from a patient may be contacted with a WT1 polypeptide, a polynucleotide encoding a WT1 polypeptide and/or an APC that expresses a WT1 polypeptide under conditions and for a time sufficient to permit the stimulation of T cells as described above. Bone marrow, peripheral blood stem cells and/or WT1-specific T cells may then be administered to a patient using standard techniques.

Within related embodiments, T cells of a related or unrelated donor may be stimulated prior to a syngeneic or allogeneic (related or unrelated) bone marrow transplantation. Such stimulation may take place in vivo or in vitro. For in vitro stimulation, bone marrow and/or peripheral blood (or a fraction of bone marrow or peripheral blood) obtained from a related or unrelated donor may be contacted with a WT1 polypeptide, WT1 polynucleotide and/or APC that expresses a WT1 polypeptide under conditions and for a time sufficient to permit the stimulation of T cells as described above. Bone marrow, peripheral blood stem cells and/or WT1-specific T cells may then be administered to a patient using standard techniques.

Within other embodiments, WT1-specific T cells as described herein may be used to remove cells expressing WT1 from autologous bone marrow, peripheral blood or a fraction of bone marrow or peripheral blood (e.g. $CD34^+$ enriched peripheral blood (PB) prior to administration to a patient). Such methods may be performed by contacting bone marrow or PB with such T cells under conditions and for a time sufficient to permit the reduction of WT1 expressing cells to less than 10%, preferably less than 5% and more preferably less than 1%, of the total number of myeloid or lymphatic cells in the bone marrow or peripheral blood. The extent to which such cells have been removed may be readily determined by standard methods such as, for example, qualitative and quantitative PCR analysis, morphology, immunohistochemistry and FACS analysis. Bone marrow or PB (or a fraction thereof) may then be administered to a patient using standard techniques.

Diagnostic Methods

The present invention further provides methods for detecting a malignant disease associated with WT1 expression, and for monitoring the effectiveness of an immunization or therapy for such a disease. Such methods are based on the discovery, within the present invention, that an immune response specific for WT1 protein can be detected in patients afflicted with such diseases, and that methods which enhance such immune responses may provide a preventive or therapeutic benefit.

To determine the presence or absence of a malignant disease associated with WT1 expression, a patient may be tested for the level of T cells specific for WT1. Within certain methods, a biological sample comprising $CD4^+$ and/or $CD8^+$ T cells isolated from a patient is incubated with a WT1 polypeptide, a polynucleotide encoding a WT1 polypeptide and/or an APC that expresses a WT1 polypeptide, and the presence or absence of specific activation of the T cells is detected, as described herein. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with WT1 polypeptide (e.g., 5–25 μg/ml). It may be desirable to incubate another aliquot of a T cell sample in the absence of WT1 polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a malignant disease associated with WT1 expression. Further correlation may be made, using methods well known in the art, between the level of proliferation and/or cytolytic activity and the predicted response to therapy. In particular, patients that display a higher antibody, proliferative and/or lytic response may be expected to show a greater response to therapy.

Within other methods, a biological sample obtained from a patient is tested for the level of antibody specific for WT1. The biological sample is incubated with a WT1 polypeptide, a polynucleotide encoding a WT1 polypeptide and/or an APC that expresses a WT1 polypeptide under conditions and for a time sufficient to allow immunocomplexes to form. Immunocomplexes formed between the WT1 polypeptide and antibodies in the biological sample that specifically bind to the WT1 polypeptide are then detected. A biological sample for use within such methods may be any sample obtained from a patient that would be expected to contain antibodies. Suitable biological samples include blood, sera, ascites, bone marrow, pleural effusion, and cerebrospinal fluid.

The biological sample is incubated with the WT1 polypeptide in a reaction mixture under conditions and for a time sufficient to permit immunocomplexes to form between the polypeptide and antibodies specific for WT1. For example, a biological sample and WT1 polypeptide may be incubated at 4° C. for 24–48 hours.

Following the incubation, the reaction mixture is tested for the presence of immunocomplexes. Detection of immunocomplexes formed between the WT1 polypeptide and antibodies present in the biological sample may be accomplished by a variety of known techniques, such as radioimmunoassays (RIA) and enzyme linked immunosorbent assays (ELISA). Suitable assays are well known in the art and are amply described in the scientific and patent literature (e.g., Harlow and Lane, *Antibodies: A Laboratory Manual*, Cold Spring Harbor Laboratory, 1988). Assays that may be used include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh, 1970); the "western blot" method of Gordon et al. (U.S. Pat. No. 4,452,901); immunoprecipitation of labeled ligand (Brown et al., *J. Biol. Chem.* 255:4980–4983, 1980); enzyme-linked immunosorbent assays as described by, for example, Raines and Ross (*J. Biol. Chem.* 257:5154–5160, 1982); immunocytochemical techniques, including the use of fluorochromes (Brooks et al., *Clin. Exp. Immunol.* 39: 477, 1980); and neutralization of activity (Bowen-Pope et al., *Proc. Natl. Acad. Sci. USA* 81:2396–2400, 1984). Other immunoassays include, but are not limited to, those described in U.S. Pat. Nos. 3,817,827; 3,850,752; 3,901, 654; 3,935,074; 3,984,533; 3,996,345; 4,034,074; and 4,098,876.

For detection purposes, WT1 polypeptide may either be labeled or unlabeled. Unlabeled WT1 polypeptide may be used in agglutination assays or in combination with labeled detection reagents that bind to the immunocomplexes (e.g., anti-immunoglobulin, protein G, protein A or a lectin and secondary antibodies, or antigen-binding fragments thereof, capable of binding to the antibodies that specifically bind to the WT1 polypeptide). If the WT1 polypeptide is labeled, the reporter group may be any suitable reporter group known in the art, including radioisotopes, fluorescent groups, luminescent groups, enzymes, biotin and dye particles.

Within certain assays, unlabeled WT1 polypeptide is immobilized on a solid support. The solid support may be any material known to those of ordinary skill in the art to which the polypeptide may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The polypeptide may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the WT1 polypeptide, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of polypeptide ranging from about 10 ng to about 10 µg, and preferably about 100 ng to about 1 µg, is sufficient to immobilize an adequate amount of polypeptide.

Following immobilization, the remaining protein binding sites on the support are typically blocked. Any suitable blocking agent known to those of ordinary skill in the art, such as bovine serum albumin, Tween 20™ (Sigma Chemical Co., St. Louis, Mo.), heat-inactivated normal goat serum (NGS), or BLOTTO (buffered solution of nonfat dry milk which also contains a preservative, salts, and an antifoaming agent). The support is then incubated with a biological sample suspected of containing specific antibody. The sample can be applied neat, or, more often, it can be diluted, usually in a buffered solution which contains a small amount (0.1%–5.0% by weight) of protein, such as BSA, NGS, or BLOTTO. In general, an appropriate contact time (i.e., incubation time) is a period of time that is sufficient to detect the presence of antibody that specifically binds WT1 within a sample containing such an antibody. Preferably, the contact time is sufficient to achieve a level of binding that is at least about 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. A detection reagent that binds to the immunocomplexes and that comprises a reporter group may then be added. The detection reagent is incubated with the immunocomplex for an amount of time sufficient to detect the bound antibody. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups (e.g., horseradish peroxidase, beta-galactosidase, alkaline phosphatase and glucose oxidase) may generally be detected by the addition of substrate (generally for a specific period of time), followed by spectroscopic or other analysis of the reaction products. Regardless of the specific method employed, a level of bound detection reagent that is at least two fold greater than background (i.e., the level observed for a biological sample obtained from a disease-free individual) indicates the presence of a malignant disease associated with WT1 expression.

In general, methods for monitoring the effectiveness of an immunization or therapy involve monitoring changes in the level of antibodies or T cells specific for WT1 in the patient. Methods in which antibody levels are monitored may comprise the steps of: (a) incubating a first biological sample, obtained from a patient prior to a therapy or immunization, with a WT1 polypeptide, wherein the incubation is performed under conditions and for a time sufficient to allow immunocomplexes to form; (b) detecting immunocomplexes formed between the WT1 polypeptide and antibodies in the biological sample that specifically bind to the WT1 polypeptide; (c) repeating steps (a) and (b) using a second biological sample taken from the patient following therapy or immunization; and (d) comparing the number of immunocomplexes detected in the first and second biological samples. Alternatively, a polynucleotide encoding a WT1 polypeptide, or an APC expressing a WT1 polypeptide may be employed in place of the WT1 polypeptide. Within such methods, immunocomplexes between the WT1 polypeptide encoded by the polynucleotide, or expressed by the APC, and antibodies in the biological sample are detected.

Methods in which T cell activation and/or the number of WT1 specific precursors are monitored may comprise the steps of: (a) incubating a first biological sample comprising CD4+ and/or CD8+ cells (e.g., bone marrow, peripheral blood or a fraction thereof), obtained from a patient prior to a therapy or immunization, with a WT1 polypeptide, wherein the incubation is performed under conditions and for a time sufficient to allow specific activation, proliferation and/or lysis of T cells; (b) detecting an amount of activation, proliferation and/or lysis of the T cells; (c) repeating steps (a) and (b) using a second biological sample comprising CD4+ and/or CD8+ T cells, and taken from the same patient following therapy or immunization; and (d) comparing the amount of activation, proliferation and/or lysis of T cells in the first and second biological samples. Alternatively, a polynucleotide encoding a WT1 polypeptide, or an APC expressing a WT1 polypeptide may be employed in place of the WT1 polypeptide.

A biological sample for use within such methods may be any sample obtained from a patient that would be expected to contain antibodies, CD4+ T cells and/or CD8+ T cells. Suitable biological samples include blood, sera, ascites, bone marrow, pleural effusion and cerebrospinal fluid. A first biological sample may be obtained prior to initiation of therapy or immunization or part way through a therapy or vaccination regime. The second biological sample should be obtained in a similar manner, but at a time following additional therapy or immunization. The second biological sample may be obtained at the completion of, or part way through, therapy or immunization, provided that at least a portion of therapy or immunization takes place between the isolation of the first and second biological samples.

Incubation and detection steps for both samples may generally be performed as described above. A statistically significant increase in the number of immunocomplexes in the second sample relative to the first sample reflects successful therapy or immunization.

The following Examples are offered by way of illustration and not by way of limitation.

EXAMPLES

Example 1

Identification of an Immune Response to WT1 in Patients with Hematological Malignancies This Example illustrates the identification of an existent immune response in patients with a hematological malignancy.

To evaluate the presence of preexisting WT1 specific antibody responses in patients, sera of patients with AML, ALL, CML and severe aplastic anemia were analyzed using Western blot analysis. Sera were tested for the ability to immunoprecipitate WT1 from the human leukemic cell line K562 (American Type Culture Collection, Manassas, Va.). In each case, immunoprecipitates were separated by gel electrophoresis, transferred to membrane and probed with the anti WT-1 antibody WT180 (Santa Cruz Biotechnology, Inc., Santa Cruz, Calif.). This Western blot analysis identified potential WT1 specific antibodies in patients with hematological malignancy. A representative Western blot showing the results for a patient with AML is shown in FIG. 2. A 52 kD protein in the immunoprecipitate generated using the patient sera was recognized by the WT1 specific antibody. The 52 kD protein migrated at the same size as the positive control.

Example 2

Induction of Antibodies to WT1 in Mice Immunized with Cell Lines Expressing WT1

This Example illustrates the use of cells expressing WT1 to induce a WT1 specific antibody response in vivo.

Figure 3:
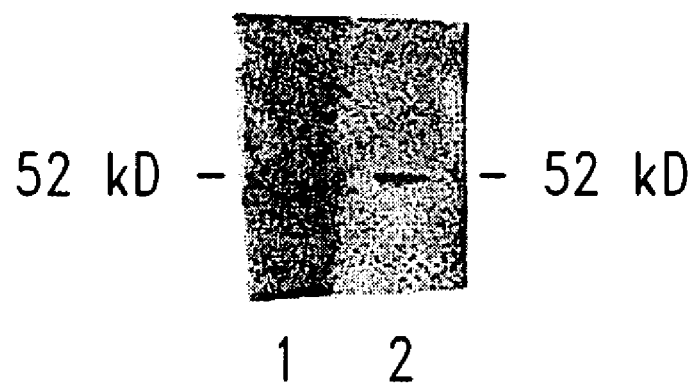
FIG. 3 is a Western blot illustrating the detection of a WT1 specific antibody response in B6 mice immunized with TrampC, a WT1 positive tumor cell line. Lane 1 shows molecular weight markers and lane 2 shows a WT1 specific positive control (N180, Santa Cruz Biotechnology, polypeptide spanning 180 amino acids of the N-terminal region of the WT1 protein, migrating on the Western blot at 52 kD) probed with sera of the immunized B6 mice.

Detection of existent antibodies to WT1 in patients with leukemia strongly implied that it is possible to immunize to WT1 protein to elicit immunity to WT1. To test whether immunity to WT1 can be generated by vaccination, mice were injected with TrampC, a WT1 positive tumor cell line of B6 origin. Briefly, male B6 mice were immunized with $5 \times 10^6$ TrampC cells subcutaneously and boosted twice with $5 \times 10^6$ cells at three week intervals. Following immunization to TrampC, a WT1 specific antibody response in the immunized animals was detectable. A representative Western blot is shown in FIG. 3. These results show that immunization to WT1 protein can elicit an immune response to WT1 protein.

Example 3

Induction of Th and Antibody Responses in Mice Immunized with WT1 Peptides

This Example illustrates the ability of immunization with WT1 peptides to elicit an immune response specific for WT1.

Peptides suitable for eliciting Ab and proliferative T cell responses were identified according to the Tsites program (Rothbard and Taylor, *EMBO J.* 7:93–100, 1988; Deavin et al., *Mol. Immunol.* 33:145–155, 1996), which searches for peptide motifs that have the potential to elicit Th responses. Peptides shown in Table I were synthesized and sequenced.

TABLE I

WT1 Peptides

| Peptide | Sequence | Comments |
|---|---|---|
| Mouse: p6–22 | RDLNALLPAVSSLGGGG (SEQ ID NO:13) | 1 mismatch relative to human WT1 sequence |
| Human: p6–22 | RDLNALLPAVPSLGGGG (SEQ ID NO:1) | |
| Human/mouse: p117–139 | PSQASSGQARMFPNAPYLPSCLE (SEQ ID NOs:2 and 3) | |
| Mouse: p244–262 | GATLKGMAAGSSSSVKWTE (SEQ ID NO:14) | 1 mismatch relative to human WT1 sequence |
| Human: p244–262 | GATLKGVAAGSSSSVKWTE (SEQ ID NO:4) | |
| Human/mouse: p287–301 | RIHTHGVFRGIQDVR (SEQ ID NOs:15 and 16) | |
| Mouse: p299–313 | VRRVSGVAPTLVRS (SEQ ID NO:17) | 1 mismatch relative to human WT1 sequence |
| Human/mouse: p421–435 | CQKKFARSDELVRHH (SEQ ID NOs:19 and 20) | |

For immunization, peptides were grouped as follows:

| | |
|---|---|
| Group A: | p6-22 human: 10.9 mg in 1 ml (10 μl = 100 μg)<br>p117-139 human/mouse: 7.6 mg in 1 ml (14 μl = 100 μg)<br>p244-262 human: 4.6. mg in 1 ml (22 μl = 100 μg) |
| Group B: | p287-301 human/mouse: 7.2 mg in 1 ml (14 μl = 100 μg)<br>mouse p299-313: 6.6. mg in 1 ml (15 μl = 100 μg)<br>p421-435 human/mouse: 3.3 mg in 1 ml (30 μl = 100 μg) |
| Control: | (FBL peptide 100 μg) + CFA/IFA |
| Control: | (CD45 peptide 100 μg) + CFA/IFA |

B6 mice were immunized with a group of WT1 peptides or with a control peptide. Peptides were dissolved in 1 ml sterile water for injection, and B6 mice were immunized 3 times at time intervals of three weeks. Adjuvants used were CFA/IFA, GM-CSF, and Montinide. The presence of antibodies specific for WT1 was then determined as described in Examples 1 and 2, and proliferative T cell responses were evaluated using a standard thymidine incorporation assay, in which cells were cultured in the presence of antigen and proliferation was evaluated by measuring incorporated radioactivity (Chen et al., *Cancer Res.* 54:1065–1070, 1994).

Figure 4:
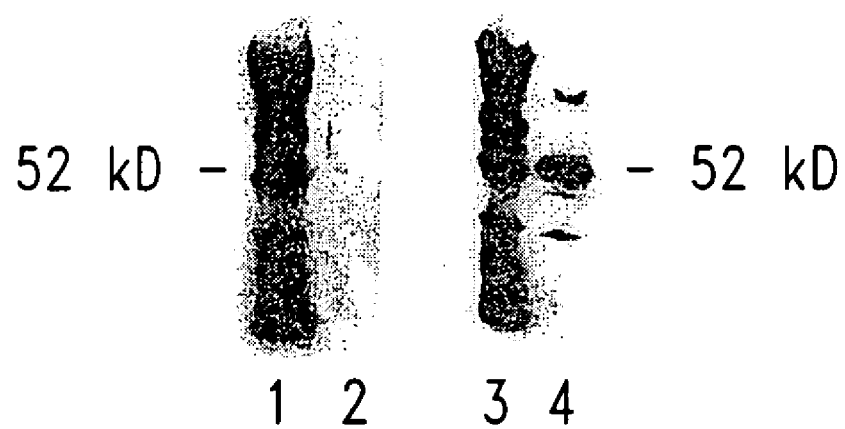
FIG. 4 is a Western blot illustrating the detection of WT1 specific antibodies in mice immunized with representative WT1 peptides. Lane 1 shows molecular weight markers and lane 2 shows a WT1 specific positive control (N180, Santa Cruz Biotechnology, polypeptide spanning 180 amino acids of the N-terminal region of the WT1 protein, migrating on the Western blot at 52 kD) probed with sera of non-immunized B6 mice. Lane 3 shows molecular weight markers and lane 4 shows the WT1 specific positive control probed with sera of the immunized B6 mice.
Figure 5A:
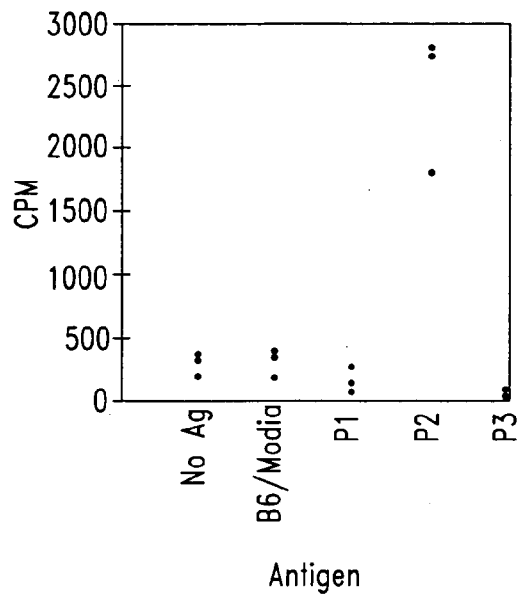
FIGS. 5A to 5C are graphs illustrating the stimulation of proliferative T cell responses in mice immunized with representative WT1 peptides. Thymidine incorporation assays were performed using one T cell line and two different clones, as indicated, and results were expressed as cpm. Controls indicated on the x axis were no antigen (No Ag) and B6/media; antigens used were p6–22 human (p1), p117–139 (p2) or p244–262 human (p3).
Figure 5B:
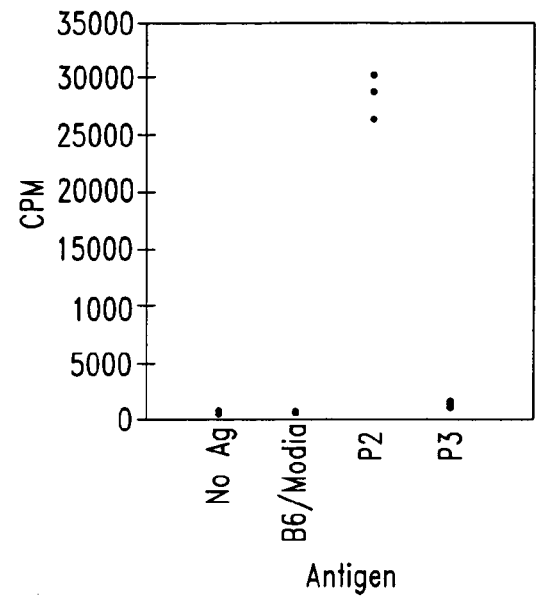
Figure 5C:
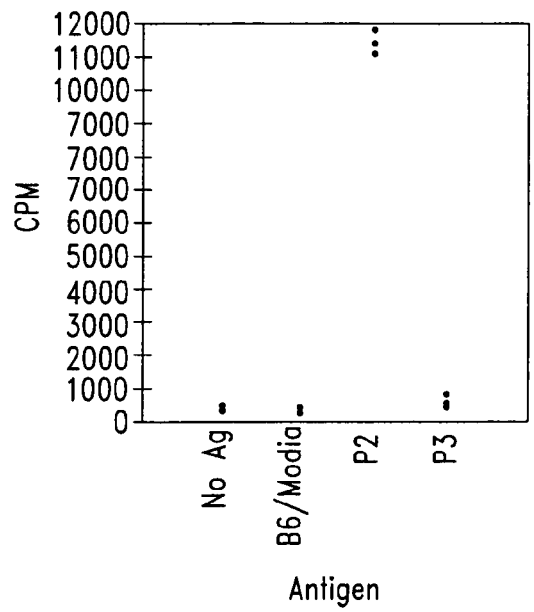

Immunization of mice with the group of peptides designated as Group A elicited an antibody response to WT1 (FIG. 4), and P117–139 elicited proliferative T cell responses (FIGS. 5A–5C). The stimulation indices (SI) varied between 8 and 72. Other peptides (P6–22 and P299–313) also were shown to elicit proliferative T cell responses. Immunization with P6–22 resulted in a stimulation index (SI) of 2.3 and immunization with P299–3 13 resulted in a SI of 3.3. Positive controls included ConA stimulated T cells, as well as T cells stimulated with known antigens, such as CD45 and FBL, and allogeneic T cell lines (DeBruijn et al., *Eur. J. Immunol.* 21:2963–2970, 1991).

These results show that vaccination with WT1 peptides can elicit antibody responses to WT1 protein and proliferative T cell responses to the immunizing peptides.

Example 4

Induction of CTL Responses in Mice Immunized with WT1 Peptides

This Example illustrates the ability of WT1 peptides to elicit CTL immunity.

Peptides (9-mers) with motifs appropriate for binding to class I MHC were identified using a BIMAS HLA peptide binding prediction analysis (Parker et al., *J. Immunol.* 152: 163, 1994). Peptides identified within such analyses are shown in Tables II–XLIV. In each of these tables, the score reflects the theoretical binding affinity (half-time of dissociation) of the peptide to the MHC molecule indicated.

Peptides identified using the Tsites program (Rothbard and Taylor, *EMBO J.* 7:93–100, 1988; Deavin et al., *Mol. Immunol.* 33:145–155, 1996), which searches for peptide motifs that have the potential to elicit Th responses are further shown in FIGS. 8A and 8B, and Table XLV.

TABLE II

Results of BIMAS HLA Peptide Binding Prediction Analysis for Binding of Human WT1 Peptides to Human HLA A1

| Rank | Start Position | Subsequence Residue Listing | Score (Estimate of Half Time of Disassociation of a Molecule Containing This Subsequence) |
|---|---|---|---|
| 1 | 137 | CLESQPAIR (SEQ ID NO:47) | 18.000 |
| 2 | 80 | GAEPHEEQC (SEQ ID NO:87) | 9.000 |
| 3 | 40 | FAPPGASAY (SEQ ID NO:74) | 5.000 |
| 4 | 354 | QCDFKDCER (SEQ ID NO:162) | 5.000 |
| 5 | 2 | GSDVRDLNA (SEQ ID NO:101) | 3.750 |
| 6 | 152 | VTFDGTPSY (SEQ ID NO:244) | 2.500 |
| 7 | 260 | WTEGQSNHS (SEQ ID NO:247) | 2.250 |
| 8 | 409 | TSEKPFSCR (SEQ ID NO:232) | 1.350 |
| 9 | 73 | KQEPSWGGA (SEQ ID NO:125) | 1.350 |
| 10 | 386 | KTCQRKFSR (SEQ ID NO:128) | 1.250 |
| 11 | 37 | VLDFAPPGA (SEQ ID NO:241) | 1.000 |
| 12 | 325 | CAYPGCNKR (SEQ ID NO:44) | 1.000 |
| 13 | 232 | QLECMTWNQ (SEQ ID NO:167) | 0.900 |
| 14 | 272 | ESDNHTTPI (SEQ ID NO:71) | 0.750 |
| 15 | 366 | RSDQLKRHQ (SEQ ID NO:193) | 0.750 |
| 16 | 222 | SSDNLYQMT (SEQ ID NO:217) | 0.750 |
| 17 | 427 | RSDELVRHH (SEQ ID NO:191) | 0.750 |
| 18 | 394 | RSDHLKTHT (SEQ ID NO:192) | 0.750 |
| 19 | 317 | TSEKRPFMC (SEQ ID NO:233) | 0.675 |
| 20 | 213 | QALLLRTPY (SEQ ID NO:160) | 0.500 |

TABLE III

Results of BIMAS HLA Peptide Binding Prediction Analysis for Binding of Human WT1 Peptides to Human HLA A 0201

| Rank | Start Position | Subsequence Residue Listing | Score (Estimate of Half Time of Disassociation of a Molecule Containing This Subsequence) |
|---|---|---|---|
| 1 | 126 | RMFPNAPYL (SEQ ID NO:185) | 313.968 |
| 2 | 187 | SLGEQQYSV (SEQ ID NO:214) | 285.163 |
| 3 | 10 | ALLPAVPSL (SEQ ID NO:34) | 181.794 |
| 4 | 242 | NLGATLKGV (SEQ ID NO:146) | 159.970 |
| 5 | 225 | NLYQMTSQL (SEQ ID NO:147) | 68.360 |
| 6 | 292 | GVFRGIQDV (SEQ ID NO:103) | 51.790 |
| 7 | 191 | QQYSVPPPV (SEQ ID NO:171) | 22.566 |
| 8 | 280 | ILCGAQYRI (SEQ ID NO:116) | 17.736 |
| 9 | 235 | CMTWNQMNL (SEQ ID NO:49) | 15.428 |
| 10 | 441 | NMTKLQLAL (SEQ ID NO:149) | 15.428 |
| 11 | 7 | DLNALLPAV (SEQ ID NO:58) | 11.998 |
| 12 | 227 | YQMTSQLEC (SEQ ID NO:251) | 8.573 |
| 13 | 239 | NQMNLGATL (SEQ ID NO:151) | 8.014 |
| 14 | 309 | TLVRSASET (SEQ ID NO:226) | 7.452 |
| 15 | 408 | KTSEKPFSC (SEQ ID NO:129) | 5.743 |
| 16 | 340 | LQMHSRKHT (SEQ ID NO:139) | 4.752 |
| 17 | 228 | QMTSQLECM (SEQ ID NO:169) | 4.044 |
| 18 | 93 | TVHFSGQFT (SEQ ID NO:235) | 3.586 |
| 19 | 37 | VLDFAPPGA (SEQ ID NO:241) | 3.378 |
| 20 | 86 | EQCLSAFTV (SEQ ID NO:69) | 3.068 |

TABLE IV

Results of BIMAS HLA Peptide Binding Prediction Analysis for Binding of Human WT1 Peptides to Human HLA A 0205

| Rank | Start Position | Subsequence Residue Listing | Score (Estimate of Half Time of Disassociation of a Molecule Containing This Subsequence) |
|---|---|---|---|
| 1 | 10 | ALLPAVPSL (SEQ ID NO:34) | 42.000 |
| 2 | 292 | GVFRGIQDV (SEQ ID NO:103) | 24.000 |
| 3 | 126 | RMFPNAPYL (SEQ ID NO:185) | 21.000 |
| 4 | 225 | NLYQMTSQL (SEQ ID NO:147) | 21.000 |
| 5 | 239 | NQMNLGATL (SEQ ID NO:151) | 16.800 |
| 6 | 302 | RVPGVAPTL (SEQ ID NO:195) | 14.000 |
| 7 | 441 | NMTKLQLAL (SEQ ID NO:149) | 7.000 |
| 8 | 235 | CMTWNQMNL (SEQ ID NO:49) | 7.000 |
| 9 | 187 | SLGEQQYSV (SEQ ID NO:214) | 6.000 |
| 10 | 191 | QQYSVPPPV (SEQ ID NO:171) | 4.800 |

TABLE IV-continued

Results of BIMAS HLA Peptide Binding Prediction Analysis for Binding of Human WT1 Peptides to Human HLA A 0205

| Rank | Start Position | Subsequence Residue Listing | Score (Estimate of Half Time of Disassociation of a Molecule Containing This Subsequence) |
|---|---|---|---|
| 11 | 340 | LQMHSRKHT (SEQ ID NO:139) | 4.080 |
| 12 | 242 | NLGATLKGV (SEQ ID NO:146) | 4.000 |
| 13 | 227 | YQMTSQLEC (SEQ ID NO:251) | 3.600 |
| 14 | 194 | SVPPPVYGC (SEQ ID NO:218) | 2.000 |
| 15 | 93 | TVHFSGQFT (SEQ ID NO:235) | 2.000 |
| 16 | 280 | ILCGAQYRI (SEQ ID NO:116) | 1.700 |
| 17 | 98 | GQFTGTAGA (SEQ ID NO:99) | 1.200 |
| 18 | 309 | TLVRSASET (SEQ ID NO:226) | 1.000 |
| 19 | 81 | AEPHEEQCL (SEQ ID NO:30) | 0.980 |
| 20 | 73 | KQEPSWGGA (SEQ ID NO:125) | 0.960 |

TABLE V

Results of BIMAS HLA Peptide Binding Prediction Analysis for Binding of Human WT1 Peptides to Human HLA A24

| Rank | Start Position | Subsequence Residue Listing | Score (Estimate of Half Time of Disassociation of a Molecule Containing This Subsequence) |
|---|---|---|---|
| 1 | 302 | RVPGVAPTL (SEQ ID NO:195) | 16.800 |
| 2 | 218 | RTPYSSDNL (SEQ ID NO:194) | 12.000 |
| 3 | 356 | DFKDCERRF (SEQ ID NO:55) | 12.000 |
| 4 | 126 | RMFPNAPYL (SEQ ID NO:185) | 9.600 |
| 5 | 326 | AYPGCNKRY (SEQ ID NO:42) | 7.500 |
| 6 | 270 | GYESDNHT (SEQ ID NO:106)T | 7.500 |
| 7 | 239 | NQMNLGATL (SEQ ID NO:151) | 7.200 |
| 8 | 10 | ALLPAVPSL (SEQ ID NO:34) | 7.200 |
| 9 | 130 | NAPYLPSCL (SEQ ID NO:144) | 7.200 |
| 10 | 329 | GCNKRYFKL (SEQ ID NO:90) | 6.600 |
| 11 | 417 | RWPSCQKKF (SEQ ID NO:196) | 6.600 |
| 12 | 47 | AYGSLGGPA (SEQ ID NO:41) | 6.000 |
| 13 | 180 | DPMGQQGSL (SEQ ID NO:59) | 6.000 |
| 14 | 4 | DVRDLNALL (SEQ ID NO:62) | 5.760 |
| 15 | 285 | QYRIHTHGV (SEQ ID NO:175) | 5.000 |
| 16 | 192 | QYSVPPPVY (SEQ ID NO:176) | 5.000 |
| 17 | 207 | DSCTGSQAL (SEQ ID NO:61) | 4.800 |
| 18 | 441 | NMTKLQLAL (SEQ ID NO:149) | 4.800 |
| 19 | 225 | NLYQMTSQL (SEQ ID NO:147) | 4.000 |
| 20 | 235 | CMTWNQMNL (SEQ ID NO:49) | 4.000 |

TABLE VI

Results of BIMAS HLA Peptide Binding Prediction Analysis for Binding of Human WT1 Peptides to Human HLA A3

| Rank | Start Position | Subsequence Residue Listing | Score (Estimate of Half Time of Disassociation of a Molecule Containing This Subsequence) |
|---|---|---|---|
| 1 | 436 | NMHQRNMTK (SEQ ID NO:148) | 40.000 |
| 2 | 240 | QMNLGATLK (SEQ ID NO:168) | 20.000 |
| 3 | 88 | CLSAFTVHF (SEQ ID NO:48) | 6.000 |
| 4 | 126 | RMFPNAPYL (SEQ ID NO:185) | 4.500 |
| 5 | 169 | AQFPNHSFK (SEQ ID NO:36) | 4.500 |
| 6 | 10 | ALLPAVPSL (SEQ ID NO:34) | 4.050 |
| 7 | 137 | CLESQPAIR (SEQ ID NO:47) | 4.000 |
| 8 | 225 | NLYQMTSQL (SEQ ID NO:147) | 3.000 |
| 9 | 32 | AQWAPVLDF (SEQ ID NO:37) | 2.700 |
| 10 | 280 | ILCGAQYRI (SEQ ID NO:116) | 2.700 |
| 11 | 386 | KTCQRKFSR (SEQ ID NO:128) | 1.800 |
| 12 | 235 | CMTWNQMNL (SEQ ID NO:49) | 1.200 |
| 13 | 441 | NMTKLQLAL (SEQ ID NO:149) | 1.200 |
| 14 | 152 | VTFDGTPSY (SEQ ID NO:244) | 1.000 |
| 15 | 187 | SLGEQQYSV (SEQ ID NO:214) | 0.900 |
| 16 | 383 | FQCKTCQRK (SEQ ID NO:80) | 0.600 |
| 17 | 292 | GVFRGIQDV (SEQ ID NO:103) | 0.450 |
| 18 | 194 | SVPPPVYGC (SEQ ID NO:218) | 0.405 |
| 19 | 287 | RIHTHGVFR (SEQ ID NO:182) | 0.400 |
| 20 | 263 | GQSNHSTGY (SEQ ID NO:100) | 0.360 |

TABLE VII

Results of BIMAS HLA Peptide Binding Prediction Analysis for Binding of Human WT1 Peptides to Human HLA A68.1

| Rank | Start Position | Subsequence Residue Listing | Score (Estimate of Half Time of Disassociation of a Molecule Containing This Subsequence) |
|---|---|---|---|
| 1 | 100 | FTGTAGACR (SEQ ID NO:84) | 100.000 |
| 2 | 386 | KTCQRKFSR (SEQ ID NO:128) | 50.000 |
| 3 | 368 | DQLKRHQRR (SEQ ID NO:60) | 30.000 |
| 4 | 312 | RSASETSEK (SEQ ID NO:190) | 18.000 |
| 5 | 337 | LSHLQMHSR (SEQ ID NO:141) | 15.000 |
| 6 | 364 | FSRSDQLKR (SEQ ID NO:83) | 15.000 |
| 7 | 409 | TSEKPFSCR (SEQ ID NO:232) | 15.000 |
| 8 | 299 | DVRRVPGVA (SEQ ID NO:63) | 12.000 |
| 9 | 4 | DVRDLNALL (SEQ ID NO:62) | 12.000 |
| 10 | 118 | SQASSGQAR (SEQ ID NO:216) | 10.000 |

TABLE VII-continued

Results of BIMAS HLA Peptide Binding Prediction Analysis for Binding of Human WT1 Peptides to Human HLA A68.1

| Rank | Start Position | Subsequence Residue Listing | Score (Estimate of Half Time of Disassociation of a Molecule Containing This Subsequence) |
|---|---|---|---|
| 11 | 343 | HSRKHTGEK (SEQ ID NO:111) | 9.000 |
| 12 | 169 | AQFPNHSFK (SEQ ID NO:36) | 9.000 |
| 13 | 292 | GVFRGIQDV (SEQ ID NO:103) | 8.000 |
| 14 | 325 | CAYPGCNKR (SEQ ID NO:44) | 7.500 |
| 15 | 425 | FARSDELVR (SEQ ID NO:75) | 7.500 |
| 16 | 354 | QCDFKDCER (SEQ ID NO:162) | 7.500 |
| 17 | 324 | MCAYPGCNK (SEQ ID NO:142) | 6.000 |
| 18 | 251 | AAGSSSSVK (SEQ ID NO:28) | 6.000 |
| 19 | 379 | GVKPFQCKT (SEQ ID NO:104) | 6.000 |
| 20 | 137 | CLESQPAIR (SEQ ID NO:47) | 5.000 |

TABLE VIII

Results of BIMAS HLA Peptide Binding Prediction Analysis for Binding of Human WT1 Peptides to Human HLA A 1101

| Rank | Start Position | Subsequence Residue Listing | Score (Estimate of Half Time of Disassociation of a Molecule Containing This Subsequence) |
|---|---|---|---|
| 1 | 386 | KTCQRKFSR (SEQ ID NO:128) | 1.800 |
| 2 | 169 | AQFPNHSFK (SEQ ID NO:36) | 1.200 |
| 3 | 436 | NMHQRNMTK (SEQ ID NO:148) | 0.800 |
| 4 | 391 | KFSRSDHLK (SEQ ID NO:120) | 0.600 |
| 5 | 373 | HQRRHTGVK (SEQ ID NO:109) | 0.600 |
| 6 | 383 | FQCKTCQRK (SEQ ID NO:80) | 0.600 |
| 7 | 363 | RFSRSDQLK (SEQ ID NO:178) | 0.600 |
| 8 | 240 | QMNLGATLK (SEQ ID NO:168) | 0.400 |
| 9 | 287 | RIHTHGVFR (SEQ ID NO:182) | 0.240 |
| 10 | 100 | FTGTAGACR (SEQ ID NO:84) | 0.200 |
| 11 | 324 | MCAYPGCNK (SEQ ID NO:142) | 0.200 |
| 12 | 251 | AAGSSSSVK (SEQ ID NO:28) | 0.200 |
| 13 | 415 | SCRWPSCQK (SEQ ID NO:201) | 0.200 |
| 14 | 118 | SQASSGQAR (SEQ ID NO:216) | 0.120 |
| 15 | 292 | GVFRGIQDV (SEQ ID NO:103) | 0.120 |
| 16 | 137 | CLESQPAIR (SEQ ID NO:47) | 0.080 |
| 17 | 425 | FARSDELVR (SEQ ID NO:75) | 0.080 |
| 18 | 325 | CAYPGCNKR (SEQ ID NO:44) | 0.080 |
| 19 | 312 | RSASETSEK (SEQ ID NO:190) | 0.060 |
| 20 | 65 | PPPPHSFIK (SEQ ID NO:156) | 0.060 |

TABLE IX

Results of BIMAS HLA Peptide Binding Prediction Analysis for Binding of Human WT1 Peptides to Human HLA A 3101

| Rank | Start Position | Subsequence Residue Listing | Score (Estimate of Half Time of Disassociation of a Molecule Containing This Subsequence) |
|---|---|---|---|
| 1 | 386 | KTCQRKFSR (SEQ ID NO:128) | 9.000 |
| 2 | 287 | RIHTHGVFR (SEQ ID NO:182) | 6.000 |
| 3 | 137 | CLESQPAIR (SEQ ID NO:47) | 2.000 |
| 4 | 118 | SQASSGQAR (SEQ ID NO:216) | 2.000 |
| 5 | 368 | DQLKRHQRR (SEQ ID NO:60) | 1.200 |
| 6 | 100 | FTGTAGACR (SEQ ID NO:84) | 1.000 |
| 7 | 293 | VFRGIQDVR (SEQ ID NO:238) | 0.600 |
| 8 | 325 | CAYPGCNKR (SEQ ID NO:44) | 0.600 |
| 9 | 169 | AQFPNHSFK (SEQ ID NO:36) | 0.600 |
| 10 | 279 | PILCGAQYR (SEQ ID NO:155) | 0.400 |
| 11 | 436 | NMHQRNMTK (SEQ ID NO:148) | 0.400 |
| 12 | 425 | FARSDELVR (SEQ ID NO:75) | 0.400 |
| 13 | 32 | AQWAPVLDF (SEQ ID NO:37) | 0.240 |
| 14 | 240 | QMNLGATLK (SEQ ID NO:168) | 0.200 |
| 15 | 354 | QCDFKDCER (SEQ ID NO:162) | 0.200 |
| 16 | 373 | HQRRHTGVK (SEQ ID NO:109) | 0.200 |
| 17 | 383 | FQCKTCQRK (SEQ ID NO:80) | 0.200 |
| 18 | 313 | SASETSEKR (SEQ ID NO:197) | 0.200 |
| 19 | 358 | KDCERRFSR (SEQ ID NO:118) | 0.180 |
| 20 | 391 | KFSRSDHLK (SEQ ID NO:120) | 0.180 |

TABLE X

Results of BIMAS HLA Peptide Binding Prediction Analysis for Binding of Human WT1 Peptides to Human HLA A 3302

| Rank | Start Position | Subsequence Residue Listing | Score (Estimate of Half Time of Disassociation of a Molecule Containing This Subsequence) |
|---|---|---|---|
| 1 | 337 | LSHLQMHSR (SEQ ID NO: 141) | 15.000 |
| 2 | 409 | TSEKPFSCR (SEQ ID NO: 232) | 15.000 |
| 3 | 364 | FSRSDQLKR (SEQ ID NO: 83) | 15.000 |

TABLE X-continued

Results of BIMAS HLA Peptide Binding Prediction Analysis for Binding of Human WT1 Peptides to Human HLA A 3302

| Rank | Start Position | Subsequence Residue Listing | Score (Estimate of Half Time of Disassociation of a Molecule Containing This Subsequence) |
|---|---|---|---|
| 4 | 137 | CLESQPAIR (SEQ ID NO: 47) | 9.000 |
| 5 | 368 | DQLKRHQRR (SEQ ID NO: 60) | 9.000 |
| 6 | 287 | RIHTHGVFR (SEQ ID NO: 182) | 4.500 |
| 7 | 210 | TGSQALLLR (SEQ ID NO: 223) | 3.000 |
| 8 | 425 | FARSDELVR (SEQ ID NO: 75) | 3.000 |
| 9 | 313 | SASETSEKR (SEQ ID NO: 197) | 3.000 |
| 10 | 293 | VFRGIQDVR (SEQ ID NO: 238) | 3.000 |
| 11 | 354 | QCDFKDCER (SEQ ID NO: 162) | 3.000 |
| 12 | 100 | FTGTAGACR (SEQ ID NO: 84) | 3.000 |
| 13 | 118 | SQASSGQAR (SEQ ID NO: 216) | 3.000 |
| 14 | 325 | CAYPGCNKR (SEQ ID NO: 44) | 3.000 |
| 15 | 207 | DSCTGSQAL (SEQ ID NO: 61) | 1.500 |
| 16 | 139 | ESQPAIRNQ (SEQ ID NO: 72) | 1.500 |
| 17 | 299 | DVRRVPGVA (SEQ ID NO: 63) | 1.500 |
| 18 | 419 | PSCQKKFAR (SEQ ID NO: 159) | 1.500 |
| 19 | 272 | ESDNHTTPI (SEQ ID NO: 71) | 1.500 |
| 20 | 4 | DVRDLNALL (SEQ ID NO: 62) | 1.500 |

TABLE XI

Results of BIMAS HLA Peptide Binding Prediction Analysis for Binding of Human WT1 Peptides to Human HLA B14

| Rank | Start Position | Subsequence Residue Listing | Score (Estimate of Half Time of Disassociation of a Molecule Containing This Subsequence) |
|---|---|---|---|
| 1 | 362 | RRFSRSDQL (SEQ ID NO: 187) | 1000.000 |
| 2 | 332 | KRYFKLSHL (SEQ ID NO: 127) | 300.000 |
| 3 | 423 | KKFARSDEL (SEQ ID NO: 122) | 150.000 |
| 4 | 390 | RKFSRSDHL (SEQ ID NO: 183) | 150.000 |
| 5 | 439 | QRNMTKLQL (SEQ ID NO: 173) | 20.000 |
| 6 | 329 | GCNKRYFKL (SEQ ID NO: 90) | 10.000 |
| 7 | 10 | ALLPAVPSL (SEQ ID NO: 34) | 10.000 |
| 8 | 180 | DPMGQQGSL (SEQ ID NO: 59) | 9.000 |
| 9 | 301 | RRVPGVAPT (SEQ ID NO: 189) | 6.000 |
| 10 | 126 | RMFPNAPYL (SEQ ID NO: 185) | 5.000 |
| 11 | 371 | KRHQRRHTG (SEQ ID NO: 126) | 5.000 |
| 12 | 225 | NLYQMTSQL (SEQ ID NO: 147) | 5.000 |
| 13 | 144 | IRNQGYSTV (SEQ ID NO: 117) | 4.000 |

TABLE XI-continued

Results of BIMAS HLA Peptide Binding Prediction Analysis for Binding of Human WT1 Peptides to Human HLA B14

| Rank | Start Position | Subsequence Residue Listing | Score (Estimate of Half Time of Disassociation of a Molecule Containing This Subsequence) |
|---|---|---|---|
| 14 | 429 | DELVRHHNM (SEQ ID NO: 53) | 3.000 |
| 15 | 437 | MHQRNMTKL (SEQ ID NO: 143) | 3.000 |
| 16 | 125 | ARMFPNAPY (SEQ ID NO: 38) | 3.000 |
| 17 | 239 | NQMNLGATL (SEQ ID NO: 151) | 3.000 |
| 18 | 286 | YRIHTHGVF (SEQ ID NO: 252) | 3.000 |
| 19 | 174 | HSFKHEDPM (SEQ ID NO: 110) | 3.000 |
| 20 | 372 | RHQRRHTGV (SEQ ID NO: 181) | 3.000 |

TABLE XII

Results of BIMAS HLA Peptide Binding Prediction Analysis for Binding of Human WT1 Peptides to Human HLA B40

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO: 30) | 40.000 |
| 2 | 429 | DELVRHHNM (SEQ ID NO: 53) | 24.000 |
| 3 | 410 | SEKPFSCRW (SEQ ID NO: 207) | 20.000 |
| 4 | 318 | SEKRPFMCA (SEQ ID NO: 208) | 15.000 |
| 5 | 233 | LECMTWNQM (SEQ ID NO: 131) | 12.000 |
| 6 | 3 | SDVRDLNAL (SEQ ID NO: 206) | 10.000 |
| 7 | 349 | GEKPYQCDF (SEQ ID NO: 91) | 8.000 |
| 8 | 6 | RDLNALLPA (SEQ ID NO: 177) | 5.000 |
| 9 | 85 | EEQCLSAFT (SEQ ID NO: 65) | 4.000 |
| 10 | 315 | SETSEKRPF (SEQ ID NO: 209) | 4.000 |
| 11 | 261 | TEGQSNHST (SEQ ID NO: 221) | 4.000 |
| 12 | 23 | GCALPVSGA (SEQ ID NO: 89) | 3.000 |
| 13 | 38 | LDFAPPGAS (SEQ ID NO: 130) | 3.000 |
| 14 | 273 | SDNHTTPIL (SEQ ID NO: 204) | 2.500 |
| 15 | 206 | TDSCTGSQA (SEQ ID NO: 220) | 2.500 |
| 16 | 24 | CALPVSGAA (SEQ ID NO: 43) | 2.000 |
| 17 | 98 | GQFTGTAGA (SEQ ID NO: 99) | 2.000 |
| 18 | 30 | GAAQWAPVL (SEQ ID NO: 86) | 2.000 |
| 19 | 84 | HEEQCLSAF (SEQ ID NO: 107) | 2.000 |

TABLE XII-continued

Results of BIMAS HLA Peptide Binding Prediction Analysis for Binding of Human WT1 Peptides to Human HLA B40

| Rank | Start Position | Subsequence Residue Listing | Score (Estimate of Half Time of Disassociation of a Molecule Containing This Subsequence) |
|---|---|---|---|
| 20 | 26 | LPVSGAAQW (SEQ ID NO: 138) | 2.000 |

TABLE XIII

Results of BIMAS HLA Peptide Binding Prediction Analysis for Binding of Human WT1 Peptides to Human HLA B60

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO: 30) | 160.000 |
| 2 | 3 | SDVRDLNAL (SEQ ID NO: 206) | 40.000 |
| 3 | 429 | DELVRHHNM (SEQ ID NO: 53) | 40.000 |
| 4 | 233 | LECMTWNQM (SEQ ID NO: 131) | 22.000 |
| 5 | 273 | SDNHTTPIL (SEQ ID NO: 204) | 20.000 |
| 6 | 209 | CTGSQALLL (SEQ ID NO: 52) | 8.000 |
| 7 | 30 | GAAQWAPVL (SEQ ID NO: 86) | 8.000 |
| 8 | 318 | SEKRPFMCA (SEQ ID NO: 208) | 8.000 |
| 9 | 180 | DPMGQQGSL (SEQ ID NO: 59) | 8.000 |
| 10 | 138 | LESQPAIRN (SEQ ID NO: 132) | 5.280 |
| 11 | 239 | NQMNLGATL (SEQ ID NO: 151) | 4.400 |
| 12 | 329 | GCNKRYFKL (SEQ ID NO: 90) | 4.400 |
| 13 | 130 | NAPYLPSCL (SEQ ID NO: 144) | 4.400 |
| 14 | 85 | EEQCLSAFT (SEQ ID NO: 65) | 4.400 |
| 15 | 208 | SCTGSQALL (SEQ ID NO: 202) | 4.000 |
| 16 | 207 | DSCTGSQAL (SEQ ID NO: 61) | 4.000 |
| 17 | 218 | RTPYSSDNL (SEQ ID NO: 194) | 4.000 |
| 18 | 261 | TEGQSNHST (SEQ ID NO: 221) | 4.000 |
| 19 | 18 | LGGGGGCAL (SEQ ID NO: 134) | 4.000 |
| 20 | 221 | YSSDNLYQM (SEQ ID NO: 253) | 2.200 |

TABLE XIV

Results of BIMAS HLA Peptide Binding Prediction Analysis for Binding of Human WT1 Peptides to Human HLA B61

| Rank | Start Position | Subsequence Residue Listing | Score (Estimate of Half Time of Disassociation of a Molecule Containing This Subsequence) |
|---|---|---|---|
| 1 | 318 | SEKRPFMCA (SEQ ID NO: 208) | 20.000 |
| 2 | 429 | DELVRHHNM (SEQ ID NO: 53) | 16.000 |
| 3 | 298 | QDVRRVPGV (SEQ ID NO: 164) | 10.000 |

TABLE XIV-continued

Results of BIMAS HLA Peptide Binding Prediction Analysis for Binding of Human WT1 Peptides to Human HLA B61

| Rank | Start Position | Subsequence Residue Listing | Score (Estimate of Half Time of Disassociation of a Molecule Containing This Subsequence) |
|---|---|---|---|
| 4 | 81 | AEPHEEQCL (SEQ ID NO: 30) | 8.000 |
| 5 | 233 | LECMTWNQM (SEQ ID NO: 131) | 8.000 |
| 6 | 6 | RDLNALLPA (SEQ ID NO: 177) | 5.500 |
| 7 | 85 | EEQCLSAFT (SEQ ID NO: 65) | 4.000 |
| 8 | 261 | TEGQSNHST (SEQ ID NO: 221) | 4.000 |
| 9 | 206 | TDSCTGSQA (SEQ ID NO: 220) | 2.500 |
| 10 | 295 | RGIQDVRRV (SEQ ID NO: 179) | 2.200 |
| 11 | 3 | SDVRDLNAL (SEQ ID NO: 206) | 2.000 |
| 12 | 250 | VAAGSSSSV (SEQ ID NO: 236) | 2.000 |
| 13 | 29 | SGAAQWAPV (SEQ ID NO: 211) | 2.000 |
| 14 | 315 | SETSEKRPF (SEQ ID NO: 209) | 1.600 |
| 15 | 138 | LESQPAIRN (SEQ ID NO: 132) | 1.200 |
| 16 | 244 | GATLKGVAA (SEQ ID NO: 88) | 1.100 |
| 17 | 20 | GGGGCALPV (SEQ ID NO: 92) | 1.100 |
| 18 | 440 | RNMTKLQLA (SEQ ID NO: 186) | 1.100 |
| 19 | 23 | GCALPVSGA (SEQ ID NO: 89) | 1.100 |
| 20 | 191 | QQYSVPPPV (SEQ ID NO: 171) | 1.000 |

TABLE XV

Results of BIMAS HLA Peptide Binding Prediction Analysis for Binding of Human WT1 Peptides to Human HLA B62

| Rank | Start Position | Subsequence Residue Listing | Score (Estimate of Half Time of Disassociation of a Molecule Containing This Subsequence) |
|---|---|---|---|
| 1 | 146 | NQGYSTVTF (SEQ ID NO: 150) | 211.200 |
| 2 | 32 | AQWAPVLDF (SEQ ID NO: 37) | 96.000 |
| 3 | 263 | GQSNHSTGY (SEQ ID NO: 100) | 96.000 |
| 4 | 88 | CLSAFTVHF (SEQ ID NO: 48) | 96.000 |
| 5 | 17 | SLGGGGGCA (SEQ ID NO: 215) | 9.600 |
| 6 | 239 | NQMNLGATL (SEQ ID NO: 151) | 8.800 |
| 7 | 191 | QQYSVPPPV (SEQ ID NO: 171) | 8.000 |
| 8 | 98 | GQFTGTAGA (SEQ ID NO: 99) | 8.000 |
| 9 | 384 | QCKTCQRKF (SEQ ID NO: 163) | 6.000 |
| 10 | 40 | FAPPGASAY (SEQ ID NO: 74) | 4.800 |
| 11 | 227 | YQMTSQLEC (SEQ ID NO: 251) | 4.800 |
| 12 | 187 | SLGEQQYSV (SEQ ID NO: 214) | 4.400 |

TABLE XV-continued

Results of BIMAS HLA Peptide Binding Prediction Analysis for Binding of Human WT1 Peptides to Human HLA B62

| Rank | Start Position | Subsequence Residue Listing | Score (Estimate of Half Time of Disassociation of a Molecule Containing This Subsequence) |
|---|---|---|---|
| 13 | 86 | EQCLSAFTV (SEQ ID NO: 69) | 4.400 |
| 14 | 152 | VTFDGTPSY (SEQ ID NO: 244) | 4.400 |
| 15 | 101 | TGTAGACRY (SEQ ID NO: 224) | 4.000 |
| 16 | 242 | NLGATLKGV (SEQ ID NO: 146) | 4.000 |
| 17 | 92 | FTVHFSGQF (SEQ ID NO: 85) | 4.000 |
| 18 | 7 | DLNALLPAV (SEQ ID NO: 58) | 4.000 |
| 19 | 123 | GQARMFPNA (SEQ ID NO: 98) | 4.000 |
| 20 | 280 | ILCGAQYRI (SEQ ID NO: 116) | 3.120 |

TABLE XVI

Results of BIMAS HLA Peptide Binding Prediction Analysis for Binding of Human WT1 Peptides to Human HLA B7

| Rank | Start Position | Subsequence Residue Listing | Score (Estimate of Half Time of Disassociation of a Molecule Containing This Subsequence) |
|---|---|---|---|
| 1 | 180 | DPMGQQGSL (SEQ ID NO: 59) | 240.000 |
| 2 | 4 | DVRDLNALL (SEQ ID NO: 62) | 200.000 |
| 3 | 302 | RVPGVAPTL (SEQ ID NO: 195) | 20.000 |
| 4 | 30 | GAAQWAPVL (SEQ ID NO: 86) | 12.000 |
| 5 | 239 | NQMNLGATL (SEQ ID NO: 151) | 12.000 |
| 6 | 130 | NAPYLPSCL (SEQ ID NO: 144) | 12.000 |
| 7 | 10 | ALLPAVPSL (SEQ ID NO: 34) | 12.000 |
| 8 | 299 | DVRRVPGVA (SEQ ID NO: 63) | 5.000 |
| 9 | 208 | SCTGSQALL (SEQ ID NO: 202) | 4.000 |
| 10 | 303 | VPGVAPTLV (SEQ ID NO: 242) | 4.000 |
| 11 | 18 | LGGGGGCAL (SEQ ID NO: 134) | 4.000 |
| 12 | 218 | RTPYSSDNL (SEQ ID NO: 194) | 4.000 |
| 13 | 207 | DSCTGSQAL (SEQ ID NO: 61) | 4.000 |
| 14 | 209 | CTGSQALLL (SEQ ID NO: 52) | 4.000 |
| 15 | 329 | GCNKRYFKL (SEQ ID NO: 90) | 4.000 |
| 16 | 235 | CMTWNQMNL (SEQ ID NO: 49) | 4.000 |
| 17 | 441 | NMTKLQLAL (SEQ ID NO: 149) | 4.000 |
| 18 | 126 | RMFPNAPYL (SEQ ID NO: 185) | 4.000 |
| 19 | 225 | NLYQMTSQL (SEQ ID NO: 147) | 4.000 |
| 20 | 143 | AIRNQGYST (SEQ ID NO: 33) | 3.000 |

TABLE XVII

Results of BIMAS HLA Peptide Binding Prediction Analysis for Binding of Human WT1 Peptides to Human HLA B8

| Rank | Start Position | Subsequence Residue Listing | Score (Estimate of Half Time of Disassociation of a Molecule Containing This Subsequence) |
|---|---|---|---|
| 1 | 329 | GCNKRYFKL (SEQ ID NO: 90) | 16.000 |
| 2 | 4 | DVRDLNALL (SEQ ID NO: 62) | 12.000 |
| 3 | 316 | ETSEKRPFM (SEQ ID NO: 73) | 3.000 |
| 4 | 180 | DPMGQQGSL (SEQ ID NO: 59) | 1.600 |
| 5 | 208 | SCTGSQALL (SEQ ID NO: 202) | 0.800 |
| 6 | 130 | NAPYLPSCL (SEQ ID NO: 144) | 0.800 |
| 7 | 244 | GATLKGVAA (SEQ ID NO: 88) | 0.800 |
| 8 | 30 | GAAQWAPVL (SEQ ID NO: 86) | 0.800 |
| 9 | 299 | DVRRVPGVA (SEQ ID NO: 63) | 0.400 |
| 10 | 420 | SCQKKFARS (SEQ ID NO: 200) | 0.400 |
| 11 | 387 | TCQRKFSRS (SEQ ID NO: 219) | 0.400 |
| 12 | 225 | NLYQMTSQL (SEQ ID NO: 147) | 0.400 |
| 13 | 141 | QPAIRNQGY (SEQ ID NO: 170) | 0.400 |
| 14 | 10 | ALLPAVPSL (SEQ ID NO: 34) | 0.400 |
| 15 | 207 | DSCTGSQAL (SEQ ID NO: 61) | 0.400 |
| 16 | 384 | QCKTCQRKF (SEQ ID NO: 163) | 0.400 |
| 17 | 136 | SCLESQPAI (SEQ ID NO: 198) | 0.300 |
| 18 | 347 | HTGEKPYQC (SEQ ID NO: 112) | 0.300 |
| 19 | 401 | HTRTHTGKT (SEQ ID NO: 114) | 0.200 |
| 20 | 332 | KRYFKLSHL (SEQ ID NO: 127) | 0.200 |

TABLE XVIII

Results of BIMAS HLA Peptide Binding Prediction Analysis for Binding of Human WT1 Peptides to Human HLA B 2702

| Rank | Start Position | Subsequence Residue Listing | Score (Estimate of Half Time of Disassociation of a Molecule Containing This Subsequence) |
|---|---|---|---|
| 1 | 332 | KRYFKLSHL (SEQ ID NO: 127) | 900.000 |
| 2 | 362 | RRFSRSDQL (SEQ ID NO: 187) | 900.000 |
| 3 | 286 | YRIHTHGVF (SEQ ID NO: 252) | 200.000 |
| 4 | 125 | ARMFPNAPY (SEQ ID NO: 38) | 200.000 |
| 5 | 375 | RRHTGVKPF (SEQ ID NO: 188) | 180.000 |
| 6 | 32 | AQWAPVLDF (SEQ ID NO: 37) | 100.000 |
| 7 | 301 | RRVPGVAPT (SEQ ID NO: 189) | 60.000 |
| 8 | 439 | QRNMTKLQL (SEQ ID NO: 173) | 60.000 |
| 9 | 126 | RMFPNAPYL (SEQ ID NO: 185) | 22.500 |
| 10 | 426 | ARSDELVRH (SEQ ID NO: 39) | 20.000 |

TABLE XVIII-continued

Results of BIMAS HLA Peptide Binding Prediction Analysis for Binding of Human WT1 Peptides to Human HLA B 2702

| Rank | Start Position | Subsequence Residue Listing | Score (Estimate of Half Time of Disassociation of a Molecule Containing This Subsequence) |
|---|---|---|---|
| 11 | 146 | NQGYSTVTF (SEQ ID NO: 150) | 20.000 |
| 12 | 144 | IRNQGYSTV (SEQ ID NO: 117) | 20.000 |
| 13 | 389 | QRKFSRSDH (SEQ ID NO: 172) | 20.000 |
| 14 | 263 | GQSNHSTGY (SEQ ID NO: 100) | 20.000 |
| 15 | 416 | CRWPSCQKK (SEQ ID NO: 50) | 20.000 |
| 16 | 191 | QQYSVPPPV (SEQ ID NO: 171) | 10.000 |
| 17 | 217 | LRTPYSSDN (SEQ ID NO: 140) | 10.000 |
| 18 | 107 | CRYGPFGPP (SEQ ID NO: 51) | 10.000 |
| 19 | 98 | GQFTGTAGA (SEQ ID NO: 99) | 10.000 |
| 20 | 239 | NQMNLGATL (SEQ ID NO: 151) | 6.000 |

TABLE XIX

Results of BIMAS HLA Peptide Binding Prediction Analysis for Binding of Human WT1 Peptides to Human HLA B 2705

| Rank | Start Position | Subsequence Residue Listing | Score (Estimate of Half Time of Disassociation of a Molecule Containing This Subsequence) |
|---|---|---|---|
| 1 | 332 | KRYFKLSHL (SEQ ID NO: 127) | 30000.000 |
| 2 | 362 | RRFSRSDQL (SEQ ID NO: 187) | 30000.000 |
| 3 | 416 | CRWPSCQKK (SEQ ID NO: 50) | 10000.000 |
| 4 | 439 | QRNMTKLQL (SEQ ID NO: 173) | 2000.000 |
| 5 | 286 | YRIHTHGVF (SEQ ID NO: 252) | 1000.000 |
| 6 | 125 | ARMFPNAPY (SEQ ID NO: 38) | 1000.000 |
| 7 | 294 | FRGIQDVRR (SEQ ID NO: 81) | 1000.000 |
| 8 | 432 | VRHHNMHQR (SEQ ID NO: 243) | 1000.000 |
| 9 | 169 | AQFPNHSFK (SEQ ID NO: 36) | 1000.000 |
| 10 | 375 | RRHTGVKPF (SEQ ID NO: 188) | 900.000 |
| 11 | 126 | RMFPNAPYL (SEQ ID NO: 185) | 750.000 |
| 12 | 144 | IRNQGYSTV (SEQ ID NO: 117) | 600.000 |
| 13 | 301 | RRVPGVAPT (SEQ ID NO: 189) | 600.000 |
| 14 | 32 | AQWAPVLDF (SEQ ID NO: 37) | 500.000 |
| 15 | 191 | QQYSVPPPV (SEQ ID NO: 171) | 300.000 |
| 16 | 373 | HQRRHTGVK (SEQ ID NO: 109) | 200.000 |
| 17 | 426 | ARSDELVRH (SEQ ID NO: 39) | 200.000 |
| 18 | 383 | FQCKTCQRK (SEQ ID NO: 80) | 200.000 |
| 19 | 239 | NQMNLGATL (SEQ ID NO: 151) | 200.000 |
| 20 | 389 | QRKFSRSDH (SEQ ID NO: 172) | 200.000 |

TABLE XX

Results of BIMAS HLA Peptide Binding Prediction Analysis for Binding of Human WT1 Peptides to Human HLA B 3501

| Rank | Start Position | Subsequence Residue Listing | Score (Estimate of Half Time of Disassociation of a Molecule Containing This Subsequence) |
|---|---|---|---|
| 1 | 278 | TPILCGAQY (SEQ ID NO: 227) | 40.000 |
| 2 | 141 | QPAIRNQGY (SEQ ID NO: 170) | 40.000 |
| 3 | 219 | TPYSSDNLY (SEQ ID NO: 231) | 40.000 |
| 4 | 327 | YPGCNKRYF (SEQ ID NO: 250) | 20.000 |
| 5 | 163 | TPSHHAAQF (SEQ ID NO: 228) | 20.000 |
| 6 | 180 | DPMGQQGSL (SEQ ID NO: 59) | 20.000 |
| 7 | 221 | YSSDNLYQM (SEQ ID NO: 253) | 20.000 |
| 8 | 26 | LPVSGAAQW (SEQ ID NO: 138) | 10.000 |
| 9 | 174 | HSFKHEDPM (SEQ ID NO: 110) | 10.000 |
| 10 | 82 | EPHEEQCLS (SEQ ID NO: 68) | 6.000 |
| 11 | 213 | QALLLRTPY (SEQ ID NO: 160) | 6.000 |
| 12 | 119 | QASSGQARM (SEQ ID NO: 161) | 6.000 |
| 13 | 4 | DVRDLNALL (SEQ ID NO: 62) | 6.000 |
| 14 | 40 | FAPPGASAY (SEQ ID NO: 74) | 6.000 |
| 15 | 120 | ASSGQARMF (SEQ ID NO: 40) | 5.000 |
| 16 | 207 | DSCTGSQAL (SEQ ID NO: 61) | 5.000 |
| 17 | 303 | VPGVAPTLV (SEQ ID NO: 242) | 4.000 |
| 18 | 316 | ETSEKRPFM (SEQ ID NO: 73) | 4.000 |
| 19 | 152 | VTFDGTPSY (SEQ ID NO: 244) | 4.000 |
| 20 | 412 | KPFSCRWPS (SEQ ID NO: 123) | 4.000 |

TABLE XXI

Results of BIMAS HLA Peptide Binding Prediction Analysis for Binding of Human WT1 Peptides to Human HLA B 3701

| Rank | Start Position | Subsequence Residue Listing | Score (Estimate of Half Time of Disassociation of a Molecule Containing This Subsequence) |
|---|---|---|---|
| 1 | 3 | SDVRDLNAL (SEQ ID NO: 206) | 40.000 |
| 2 | 273 | SDNHTTPIL (SEQ ID NO: 204) | 40.000 |
| 3 | 81 | AEPHEEQCL (SEQ ID NO: 30) | 10.000 |

TABLE XXI-continued

Results of BIMAS HLA Peptide Binding Prediction Analysis for Binding of Human WT1 Peptides to Human HLA B 3701

| Rank | Start Position | Subsequence Residue Listing | Score (Estimate of Half Time of Disassociation of a Molecule Containing This Subsequence) |
|---|---|---|---|
| 4 | 298 | QDVRRVPGV (SEQ ID NO: 164) | 8.000 |
| 5 | 428 | SDELVRHHN (SEQ ID NO: 203) | 6.000 |
| 6 | 85 | EEQCLSAFT (SEQ ID NO: 65) | 5.000 |
| 7 | 208 | SCTGSQALL (SEQ ID NO: 202) | 5.000 |
| 8 | 4 | DVRDLNALL (SEQ ID NO: 62) | 5.000 |
| 9 | 209 | CTGSQALLL (SEQ ID NO: 52) | 5.000 |
| 10 | 38 | LDFAPPGAS (SEQ ID NO: 130) | 4.000 |
| 11 | 223 | SDNLYQMTS (SEQ ID NO: 205) | 4.000 |
| 12 | 179 | EDPMGQQGS (SEQ ID NO: 64) | 4.000 |
| 13 | 206 | TDSCTGSQA (SEQ ID NO: 220) | 4.000 |
| 14 | 6 | RDLNALLPA (SEQ ID NO: 177) | 4.000 |
| 15 | 84 | HEEQCLSAF (SEQ ID NO: 107) | 2.000 |
| 16 | 233 | LECMTWNQM (SEQ ID NO: 131) | 2.000 |
| 17 | 429 | DELVRHHNM (SEQ ID NO: 53) | 2.000 |
| 18 | 315 | SETSEKRPF (SEQ ID NO: 209) | 2.000 |
| 19 | 349 | GEKPYQCDF (SEQ ID NO: 91) | 2.000 |
| 20 | 302 | RVPGVAPTL (SEQ ID NO: 195) | 1.500 |

TABLE XXII

Results of BIMAS HLA Peptide Binding Prediction Analysis for Binding of Human WT1 Peptides to Human HLA B 3801

| Rank | Start Position | Subsequence Residue Listing | Score (Estimate of Half Time of Disassociation of a Molecule Containing This Subsequence) |
|---|---|---|---|
| 1 | 437 | MHQRNMTKL (SEQ ID NO: 143) | 36.000 |
| 2 | 434 | HHNMHQRNM (SEQ ID NO: 108) | 6.000 |
| 3 | 372 | RHQRRHTGV (SEQ ID NO: 181) | 6.000 |
| 4 | 180 | DPMGQQGSL (SEQ ID NO: 59) | 4.000 |
| 5 | 433 | RHHNMHQRN (SEQ ID NO: 180) | 3.900 |
| 6 | 165 | SHHAAQFPN (SEQ ID NO: 213) | 3.900 |
| 7 | 202 | CHTPTDSCT (SEQ ID NO: 45) | 3.000 |
| 8 | 396 | DHLKTHTRT (SEQ ID NO: 57) | 3.000 |
| 9 | 161 | GHTPSHHAA (SEQ ID NO: 94) | 3.000 |
| 10 | 302 | RVPGVAPTL (SEQ ID NO: 195) | 2.600 |
| 11 | 417 | RWPSCQKKF (SEQ ID NO: 196) | 2.400 |
| 12 | 327 | YPGCNKRYF (SEQ ID NO: 250) | 2.400 |
| 13 | 208 | SCTGSQALL (SEQ ID NO: 202) | 2.000 |

TABLE XXII-continued

Results of BIMAS HLA Peptide Binding Prediction Analysis for Binding of Human WT1 Peptides to Human HLA B 3801

| Rank | Start Position | Subsequence Residue Listing | Score (Estimate of Half Time of Disassociation of a Molecule Containing This Subsequence) |
|---|---|---|---|
| 14 | 163 | TPSHHAAQF (SEQ ID NO: 228) | 2.000 |
| 15 | 120 | ASSGQARMF (SEQ ID NO: 40) | 2.000 |
| 16 | 18 | LGGGGGCAL (SEQ ID NO: 134) | 2.000 |
| 17 | 177 | KHEDPMGQQ (SEQ ID NO: 121) | 1.800 |
| 18 | 83 | PHEEQCLSA (SEQ ID NO: 154) | 1.800 |
| 19 | 10 | ALLPAVPSL (SEQ ID NO: 34) | 1.300 |
| 20 | 225 | NLYQMTSQL (SEQ ID NO: 147) | 1.300 |

TABLE XXIII

Results of BIMAS HLA Peptide Binding Prediction Analysis for Binding of Human WT1 Peptides to Human HLA B 3901

| Rank | Start Position | Subsequence Residue Listing | Score (Estimate of Half Time of Disassociation of a Molecule Containing This Subsequence) |
|---|---|---|---|
| 1 | 437 | MHQRNMTKL (SEQ ID NO: 143) | 135.000 |
| 2 | 332 | KRYFKLSHL (SEQ ID NO: 127) | 45.000 |
| 3 | 434 | HHNMHQRNM (SEQ ID NO: 108) | 30.000 |
| 4 | 362 | RRFSRSDQL (SEQ ID NO: 187) | 30.000 |
| 5 | 372 | RHQRRHTGV (SEQ ID NO: 181) | 30.000 |
| 6 | 10 | ALLPAVPSL (SEQ ID NO: 34) | 9.00 |
| 7 | 439 | QRNMTKLQL (SEQ ID NO: 173) | 7.500 |
| 8 | 390 | RKFSRSDHL (SEQ ID NO: 183) | 6.000 |
| 9 | 396 | DHLKTHTRT (SEQ ID NO: 57) | 6.000 |
| 10 | 239 | NQMNLGATL (SEQ ID NO: 151) | 6.000 |
| 11 | 423 | KKFARSDEL (SEQ ID NO: 122) | 6.000 |
| 12 | 126 | RMFPNAPYL (SEQ ID NO: 185) | 6.000 |
| 13 | 225 | NLYQMTSQL (SEQ ID NO: 147) | 6.000 |
| 14 | 180 | DPMGQQGSL (SEQ ID NO: 59) | 6.000 |
| 15 | 144 | IRNQGYSTV (SEQ ID NO: 117) | 5.000 |
| 16 | 136 | SCLESQPAI (SEQ ID NO: 198) | 4.000 |
| 17 | 292 | GVFRGIQDV (SEQ ID NO: 103) | 3.000 |
| 18 | 302 | RVPGVAPTL (SEQ ID NO: 195) | 3.000 |
| 19 | 208 | SCTGSQALL (SEQ ID NO: 202) | 3.000 |
| 20 | 207 | DSCTGSQAL (SEQ ID NO: 61) | 3.000 |

TABLE XXIV

Results of BIMAS HLA Peptide Binding Prediction Analysis for Binding of Human WT1 Peptides to Human HLA B 3902

| Rank | Start Position | Subsequence Residue Listing | Score (Estimate of Half Time of Disassociation of a Molecule Containing This Subsequence) |
|---|---|---|---|
| 1 | 239 | NQMNLGATL (SEQ ID NO: 151) | 24.000 |
| 2 | 390 | RKFSRSDHL (SEQ ID NO: 183) | 20.000 |
| 3 | 423 | KKFARSDEL (SEQ ID NO: 122) | 20.000 |
| 4 | 32 | AQWAPVLDF (SEQ ID NO: 37) | 5.000 |
| 5 | 146 | NQGYSTVTF (SEQ ID NO: 150) | 5.000 |
| 6 | 130 | NAPYLPSCL (SEQ ID NO: 144) | 2.400 |
| 7 | 225 | NLYQMTSQL (SEQ ID NO: 147) | 2.400 |
| 8 | 30 | GAAQWAPVL (SEQ ID NO: 86) | 2.400 |
| 9 | 441 | NMTKLQLAL (SEQ ID NO: 149) | 2.400 |
| 10 | 302 | RVPGVAPTL (SEQ ID NO: 195) | 2.400 |
| 11 | 126 | RMFPNAPYL (SEQ ID NO: 185) | 2.000 |
| 12 | 218 | RTPYSSDNL (SEQ ID NO: 194) | 2.000 |
| 13 | 209 | CTGSQALLL (SEQ ID NO: 52) | 2.000 |
| 14 | 332 | KRYFKLSHL (SEQ ID NO: 127) | 2.000 |
| 15 | 180 | DPMGQQGSL (SEQ ID NO: 59) | 2.000 |
| 16 | 437 | MHQRNMTKL (SEQ ID NO: 143) | 2.000 |
| 17 | 207 | DSCTGSQAL (SEQ ID NO: 61) | 2.000 |
| 18 | 208 | SCTGSQALL (SEQ ID NO: 202) | 2.000 |
| 19 | 329 | GCNKRYFKL (SEQ ID NO: 90) | 2.000 |
| 20 | 10 | ALLPAVPSL (SEQ ID NO: 34) | 2.000 |

TABLE XXV

Results of BIMAS HLA Peptide Binding Prediction Analysis for Binding of Human WT1 Peptides to Human HLA B 4403

| Rank | Start Position | Subsequence Residue Listing | Score (Estimate of Half Time of Disassociation of a Molecule Containing This Subsequence) |
|---|---|---|---|
| 1 | 315 | SETSEKRPF (SEQ ID NO: 209) | 80.000 |
| 2 | 349 | GEKPYQCDF (SEQ ID NO: 91) | 80.000 |
| 3 | 84 | HEEQCLSAF (SEQ ID NO: 107) | 60.000 |
| 4 | 410 | SEKPFSCRW (SEQ ID NO: 207) | 48.000 |
| 5 | 429 | DELVRHHNM (SEQ ID NO: 53) | 24.000 |
| 6 | 278 | TPILCGAQY (SEQ ID NO: 227) | 15.000 |
| 7 | 141 | QPAIRNQGY (SEQ ID NO: 170) | 9.000 |
| 8 | 40 | FAPPGASAY (SEQ ID NO: 74) | 9.000 |
| 9 | 213 | QALLLRTPY (SEQ ID NO: 160) | 9.000 |
| 10 | 318 | SEKRPFMCA (SEQ ID NO: 208) | 8.000 |
| 11 | 81 | AEPHEEQCL (SEQ ID NO: 30) | 8.000 |
| 12 | 152 | VTFDGTPSY (SEQ ID NO: 244) | 4.500 |
| 13 | 101 | TGTAGACRY (SEQ ID NO: 224) | 4.500 |
| 14 | 120 | ASSGQARMF (SEQ ID NO: 40) | 4.500 |
| 15 | 261 | TEGQSNHST (SEQ ID NO: 221) | 4.000 |
| 16 | 85 | EEQCLSAFT (SEQ ID NO: 65) | 4.000 |
| 17 | 233 | LECMTWNQM (SEQ ID NO: 131) | 4.000 |
| 18 | 104 | AGACRYGPF (SEQ ID NO: 31) | 4.000 |
| 19 | 3 | SDVRDLNAL (SEQ ID NO: 206) | 3.000 |
| 20 | 185 | QGSLGEQQY (SEQ ID NO: 166) | 3.000 |

TABLE XXVI

Results of BIMAS HLA Peptide Binding Prediction Analysis for Binding of Human WT1 Peptides to Human HLA B 5101

| Rank | Start Position | Subsequence Residue Listing | Score (Estimate of Half Time of Disassociation of a Molecule Containing This Subsequence) |
|---|---|---|---|
| 1 | 303 | VPGVAPTLV (SEQ ID NO: 242) | 314.600 |
| 2 | 180 | DPMGQQGSL (SEQ ID NO: 59) | 242.000 |
| 3 | 250 | VAAGSSSSV (SEQ ID NO: 236) | 157.300 |
| 4 | 130 | NAPYLPSCL (SEQ ID NO: 144) | 50.000 |
| 5 | 30 | GAAQWAPVL (SEQ ID NO: 86) | 50.000 |
| 6 | 20 | GGGGCALPV (SEQ ID NO: 92) | 44.000 |
| 7 | 64 | PPPPPHSFI (SEQ ID NO: 157) | 40.000 |
| 8 | 29 | SGAAQWAPV (SEQ ID NO: 211) | 40.000 |
| 9 | 18 | LGGGGGCAL (SEQ ID NO: 134) | 31.460 |
| 10 | 295 | RGIQDVRRV (SEQ ID NO: 179) | 22.000 |
| 11 | 119 | QASSGQARM (SEQ ID NO: 161) | 18.150 |
| 12 | 418 | WPSCQKKFA (SEQ ID NO: 246) | 12.100 |
| 13 | 82 | EPHEEQCLS (SEQ ID NO: 68) | 12.100 |
| 14 | 110 | GPFGPPPPS (SEQ ID NO: 96) | 11.000 |
| 15 | 272 | ESDNHTTPI (SEQ ID NO: 71) | 8.000 |

TABLE XXVI-continued

Results of BIMAS HLA Peptide Binding Prediction Analysis for Binding of Human WT1 Peptides to Human HLA B 5101

| Rank | Start Position | Subsequence Residue Listing | Score (Estimate of Half Time of Disassociation of a Molecule Containing This Subsequence) |
|---|---|---|---|
| 16 | 306 | VAPTLVRSA (SEQ ID NO: 237) | 7.150 |
| 17 | 280 | ILCGAQYRI (SEQ ID NO: 116) | 6.921 |
| 18 | 219 | TPYSSDNLY (SEQ ID NO: 231) | 6.600 |
| 19 | 128 | FPNAPYLPS (SEQ ID NO: 79) | 6.500 |
| 20 | 204 | TPTDSCTGS (SEQ ID NO: 230) | 6.050 |

TABLE XXVII

Results of BIMAS HLA Peptide Binding Prediction Analysis for Binding of Human WT1 Peptides to Human HLA B 5102

| Rank | Start Position | Subsequence Residue Listing | Score (Estimate of Half Time of Disassociation of a Molecule Containing This Subsequence) |
|---|---|---|---|
| 1 | 295 | RGIQDVRRV (SEQ ID NO: 179) | 290.400 |
| 2 | 303 | VPGVAPTLV (SEQ ID NO: 242) | 200.000 |
| 3 | 180 | DPMGQQGSL (SEQ ID NO: 59) | 133.100 |
| 4 | 250 | VAAGSSSSV (SEQ ID NO: 236) | 110.000 |
| 5 | 30 | GAAQWAPVL (SEQ ID NO: 86) | 55.000 |
| 6 | 130 | NAPYLPSCL (SEQ ID NO: 144) | 50.000 |
| 7 | 20 | GGGGCALPV (SEQ ID NO: 92) | 44.000 |
| 8 | 29 | SGAAQWAPV (SEQ ID NO: 211) | 44.000 |
| 9 | 64 | PPPPPHSFI (SEQ ID NO: 157) | 40.000 |
| 10 | 119 | QASSGQARM (SEQ ID NO: 161) | 36.300 |
| 11 | 110 | GPFGPPPPS (SEQ ID NO: 96) | 27.500 |
| 12 | 412 | KPFSCRWPS (SEQ ID NO: 123) | 25.000 |
| 13 | 18 | LGGGGGCAL (SEQ ID NO: 134) | 24.200 |
| 14 | 24 | CALPVSGAA (SEQ ID NO: 43) | 16.500 |
| 15 | 219 | TPYSSDNLY (SEQ ID NO: 231) | 15.000 |
| 16 | 292 | GVFRGIQDV (SEQ ID NO: 103) | 14.641 |
| 17 | 136 | SCLESQPAI (SEQ ID NO: 198) | 14.520 |
| 18 | 418 | WPSCQKKFA (SEQ ID NO: 246) | 12.100 |
| 19 | 269 | TGYESDNHT (SEQ ID NO: 225) | 11.000 |
| 20 | 351 | KPYQCDFKD (SEQ ID NO: 124) | 11.000 |

TABLE XXVIII

Results of BIMAS HLA Peptide Binding Prediction Analysis for Binding of Human WT1 Peptides to Human HLA B 5201

| Rank | Start Position | Subsequence Residue Listing | Score (Estimate of Half Time of Disassociation of a Molecule Containing This Subsequence) |
|---|---|---|---|
| 1 | 191 | QQYSVPPPV (SEQ ID NO: 171) | 100.000 |
| 2 | 32 | AQWAPVLDF (SEQ ID NO: 37) | 30.000 |
| 3 | 243 | LGATLKGVA (SEQ ID NO: 133) | 16.500 |
| 4 | 303 | VPGVAPTLV (SEQ ID NO: 242) | 13.500 |
| 5 | 86 | EQCLSAFTV (SEQ ID NO: 69) | 12.000 |
| 6 | 295 | RGIQDVRRV (SEQ ID NO: 179) | 10.000 |
| 7 | 98 | GQFTGTAGA (SEQ ID NO: 99) | 8.250 |
| 8 | 292 | GVFRGIQDV (SEQ ID NO: 103) | 8.250 |
| 9 | 29 | SGAAQWAPV (SEQ ID NO: 211) | 6.000 |
| 10 | 146 | NQGYSTVTF (SEQ ID NO: 150) | 5.500 |
| 11 | 20 | GGGGCALPV (SEQ ID NO: 92) | 5.000 |
| 12 | 239 | NQMNLGATL (SEQ ID NO: 151) | 4.000 |
| 13 | 64 | PPPPPHSFI (SEQ ID NO: 157) | 3.600 |
| 14 | 273 | SDNHTTPIL (SEQ ID NO: :204) | 3.300 |
| 15 | 286 | YRIHTHGVF (SEQ ID NO: 252) | 3.000 |
| 16 | 269 | TGYESDNHT (SEQ ID NO: 225) | 3.000 |
| 17 | 406 | TGKTSEKPF (SEQ ID NO: 222) | 2.750 |
| 18 | 327 | YPGCNKRYF (SEQ ID NO: 250) | 2.750 |
| 19 | 7 | DLNALLPAV (SEQ ID NO: 58) | 2.640 |
| 20 | 104 | AGACRYGPF (SEQ ID NO: 31) | 2.500 |

TABLE XXIX

Results of BIMAS HLA Peptide Binding Prediction Analysis for Binding of Human WT1 Peptides to Human HLA B 5801

| Rank | Start Position | Subsequence Residue Listing | Score (Estimate of Half Time of Disassociation of a Molecule Containing This Subsequence) |
|---|---|---|---|
| 1 | 230 | TSQLECMTW (SEQ ID NO: 234) | 96.800 |
| 2 | 92 | FTVHFSGQF (SEQ ID NO: 85) | 60.000 |
| 3 | 120 | ASSGQARMF (SEQ ID NO: 40) | 40.000 |
| 4 | 168 | AAQFPNHSF (SEQ ID NO: 29) | 20.000 |
| 5 | 408 | KTSEKPFSC (SEQ ID NO: 129) | 12.000 |
| 6 | 394 | RSDHLKTHT (SEQ ID NO: 192) | 9.900 |
| 7 | 276 | HTTPILCGA (SEQ ID NO: 115) | 7.200 |

TABLE XXIX-continued

Results of BIMAS HLA Peptide Binding Prediction Analysis for Binding of Human WT1 Peptides to Human HLA B 5801

| Rank | Start Position | Subsequence Residue Listing | Score (Estimate of Half Time of Disassociation of a Molecule Containing This Subsequence) |
|---|---|---|---|
| 8 | 218 | RTPYSSDNL (SEQ ID NO: 194) | 6.600 |
| 9 | 152 | VTFDGTPSY (SEQ ID NO: 244) | 6.000 |
| 10 | 40 | FAPPGASAY (SEQ ID NO: 74) | 6.000 |
| 11 | 213 | QALLLRTPY (SEQ ID NO: 160) | 4.500 |
| 12 | 347 | HTGEKPYQC (SEQ ID NO: 112) | 4.400 |
| 13 | 252 | AGSSSSVKW (SEQ ID NO: 32) | 4.400 |
| 14 | 211 | GSQALLLRT (SEQ ID NO: 102) | 4.356 |
| 15 | 174 | HSFKHEDPM (SEQ ID NO: 110) | 4.000 |
| 16 | 317 | TSEKRPFMC (SEQ ID NO: 233) | 4.000 |
| 17 | 26 | LPVSGAAQW (SEQ ID NO: 138) | 4.000 |
| 18 | 289 | HTHGVFRGI (SEQ ID NO: 113) | 3.600 |
| 19 | 222 | SSDNLYQMT (SEQ ID NO: 217) | 3.300 |
| 20 | 96 | FSGQFTGTA (SEQ ID NO: 82) | 3.300 |

TABLE XXX

Results of BIMAS HLA Peptide Binding Prediction Analysis for Binding of Human WT1 Peptides to Human HLA CW0301

| Rank | Start Position | Subsequence Residue Listing | Score (Estimate of Half Time of Disassociation of a Molecule Containing This Subsequence) |
|---|---|---|---|
| 1 | 10 | ALLPAVPSL (SEQ ID NO: 34) | 100.000 |
| 2 | 332 | KRYFKLSHL (SEQ ID NO: 127) | 48.000 |
| 3 | 126 | RMFPNAPYL (SEQ ID NO: 185) | 36.000 |
| 4 | 3 | SDVRDLNAL (SEQ ID NO: 206) | 30.000 |
| 5 | 239 | NQMNLGATL (SEQ ID NO: 151) | 24.000 |
| 6 | 225 | NLYQMTSQL (SEQ ID NO: 147) | 24.000 |
| 7 | 180 | DPMGQQGSL (SEQ ID NO: 59) | 20.000 |
| 8 | 362 | RRFSRSDQL (SEQ ID NO: 187) | 12.000 |
| 9 | 329 | GCNKRYFKL (SEQ ID NO: 90) | 10.000 |
| 10 | 286 | YRIHTHGVF (SEQ ID NO: 252) | 10.000 |
| 11 | 301 | RRVPGVAPT (SEQ ID NO: 189) | 10.000 |
| 12 | 24 | CALPVSGAA (SEQ ID NO: 43) | 10.000 |
| 13 | 136 | SCLESQPAI (SEQ ID NO: 198) | 7.500 |
| 14 | 437 | MHQRNMTKL (SEQ ID NO: 143) | 7.200 |

TABLE XXX-continued

Results of BIMAS HLA Peptide Binding Prediction Analysis for Binding of Human WT1 Peptides to Human HLA CW0301

| Rank | Start Position | Subsequence Residue Listing | Score (Estimate of Half Time of Disassociation of a Molecule Containing This Subsequence) |
|---|---|---|---|
| 15 | 390 | RKFSRSDHL (SEQ ID NO: 183) | 6.000 |
| 16 | 423 | KKIFARSDEL (SEQ ID NO: 122) | 6.000 |
| 17 | 92 | FTVHFSGQF (SEQ ID NO: 85) | 5.000 |
| 18 | 429 | DELVRHHNM (SEQ ID NO: 53) | 5.000 |
| 19 | 130 | NAPYLPSCL (SEQ ID NO: 144) | 4.800 |
| 20 | 30 | GAAQWAPVL (SEQ ID NO: 86) | 4.000 |

TABLE XXXI

Results of BIMAS HLA Peptide Binding Prediction Analysis for Binding of Human WT1 Peptides to Human HLA CW0401

| Rank | Start Position | Subsequence Residue Listing | Score (Estimate of Half Time of Disassociation of a Molecule Containing This Subsequence) |
|---|---|---|---|
| 1 | 356 | DFKDCERRF (SEQ ID NO: 55) | 120.000 |
| 2 | 334 | YFKLSHLQM (SEQ ID NO: 248) | 100.000 |
| 3 | 180 | DPMGQQGSL (SEQ ID NO: 59) | 88.000 |
| 4 | 163 | TPSHHAAQF (SEQ ID NO: 228) | 52.800 |
| 5 | 327 | YPGCNKRYF (SEQ ID NO: 250) | 40.000 |
| 6 | 285 | QYRIHTHGV (SEQ ID NO: 175) | 27.500 |
| 7 | 424 | KFARSDELV (SEQ ID NO: 119) | 25.000 |
| 8 | 326 | AYPGCNKRY (SEQ ID NO: 42) | 25.000 |
| 9 | 192 | QYSVPPPVY (SEQ ID NO: 176) | 25.000 |
| 10 | 417 | RWPSCQKKF (SEQ ID NO: 196) | 22.000 |
| 11 | 278 | TPILCGAQY (SEQ ID NO: 227) | 12.000 |
| 12 | 10 | ALLPAVPSL (SEQ ID NO: 34) | 11.616 |
| 13 | 141 | QPAIRNQGY (SEQ ID NO: 170) | 11.000 |
| 14 | 303 | VPGVAPTLV (SEQ ID NO: 242) | 11.000 |
| 15 | 219 | TPYSSDNLY (SEQ ID NO: 231) | 10.000 |
| 16 | 39 | DFAPPGASA (SEQ ID NO: 54) | 7.920 |
| 17 | 99 | QFTGTAGAC (SEQ ID NO: 165) | 6.000 |
| 18 | 4 | DVRDLNALL (SEQ ID NO: 62) | 5.760 |
| 19 | 70 | SFIKQEPSW (SEQ ID NO: 210) | 5.500 |
| 20 | 63 | PPPPPPHSF (SEQ ID NO: 158) | 5.280 |

TABLE XXXII

Results of BIMAS HLA Peptide Binding Prediction Analysis for Binding of Human WT1 Peptides to Human HLA CW0602

| Rank | Start Position | Subsequence Residue Listing | Score (Estimate of Half Time of Disassociation of a Molecule Containing This Subsequence) |
|---|---|---|---|
| 1 | 332 | KRYFKLSHL (SEQ ID NO: 127) | 9.680 |
| 2 | 239 | NQMNLGATL (SEQ ID NO: 151) | 6.600 |
| 3 | 130 | NAPYLPSCL (SEQ ID NO: 144) | 6.600 |
| 4 | 7 | DLNALLPAV (SEQ ID NO: 58) | 6.000 |
| 5 | 441 | NMTKLQLAL (SEQ ID NO: 149) | 6.000 |
| 6 | 225 | NLYQMTSQL (SEQ ID NO: 147) | 6.000 |
| 7 | 4 | DVRDLNALL (SEQ ID NO: 62) | 6.000 |
| 8 | 3 | SDVRDLNAL (SEQ ID NO: 206) | 4.400 |
| 9 | 10 | ALLPAVPSL (SEQ ID NO: 34) | 4.000 |
| 10 | 213 | QALLLRTPY (SEQ ID NO: 160) | 3.300 |
| 11 | 319 | EKRPFMCAY (SEQ ID NO: 67) | 3.000 |
| 12 | 30 | GAAQWAPVL (SEQ ID NO: 86) | 2.200 |
| 13 | 242 | NLGATLKGV (SEQ ID NO: 146) | 2.200 |
| 14 | 292 | GVFRGIQDV (SEQ ID NO: 103) | 2.200 |
| 15 | 207 | DSCTGSQAL (SEQ ID NO: 61) | 2.200 |
| 16 | 362 | RRFSRSDQL (SEQ ID NO: 187) | 2.200 |
| 17 | 439 | QRNMTKLQL (SEQ ID NO: 173) | 2.200 |
| 18 | 295 | RGIQDVRRV (SEQ ID NO: 179) | 2.200 |
| 19 | 423 | KKFARSDEL (SEQ ID NO: 122) | 2.200 |
| 20 | 180 | DPMGQQGSL (SEQ ID NO: 59) | 2.200 |

TABLE XXXIII

Results of BIMAS HLA Peptide Binding Prediction Analysis for Binding of Human WT1 Peptides to Human HLA CW0702

| Rank | Start Position | Subsequence Residue Listing | Score (Estimate of Half Time of Disassociation of a Molecule Containing This Subsequence) |
|---|---|---|---|
| 1 | 319 | EKRPFMCAY (SEQ ID NO: 67) | 26.880 |
| 2 | 326 | AYPGCNKRY (SEQ ID NO: 42) | 24.000 |
| 3 | 40 | FAPPGASAY (SEQ ID NO: 74) | 14.784 |
| 4 | 192 | QYSVPPPVY (SEQ ID NO: 176) | 12.000 |
| 5 | 278 | TPILCGAQY (SEQ ID NO: 227) | 12.000 |
| 6 | 219 | TPYSSDNLY (SEQ ID NO: 231) | 12.000 |
| 7 | 213 | QALLLRTPY (SEQ ID NO: 160) | 8.800 |
| 8 | 125 | ARMFPNAPY (SEQ ID NO: 38) | 8.000 |
| 9 | 327 | YPGCNKRYF (SEQ ID NO: 250) | 6.600 |
| 10 | 152 | VTFDGTPSY (SEQ ID NO: 244) | 5.600 |
| 11 | 141 | QPAIRNQGY (SEQ ID NO: 170) | 4.800 |
| 12 | 345 | RKHTGEKPY (SEQ ID NO: 184) | 4.000 |
| 13 | 185 | QGSLGEQQY (SEQ ID NO: 166) | 4.000 |
| 14 | 101 | TGTAGACRY (SEQ ID NO: 224) | 4.000 |
| 15 | 375 | RRHTGVKPF (SEQ ID NO: 188) | 4.000 |
| 16 | 263 | GQSNHSTGY (SEQ ID NO: 100) | 4.000 |
| 17 | 163 | TPSHHAAQF (SEQ ID NO: 228) | 3.000 |
| 18 | 33 | QWAPVLDFA (SEQ ID NO: 174) | 2.688 |
| 19 | 130 | NAPYLPSCL (SEQ ID NO: 144) | 2.640 |
| 20 | 84 | HEEQCLSAF (SEQ ID NO: 107) | 2.400 |

TABLE XXXIV

Results of BIMAS HLA Peptide Binding Prediction Analysis for Binding of Human WT1 Peptides to Mouse MHC Class I Db

| Rank | Start Position | Subsequence Residue Listing | Score (Estimate of Half Time of Disassociation of a Molecule Containing This Subsequence) |
|---|---|---|---|
| 1 | 235 | CMTWNQMNL (SEQ ID NO: 49) | 5255.712 |
| 2 | 126 | RMFPNAPYL (SEQ ID NO: 185) | 1990.800 |
| 3 | 221 | YSSDNLYQM (SEQ ID NO: 253) | 930.000 |
| 4 | 228 | QMTSQLECM (SEQ ID NO: 169) | 33.701 |
| 5 | 239 | NQMNLGATL (SEQ ID NO: 151) | 21.470 |
| 6 | 441 | NMTKLQLAL (SEQ ID NO: 149) | 19.908 |
| 7 | 437 | MHQRNMTKL (SEQ ID NO: 143) | 19.837 |
| 8 | 136 | SCLESQPAI (SEQ ID NO: 198) | 11.177 |
| 9 | 174 | HSFKHEDPM (SEQ ID NO: 110) | 10.800 |
| 10 | 302 | RVPGVAPTL (SEQ ID NO: 195) | 10.088 |
| 11 | 130 | NAPYLPSCL (SEQ ID NO: 144) | 8.400 |
| 12 | 10 | ALLPAVPSL (SEQ ID NO: 34) | 5.988 |
| 13 | 208 | SCTGSQALL (SEQ ID NO: 202) | 4.435 |
| 14 | 209 | CTGSQALLL (SEQ ID NO: 52) | 3.548 |
| 15 | 238 | WNQMNLGAT (SEQ ID NO: 245) | 3.300 |
| 16 | 218 | RTPYSSDNL (SEQ ID NO: 194) | 3.185 |

TABLE XXXIV-continued

Results of BIMAS HLA Peptide Binding Prediction Analysis for Binding of Human WT1 Peptides to Mouse MHC Class I Db

| Rank | Start Position | Subsequence Residue Listing | Score (Estimate of Half Time of Disassociation of a Molecule Containing This Subsequence |
|---|---|---|---|
| 17 | 24 | CALPVSGAA (SEQ ID NO: 43) | 2.851 |
| 18 | 18 | LGGGGGCAL (SEQ ID NO: 134) | 2.177 |
| 19 | 142 | PAIRNQGYS (SEQ ID NO: 152) | 2.160 |
| 20 | 30 | GAAQWAPVL (SEQ ID NO: 86) | 1.680 |

TABLE XXXV

Results of BIMAS HLA Peptide Binding Prediction Analysis for Binding of Human WT1 Peptides to Mouse MHC Class I Dd

| Rank | Start Position | Subsequence Residue Listing | Score (Estimate of Half Time of Disassociation of a Molecule Containing This Subsequence |
|---|---|---|---|
| 1 | 112 | FGPPPPSQA (SEQ ID NO: 76) | 48.000 |
| 2 | 122 | SGQARMFPN (SEQ ID NO: 212) | 36.000 |
| 3 | 104 | AGACRYGPF (SEQ ID NO: 31) | 30.000 |
| 4 | 218 | RTPYSSDNL (SEQ ID NO: 194) | 28.800 |
| 5 | 130 | NAPYLPSCL (SEQ ID NO: 144) | 20.000 |
| 6 | 302 | RVPGVAPTL (SEQ ID NO: 195) | 20.000 |
| 7 | 18 | LGGGGGCAL (SEQ ID NO: 134) | 20.000 |
| 8 | 81 | AEPHEEQCL (SEQ ID NO: 30) | 10.000 |
| 9 | 29 | SGAAQWAPV (SEQ ID NO: 211) | 7.200 |
| 10 | 423 | KKFARSDEL (SEQ ID NO: 122) | 7.200 |
| 11 | 295 | RGIQDVRRV (SEQ ID NO: 179) | 7.200 |
| 12 | 390 | RKFSRSDHL (SEQ ID NO: 183) | 6.000 |
| 13 | 332 | KRYFKLSHL (SEQ ID NO: 127) | 6.000 |
| 14 | 362 | RRFSRSDQL (SEQ ID NO: 187) | 6.000 |
| 15 | 417 | RWPSCQKKF (SEQ ID NO: 196) | 6.000 |
| 16 | 160 | YGHTPSHHA (SEQ ID NO: 249) | 6.000 |
| 17 | 20 | GGGGCALPV (SEQ ID NO: 92) | 6.000 |
| 18 | 329 | GCNKRYFKL (SEQ ID NO: 90) | 5.000 |
| 19 | 372 | RHQRRHTGV (SEQ ID NO: 181) | 4.500 |
| 20 | 52 | GGPAPPPAP (SEQ ID NO: 93) | 4.000 |

TABLE XXXVI

Results of BIMAS HLA Peptide Binding Prediction Analysis for Binding of Human WT1 Peptides to Mouse MHC Class I Kb

| Rank | Start Position | Subsequence Residue Listing | Score (Estimate of Half Time of Disassociation of a Molecule Containing This Subsequence) |
|---|---|---|---|
| 1 | 329 | GCNKRYFKL (SEQ ID NO: 90) | 24.000 |
| 2 | 225 | NLYQMTSQL (SEQ ID NO: 147) | 10.000 |
| 3 | 420 | SCQKKFARS (SEQ ID NO: 200) | 3.960 |
| 4 | 218 | RTPYSSDNL (SEQ ID NO: 194) | 3.630 |
| 5 | 437 | MHQRNMTKL (SEQ ID NO: 143) | 3.600 |
| 6 | 387 | TCQRKFSRS (SEQ ID NO: 219) | 3.600 |
| 7 | 302 | RVPGVAPTL (SEQ ID NO: 195) | 3.300 |
| 8 | 130 | NAPYLPSCL (SEQ ID NO: 144) | 3.000 |
| 9 | 289 | HTHGVFRGI (SEQ ID NO: 113) | 3.000 |
| 10 | 43 | PGASAYGSL (SEQ ID NO: 153) | 2.400 |
| 11 | 155 | DGTPSYGHT (SEQ ID NO: 56) | 2.400 |
| 12 | 273 | SDNHTTPIL (SEQ ID NO: 204) | 2.200 |
| 13 | 126 | RMFPNAPYL (SEQ ID NO: 185) | 2.200 |
| 14 | 128 | FPNAPYLPS (SEQ ID NO: 79) | 2.000 |
| 15 | 3 | SDVRDLNAL (SEQ ID NO: 206) | 1.584 |
| 16 | 207 | DSCTGSQAL (SEQ ID NO: 61) | 1.584 |
| 17 | 332 | KRYFKLSHL (SEQ ID NO: 127) | 1.500 |
| 18 | 18 | LGGGGGCAL (SEQ ID NO: 134) | 1.320 |
| 19 | 233 | LECMTWNQM (SEQ ID NO: 131) | 1.320 |
| 20 | 441 | NMTKLQLAL (SEQ ID NO: 149) | 1.200 |

TABLE XXXVII

Results of BIMAS HLA Peptide Binding Prediction Analysis for Binding of Human WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 1 | 285 | QYRIHTGV (SEQ ID NO: 175) | 600.000 |
| 2 | 424 | KFARSDELV (SEQ ID NO: 119) | 288.000 |
| 3 | 334 | YFKLSHLQM (SEQ ID NO: 248) | 120.000 |
| 4 | 136 | SCLESQPTI (SEQ ID NO: 199) | 115.200 |
| 5 | 239 | NQMNLGATL (SEQ ID NO: 151) | 115.200 |
| 6 | 10 | ALLPAVSSL (SEQ ID NO: 35) | 115.200 |
| 7 | 47 | AYGSLGGPA (SEQ ID NO: 41) | 86.400 |
| 8 | 180 | DPMGQQGSL (SEQ ID NO: 59) | 80.000 |

TABLE XXXVII-continued

Results of BIMAS HLA Peptide Binding Prediction Analysis for Binding of Human WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 9 | 270 | GYESDNHTA (SEQ ID NO: 105) | 72.000 |
| 10 | 326 | AYPGCNKRY (SEQ ID NO: 42) | 60.000 |
| 11 | 192 | QYSVPPPVY (SEQ ID NO: 176) | 60.000 |
| 12 | 272 | ESDNHTAPI (SEQ ID NO: 70) | 57.600 |
| 13 | 289 | HTHGVFRGI (SEQ ID NO: 113) | 57.600 |
| 14 | 126 | DVRDLNALL (SEQ ID NO: 62) | 57.600 |
| 15 | 4 | CTGSQALLL (SEQ ID NO: 52) | 57.600 |
| 16 | 208 | SCTGSQALL (SEQ ID NO: 202) | 48.000 |
| 17 | 441 | NMTKLQLAL (SEQ ID NO: 149) | 48.000 |
| 18 | 207 | DSCTGSQAL (SEQ ID NO: 61) | 48.000 |
| 19 | 130 | NAPYLPSCL (SEQ ID NO: 144) | 48.000 |
| 20 | 235 | CMTWNQMNL (SEQ ID NO: 49) | 48.000 |

TABLE XXXVIII

Results of BIMAS HLA Peptide Binding Prediction Analysis for Binding of Human WT1 Peptides to Mouse MHC Class I Kk

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO: 30) | 40.000 |
| 2 | 85 | EEQCLSAFT (SEQ ID NO: 65) | 40.000 |
| 3 | 429 | DELVRHHNM (SEQ ID NO: 53) | 20.000 |
| 4 | 315 | SETSEKRPF (SEQ ID NO: 209) | 20.000 |
| 5 | 261 | TEGQSNHST (SEQ ID NO: 221) | 20.000 |
| 6 | 410 | SEKPFSCRW (SEQ ID NO: 207) | 10.000 |
| 7 | 272 | ESDNHTTPI (SEQ ID NO: 71) | 10.000 |
| 8 | 318 | SEKRPFMCA (SEQ ID NO: 208) | 10.000 |
| 9 | 138 | LESQPAIRN (SEQ ID NO: 132) | 10.000 |
| 10 | 233 | LECMTWNQM (SEQ ID NO: 131) | 10.000 |
| 11 | 298 | QDVRRVPGV (SEQ ID NO: 164) | 10.000 |
| 12 | 84 | HEEQCLSAF (SEQ ID NO: 107) | 10.000 |
| 13 | 349 | GEKPYQCDF (SEQ ID NO: 91) | 10.000 |
| 14 | 289 | HTHGVFRGI (SEQ ID NO: 113) | 10.000 |
| 15 | 179 | EDPMGQQGS (SEQ ID NO: 64) | 8.000 |
| 16 | 136 | SCLESQPAI (SEQ ID NO: 198) | 5.000 |

TABLE XXXVIII-continued

Results of BIMAS HLA Peptide Binding Prediction Analysis for Binding of Human WT1 Peptides to Mouse MHC Class I Kk

| Rank | Start Position | Subsequence Residue Listing | Score (Estimate of Half Time of Disassociation of a Molecule Containing This Subsequence) |
|---|---|---|---|
| 17 | 280 | ILCGAQYRI (SEQ ID NO: 116) | 5.000 |
| 18 | 273 | SDNHTTPIL (SEQ ID NO: 204) | 4.000 |
| 19 | 428 | SDELVRHHN (SEQ ID NO: 203) | 4.000 |
| 20 | 3 | SDVRDLNAL (SEQ ID NO: 206) | 4.000 |

TABLE XXXIX

Results of BIMAS HLA Peptide Binding Prediction Analysis for Binding of Human WT1 Peptides to Mouse MHC Class I Ld

| Rank | Start Position | Subsequence Residue Listing | Score (Estimate of Half Time of Disassociation of a Molecule Containing This Subsequence) |
|---|---|---|---|
| 1 | 163 | TPSHHAAQF (SEQ ID NO: 228) | 360.000 |
| 2 | 327 | YPGCNKRYF (SEQ ID NO: 250) | 300.000 |
| 3 | 180 | DPMGQQGSL (SEQ ID NO: 59) | 150.000 |
| 4 | 26 | LPVSGAAQW (SEQ ID NO: 138) | 93.600 |
| 5 | 278 | TPILCGAQY (SEQ ID NO: 227) | 72.000 |
| 6 | 141 | QPAIRNQGY (SEQ ID NO: 170) | 60.000 |
| 7 | 219 | TPYSSDNLY (SEQ ID NO: 231) | 60.000 |
| 8 | 303 | VPGVAPTLV (SEQ ID NO: 242) | 60.000 |
| 9 | 120 | ASSGQARMF (SEQ ID NO: 40) | 50.000 |
| 10 | 63 | PPPPPPHSF (SEQ ID NO: 158) | 45.000 |
| 11 | 113 | GPPPPSQAS (SEQ ID NO: 97) | 45.000 |
| 12 | 157 | TPSYGHTPS (SEQ ID NO: 229) | 39.000 |
| 13 | 207 | DSCTGSQAL (SEQ ID NO: 61) | 32.500 |
| 14 | 110 | GPFGPPPPS (SEQ ID NO: 96) | 30.000 |
| 15 | 82 | EPHEEQCLS (SEQ ID NO: 68) | 30.000 |
| 16 | 412 | KPFSCRWPS (SEQ ID NO: 123) | 30.000 |
| 17 | 418 | WPSCQKKFA (SEQ ID NO: 246) | 30.000 |
| 18 | 221 | YSSDNLYQM (SEQ ID NO: 253) | 30.000 |
| 19 | 204 | TPTDSCTGS (SEQ ID NO: 230) | 30.000 |
| 20 | 128 | FPNAPYLPS (SEQ ID NO: 79) | 30.000 |

TABLE XL

Results of BIMAS HLA Peptide Binding Prediction Analysis for Binding of Human WT1 Peptides to Cattle HLA A20

| Rank | Start Position | Subsequence Residue Listing | Score (Estimate of Half Time of Disassociation of a Molecule Containing This Subsequence) |
|---|---|---|---|
| 1 | 350 | EKPYQCDFK (SEQ ID NO: 66) | 1000.00 |
| 2 | 319 | EKRPFMCAY (SEQ ID NO: 67) | 500.000 |
| 3 | 423 | KKFARSDEL (SEQ ID NO: 122) | 500.000 |
| 4 | 345 | RKHTGEKPY (SEQ ID NO: 184) | 500.000 |
| 5 | 390 | RKFSRSDHL (SEQ ID NO: 183) | 500.000 |
| 6 | 137 | CLESQPAIR (SEQ ID NO: 47) | 120.000 |
| 7 | 380 | VKPFQCKTC (SEQ ID NO: 239) | 100.000 |
| 8 | 407 | GKTSEKPFS (SEQ ID NO: 95) | 100.000 |
| 9 | 335 | FKLSHLQMH (SEQ ID NO: 78) | 100.000 |
| 10 | 247 | LKGVAAGSS (SEQ ID NO: 135) | 100.000 |
| 11 | 370 | LKRHQRRHT (SEQ ID NO: 136) | 100.000 |
| 12 | 258 | VKWTEGQSN (SEQ ID NO: 240) | 100.000 |
| 13 | 398 | LKTHTRTHT (SEQ ID NO: 137) | 100.000 |
| 14 | 331 | NKRYFKLSH (SEQ ID NO: 145) | 100.000 |
| 15 | 357 | FKDCERRFS (SEQ ID NO: 77) | 100.000 |
| 16 | 385 | CKTCQRKFS (SEQ ID NO: 46) | 100.000 |
| 17 | 294 | FRGIQDVRR (SEQ ID NO: 81) | 80.000 |
| 18 | 368 | DQLKRHQRR (SEQ ID NO: 60) | 80.000 |
| 19 | 432 | VRHHNMHQR (SEQ ID NO: 243) | 80.000 |
| 20 | 118 | SQASSGQAR (SEQ ID NO: 216) | 80.000 |

TABLE XLI

Results of BIMAS HLA Peptide Binding Prediction Analysis for Binding of Mouse WT1 Peptides to Mouse MHC Class I A_0201

| Rank | Start Position | Subsequence Residue Listing | Score (Estimate of Half Time of Disassociation of a Molecule Containing This Subsequence) |
|---|---|---|---|
| 1 | 126 | RMFPNAPYL (SEQ ID NO: 293) | 313.968 |
| 2 | 187 | SLGEQQYSV (SEQ ID NO: 299) | 285.163 |
| 3 | 10 | ALLPAVSSL (SEQ ID NO: 255) | 181.794 |
| 4 | 225 | NLYQMTSQL (SEQ ID NO: 284) | 68.360 |
| 5 | 292 | GVFRGIQDV (SEQ ID NO: 270) | 51.790 |
| 6 | 93 | TLHFSGQFT (SEQ ID NO: 302) | 40.986 |
| 7 | 191 | QQYSVPPPV (SEQ ID NO: 290) | 22.566 |
| 8 | 280 | ILCGAQYRI (SEQ ID NO: 274) | 17.736 |
| 9 | 441 | NMTKLHVAL (SEQ ID NO: 285) | 15.428 |
| 10 | 235 | CMTWNQMNL (SEQ ID NO: 258) | 15.428 |
| 11 | 7 | DLNALLPAV (SEQ ID NO: 261) | 11.998 |
| 12 | 242 | NLGATLKGM (SEQ ID NO: 283) | 11.426 |
| 13 | 227 | YQMTSQLEC (SEQ ID NO: 307) | 8.573 |
| 14 | 239 | NQMNLGATL (SEQ ID NO: 286) | 8.014 |
| 15 | 309 | TLVRSASET (SEQ ID NO: 303) | 7.452 |
| 16 | 408 | KTSEKPFSC (SEQ ID NO: 277) | 5.743 |
| 17 | 340 | LQMHSRKHT (SEQ ID NO: 280) | 4.752 |
| 18 | 228 | QMTSQLECM (SEQ ID NO: 289) | 4.044 |
| 19 | 37 | VLDFAPPGA (SEQ ID NO: 304) | 3.378 |
| 20 | 302 | RVSGVAPTL (SEQ ID NO: 295) | 1.869 |

TABLE XLII

Results of BIMAS HLA Peptide Binding Prediction Analysis for Binding of Mouse WT1 Peptides to Mouse MHC Class I Db

| Rank | Start Position | Subsequence Residue Listing | Score (Estimate of Half Time of Disassociation of a Molecule Containing This Subsequence) |
|---|---|---|---|
| 1 | 221 | YSSDNLYQM (SEQ ID NO: 308) | 312.000 |
| 2 | 126 | RMFPNAPYL (SEQ ID NO: 293) | 260.000 |
| 3 | 235 | CMTWNQMNL (SEQ ID NO: 258) | 260.000 |
| 4 | 437 | MHQRNMTKL (SEQ ID NO: 281) | 200.000 |
| 5 | 238 | WNQMNLGAT (SEQ ID NO: 305) | 12.000 |
| 6 | 130 | NAPYLPSCL (SEQ ID NO: 282) | 8.580 |
| 7 | 3 | SDVRDLNAL (SEQ ID NO: 298) | 7.920 |
| 8 | 136 | SCLESQPTI (SEQ ID NO: 296) | 7.920 |
| 9 | 81 | AEPHEEQCL (SEQ ID NO: 254) | 6.600 |
| 10 | 10 | ALLPAVSSL (SEQ ID NO: 255) | 6.600 |
| 11 | 218 | RTPYSSDNL (SEQ ID NO: 294) | 6.000 |
| 12 | 441 | NMTKLHVAL (SEQ ID NO: 285) | 3.432 |
| 13 | 228 | QMTSQLECM (SEQ ID NO: 289) | 3.120 |
| 14 | 174 | HSFKHEDPM (SEQ ID NO: 272) | 3.120 |
| 15 | 242 | NLGATLKGM (SEQ ID NO: 283) | 2.640 |

TABLE XLII-continued

Results of BIMAS HLA Peptide Binding Prediction Analysis for Binding of Mouse WT1 Peptides to Mouse MHC Class I Db

| Rank | Start Position | Subsequence Residue Listing | Score (Estimate of Half Time of Disassociation of a Molecule Containing This Subsequence) |
|---|---|---|---|
| 16 | 261 | TEGQSNHGI (SEQ ID NO: 301) | 2.640 |
| 17 | 225 | NLYQMTSQL (SEQ ID NO: 284) | 2.640 |
| 18 | 207 | DSCTGSQAL (SEQ ID NO: 263) | 2.600 |
| 19 | 119 | QASSGQARM (SEQ ID NO: 288) | 2.600 |
| 20 | 18 | LGGGGGCGL (SEQ ID NO: 279) | 2.600 |

TABLE XLIII

Results of BIMAS HLA Peptide Binding Prediction Analysis for Binding of Mouse WT1 Peptides to Mouse MHC Class I Kb

| Rank | Start Position | Subsequence Residue Listing | Score (Estimate of Half Time of Disassociation of a Molecule Containing This Subsequence) |
|---|---|---|---|
| 1 | 329 | GCNKRYFKL (SEQ ID NO: 268) | 24.000 |
| 2 | 225 | NLYQMTSQL (SEQ ID NO: 284) | 10.000 |
| 3 | 420 | SCQKKFARS (SEQ ID NO: 297) | 3.960 |
| 4 | 218 | RTPYSSDNL (SEQ ID NO: 294) | 3.630 |
| 5 | 437 | MHQRNMTKL (SEQ ID NO: 281) | 3.600 |
| 6 | 387 | TCQRKFSRS (SEQ ID NO: 300) | 3.600 |
| 7 | 289 | HTHGVFRGI (SEQ ID NO: 273) | 3.000 |
| 8 | 130 | NAPYLPSCL (SEQ ID NO: 282) | 3.000 |
| 9 | 43 | PGASAYGSL (SEQ ID NO: 287) | 2.400 |
| 10 | 155 | DGAPSYGHT (SEQ ID NO: 260) | 2.400 |
| 11 | 126 | RMFPNAPYL (SEQ ID NO: 293) | 2.200 |
| 12 | 128 | FPNAPYLPS (SEQ ID NO: 267) | 2.000 |
| 13 | 207 | DSCTGSQAL (SEQ ID NO: 263) | 1.584 |
| 14 | 3 | SDVRDLNAL (SEQ ID NO: 298) | 1.584 |
| 15 | 332 | KRYFKLSHL (SEQ ID NO: 276) | 1.500 |
| 16 | 233 | LECMTWNQM (SEQ ID NO: 278) | 1.320 |
| 17 | 18 | LGGGGGCGL (SEQ ID NO: 279) | 1.320 |
| 18 | 242 | NLGATLKGM (SEQ ID NO: 283) | 1.200 |
| 19 | 123 | GQARMFPN (SEQ ID NO: 269)A | 1.200 |
| 20 | 441 | NMTKLHVAL (SEQ ID NO: 285) | 1.200 |

TABLE XLIV

Results of BIMAS HLA Peptide Binding Prediction Analysis for Binding of Mouse WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 1 | 285 | QYRIHTHGV (SEQ ID NO: 291) | 600.000 |
| 2 | 424 | KFARSDELV (SEQ ID NO: 275) | 288.000 |
| 3 | 334 | YFKLSHLQM (SEQ ID NO: 306) | 120.000 |
| 4 | 136 | SCLESQPTI (SEQ ID NO: 296) | 115.200 |
| 5 | 239 | NQMNLGATL (SEQ ID NO: 286) | 115.200 |
| 6 | 10 | ALLPAVSSL (SEQ ID NO: 255) | 115.200 |
| 7 | 47 | AYGSLGGPA (SEQ ID NO: 256) | 86.400 |
| 8 | 180 | DPMGQQGSL (SEQ ID NO: 262) | 80.000 |
| 9 | 270 | GYESDNHTA (SEQ ID NO: 271) | 72.000 |
| 10 | 192 | QYSVPPPVY (SEQ ID NO: 292) | 60.000 |
| 11 | 326 | AYPGCNKRY (SEQ ID NO: 257) | 60.000 |
| 12 | 289 | HTHGVFRGI (SEQ ID NO: 273) | 57.600 |
| 13 | 4 | DVRDLNALL (SEQ ID NO: 264) | 57.600 |
| 14 | 126 | RMFPNAPYL (SEQ ID NO: 293) | 57.600 |
| 15 | 209 | CTGSQALLL (SEQ ID NO: 259) | 48.000 |
| 16 | 86 | EQCLSAFTL (SEQ ID NO: 265) | 48.000 |
| 17 | 302 | RVSGVAPTL (SEQ ID NO: 295) | 48.000 |
| 18 | 218 | RTPYSSDNL (SEQ ID NO: 294) | 48.000 |
| 19 | 272 | ESDNHTAPI (SEQ ID NO: 266) | 48.000 |
| 20 | 225 | NLYQMTSQL (SEQ ID NO: 284) | 48.000 |

TABLE XLV

Results of TSites Peptide Binding Prediction Analysis for Human WT1 Peptides Capable of Eliciting a Helper T cell Response

| Peptide | Sequence |
|---|---|
| p6–23 | RDLNALLPAVPSLGGGG (SEQ ID NO: 1) |
| p30–35 | GAAQWA (SEQ ID NO: 309) |
| p45–56 | ASAYGSLGGPAP (SEQ ID NO: 310) |
| p91–105 | AFTVHFSGQFTGTAG (SEQ ID NO: 311) |
| p117–139 | PSQASSGQARMFPNAPYLPSCLE (SEQ ID NO: 2) |
| p167–171 | HAAQF (SEQ ID NO: 312) |
| p202–233 | CHTPTDSCTGSQALLLRTPYSSDNLYQMTSQL (SEQ ID NO: 313) |
| p244–262 | GATLKGVAAGSSSSVKWTE (SEQ ID NO: 4) |
| p287–318 | RIHTHGVFRGIQDVRRVPGVAPTLVRSASETS (SEQ ID NO: 314) |

TABLE XLV-continued

Results of TSites Peptide Binding Prediction Analysis for
Human WT1 Peptides Capable of Eliciting a Helper T cell Response

| Peptide | Sequence |
|---|---|
| p333–336 | RYFK (SEQ ID NO: 315) |
| p361–374 | ERRFSRSDQLKRHQ (SEQ ID NO: 316) |
| p389–410 | QRKFSRSDHLKTHTRTHTGKTS (SEQ ID NO: 317) |
| p421–441 | CQKKFARSDELVRHHNMHQRN (SEQ ID NO: 318) |

Certain CTL peptides (shown in Table XLVI) were selected for further study. For each peptide in Table XLVI, scores obtained using BIMAS HLA peptide binding prediction analysis are provided.

TABLE XLVI

WT1 Peptide Sequences and HLA Peptide Binding Predictions

| Peptide | Sequence | Comments |
|---|---|---|
| p329–337 | GCNKRYFKL (SEQ ID NOs: 90 and 268) | Score 24,000 |
| p225–233 | NLYQMTSQL (SEQ ID NOs: 147 and 284) | binds also to class II and HLA A2, Kd, score 10,000 |
| p235–243 | CMTWNQMNL (SEQ ID NOs: 49 and 258) | binds also to HLA A2, score 5,255,712 |
| p126–134 | RMFPNAPYL (SEQ ID NOs: 185 and 293) | binds also to Kd, class II and HLA A2, score 1,990,800 |
| p221–229 | YSSDNLYQM (SEQ ID NOs: 253 and 308) | binds also to Ld, score 312,000 |
| p228–236 | QMTSQLECM (SEQ ID NOs: 169 and 289) | score 3,120 |
| p239–247 | NQMNLGATL (SEQ ID NOs: 151 and 286) | binds also to HLA A 0201, Kd, score 8,015 |
| mouse p136–144 | SCLESQPTI (SEQ ID NO: 296) | binds also to Kd, 1 mismatch to human |
| human p136–144 | SCLESQPAI (SEQ ID NO: 198) | score 7,920 |
| mouse p10–18 | ALLPAVSSL (SEQ ID NO: 255) | binds also to Kd, HLA A2, 1 mismatch to human |
| human p10–18 | ALLPAVPSL (SEQ ID NO: 34) | score 6,600 |

Figure 6A:
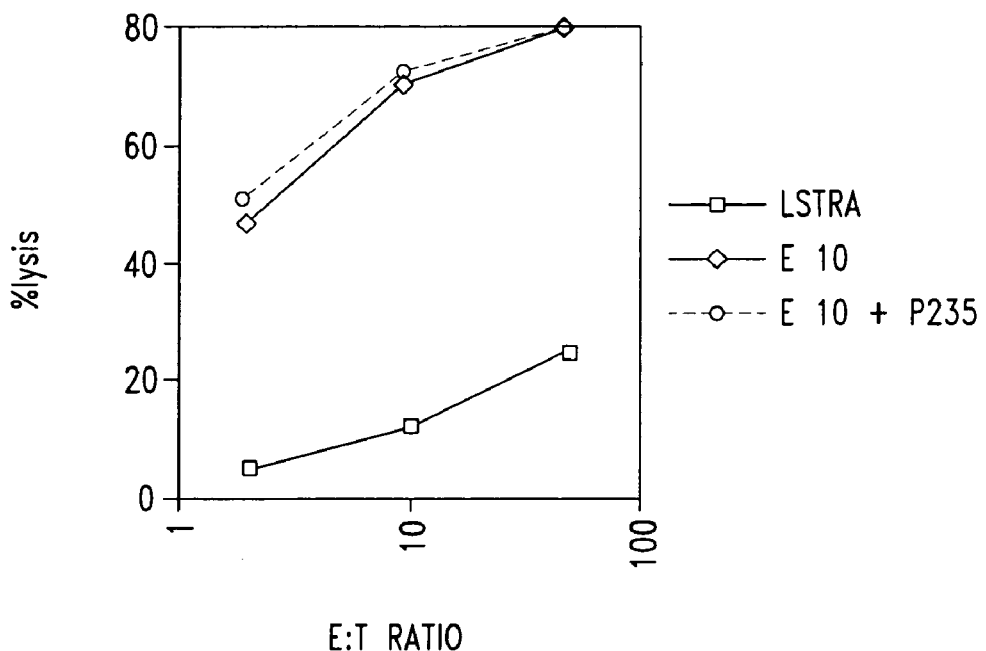
FIGS. 6A and 6B are graphs, illustrating the elicitation of WT1 peptide-specific CTL in mice immunized with WT1 peptides.
Figure 6B:
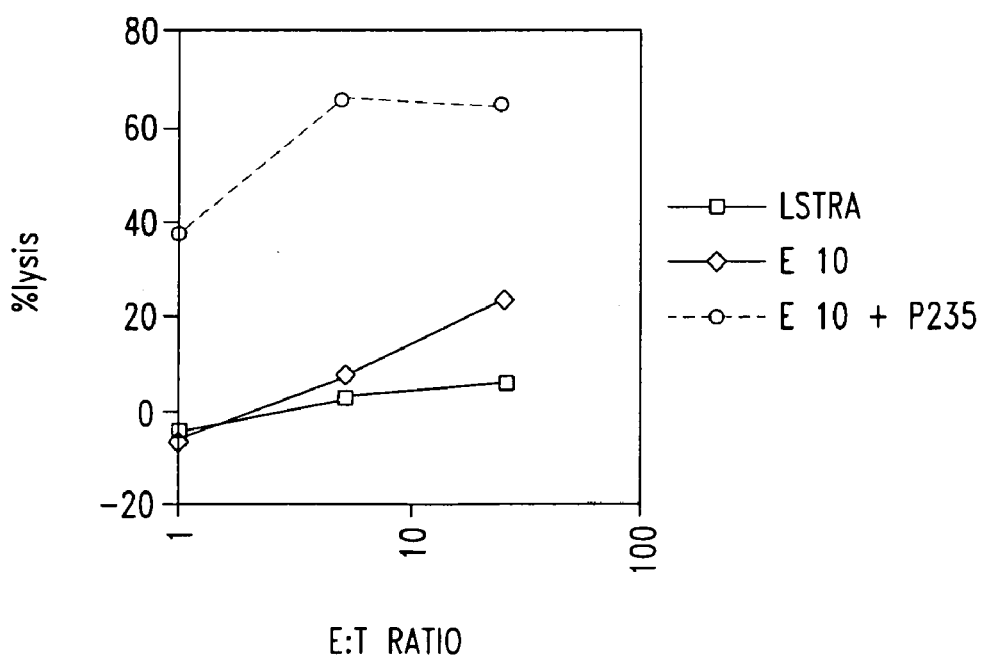
Figure 7A:
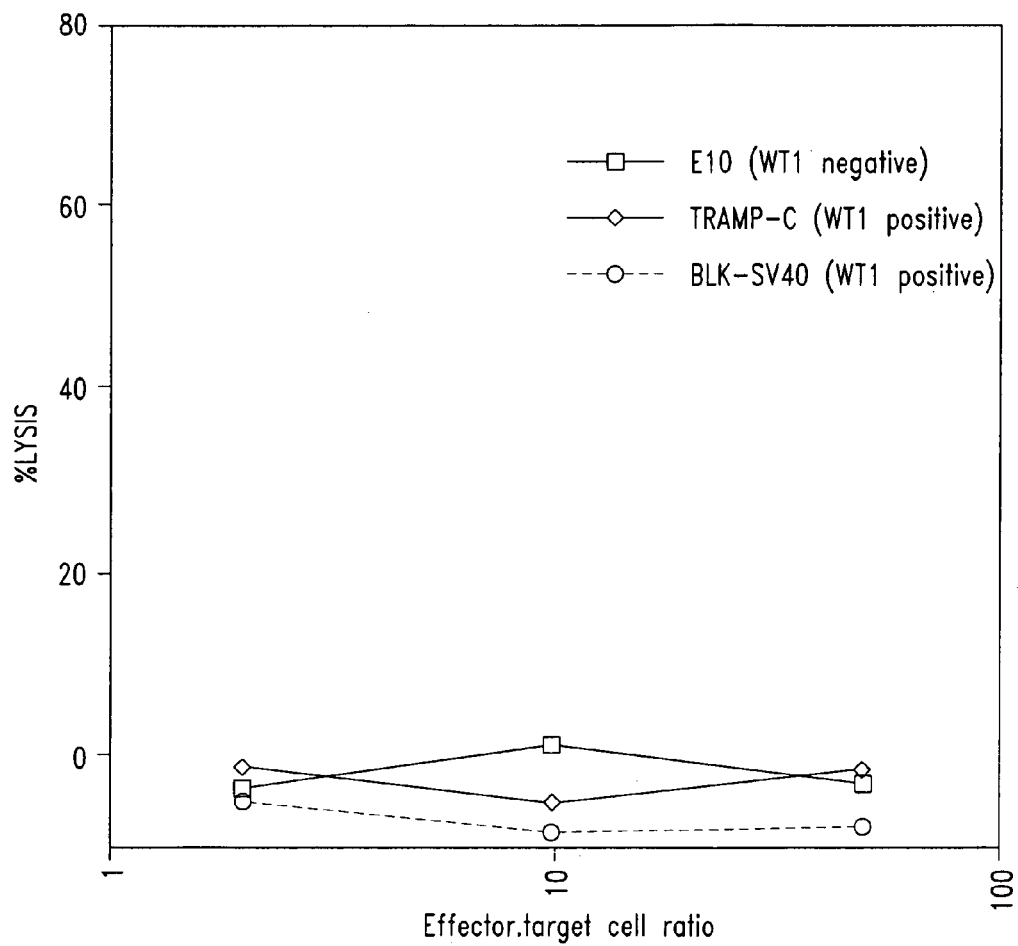
FIGS. 7A–7D are graphs illustrating the elicitation of WT1 specific CTL, which kill WT1 positive tumor cell lines but do not kill WT1 negative cell lines, following vaccination of B6 mice with WT1 peptide P117.
Figure 7B:
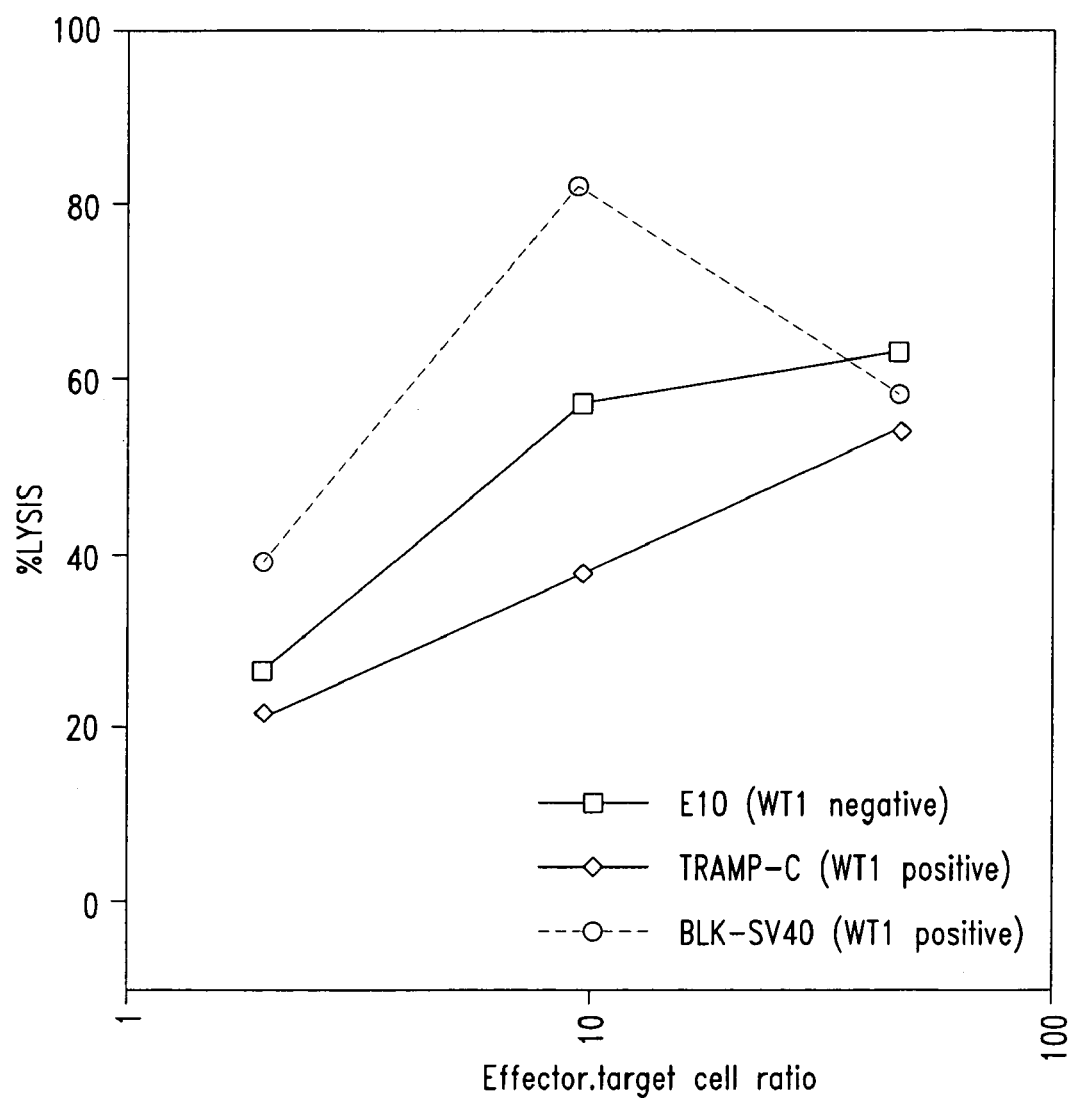
Figure 7C:
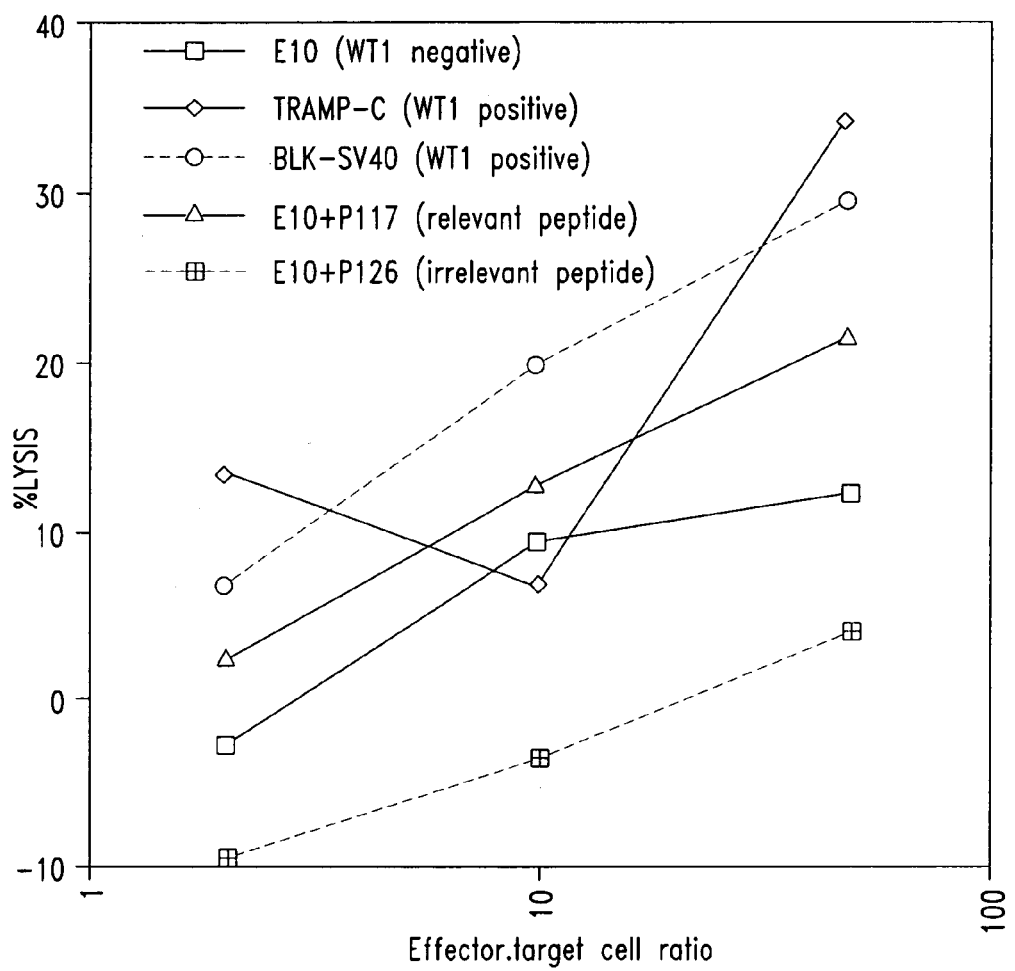
Figure 7D:
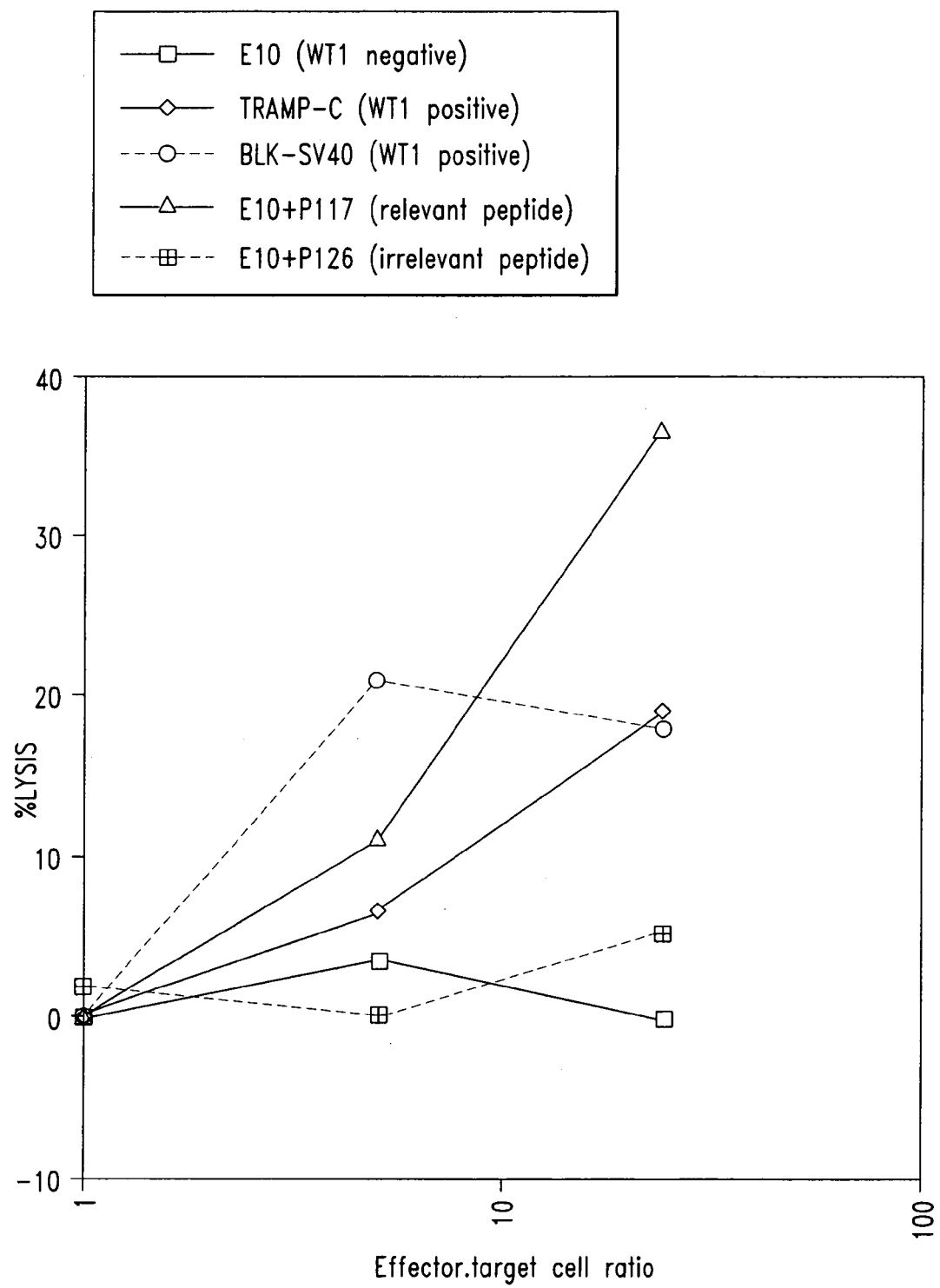

Peptide binding to C57Bl/6 murine MHC was confirmed using the RMA-S binding assay. Mice were immunized with the peptides capable of binding to murine class I MHC. Following immunization, spleen cells were stimulated in vitro and tested for the ability to lyse targets incubated with WT1 peptides. CTL were evaluated with a standard chromium release assay (Chen et al., Cancer Res. 54:1065–1070, 1994). The results, presented in Table XLVII, show that some WT1 peptides can bind to class I MHC molecules, which is essential for generating CTL. Moreover, several of the peptides were able to elicit peptide specific CTL (FIGS. 6A and 6B), as determined using chromium release assays. Following immunization to CTL peptides p10–18 human, p136–144 human, p136–144 mouse and p235–243, peptide specific CTL lines were generated and clones were established. These results indicate that peptide specific CTL can kill malignant cells expressing WT1.

TABLE XLVII

Binding of WT1 CTL Peptides to mouse B6 class I antigens

| Peptide | Binding Affinity to Mouse MHC Class I |
|---|---|
| Positive control | 91% |
| negative control | 0.5–1.3% |
| p235–243 | 33.6% |
| p136–144 mouse | 27.9% |
| p136–144 human | 52% |
| p10–18: human | 2.2% |
| p225–233 | 5.8% |
| p329–337 | 1.2% |
| p126–134 | 0.9% |
| p221–229 | 0.8% |
| p228–236 | 1.2% |
| p239–247 | 1% |

Example 5

Use of a WT1 Polypeptide to Elicit WT1 Specific CTL in Mice

This Example illustrates the ability of a representative WT1 polypeptide to elicit CTL immunity capable of killing WT1 positive tumor cell lines.

P117–139, a peptide with motifs appropriate for binding to class I and class II MHC, was identified as described above using TSITES and BIMAS HLA peptide binding prediction analyses. Mice were immunized as described in Example 3. Following immunization, spleen cells were stimulated in vitro and tested for the ability to lyse targets incubated with WT1 peptides, as well as WT1 positive and negative tumor cells. CTL were evaluated with a standard chromium release assay. The results, presented in FIGS. 7A–7D, show that P117 can elicit WT1 specific CTL capable of killing WT1 positive tumor cells, whereas no killing of WT1 negative cells was observed. These results demonstrate that peptide specific CTL in fact kill malignant cells expressing WT1 and that vaccine and T cell therapy are effective against malignancies that express WT 1.

Example 6

Identification of WT1 Specific mRNA in Mouse Tumor Cell Lines

This Example illustrates the use of RT-PCR to detect WT1 specific mRNA in cells and cell lines.

Mononuclear cells were isolated by density gradient centrifugation, and were immediately frozen and stored at −80° C. until analyzed by RT-PCR for the presence of WT1 specific mRNA. Total RNA was extracted from $10^7$ cells according to standard procedures. RNA pellets were resuspended in 25 μL diethylpyrocarbonate treated water and used directly for reverse transcription. Amplification was performed in a thermocycler during one or, when necessary, two sequential rounds of PCR. AmpliTaq DNA Polymerase (Perkin Elmer Cetus, Norwalk, Conn.), 2.5 mM $MgCl_2$ and 20 pmol of each primer in a total reaction volume of 50 μl were used. Twenty μL aliquots of the PCR products were electrophoresed on 2% agarose gels stained with ethidium bromide. The gels were photographed with Polaroid film (Polaroid 667, Polaroid Ltd., Hertfordshire, England). Precautions against cross contamination were taken following the recommendations of Kwok and Higuchi, Nature 339:

237–238, 1989. Negative controls included the cDNA- and PCR-reagent mixes with water instead of cDNA in each experiment. To avoid false negatives, the presence of intact RNA and adequate cDNA generation was evaluated for each sample by a control PCR using β-actin primers. Samples that did not amplify with these primers were excluded from analysis.

Primers for amplification of WT1 in mouse cell lines were: P115: 1458–1478: 5' CCC AGG CTG CAA TAA GAG ATA 3' (forward primer; SEQ ID NO:21); and P116: 1767–1787: 5' ATG TTG TGA TGG CGG ACC AAT 3' (reverse primer; SEQ ID NO:22) (see Inoue et al, *Blood* 88:2267–2278, 1996; Fraizer et al., *Blood* 86:4704–4706, 1995).

Beta Actin primers used in the control reactions were: 5' GTG GGG CGC CCC AGG CAC CA 3' (sense primer; SEQ ID NO:23); and 5' GTC CTT AAT GTC ACG CAC GAT TTC 3' (antisense primer; SEQ ID NO:24)

Primers for use in amplifying human WT1 include: P117: 954–974: 5' GGC ATC TGA GAC CAG TGA GAA 3' (SEQ ID NO:25); and P118: 1434–1414: 5' GAG AGT CAG ACT TGA AAG CAGT 3' (SEQ ID NO:5). For nested RT-PCR, primers may be: P119: 1023–1043: 5' GCT GTC CCA CTT ACA GAT GCA 3' (SEQ ID NO:26); and P120: 1345–1365: 5' TCA AAG CGC CAG CTG GAG TTT 3' (SEQ ID NO:27).

Table XLVIII shows the results of WT1 PCR analysis of mouse tumor cell lines. Within Table IV, (+++) indicates a strong WT1 PCR amplification product in the first step RT PCR, (++) indicates a WT1 amplification product that is detectable by first step WT1 RT PCR, (+) indicates a product that is detectable only in the second step of WT1 RT PCR, and (–) indicates WT1 PCR negative.

TABLE XLVIII

Detection of WT1 mRNA in Mouse Tumor Cell Lines

| Cell Line | WT1 mRNA |
|---|---|
| K562 (human leukemia; ATCC): Positive control; (Lozzio and Lozzio, Blood 45: 321–334, 1975) | +++ |
| TRAMPC (SV40 transformed prostate, B6); Foster et al., Cancer Res. 57: 3325–3330, 1997 | +++ |
| BLK SV40 HD2 (SV40-transf. fibroblast, B6; ATCC); Nature 276: 510–511, 1978 | ++ |
| CTLL (T-cell, B6; ATCC); Gillis, Nature 268: 154–156, 1977 | + |
| FM (FBL-3 subline, leukemia, B6); Glynn and Fefer, Cancer Res. 28: 434–439, 1968 | + |
| BALB 3T3 (ATCC); Aaroston and Todaro, J. Cell. Physiol. 72: 141–148, 1968 | + |
| S49.1 (Lymphoma, T-cell like, B/C; ATCC); Horibata and Harris, Exp. Cell. Res. 60: 61, 1970 | + |
| BNL CL.2 (embryonic liver, B/C; ATCC); Nature 276: 510–511, 1978 | + |
| MethA (sarcoma, B/C); Old et al., Ann. NY Acad. Sci. 101: 80–106, 1962 | – |
| P3.6.2.8.1 (myeloma, B/C; ATCC); Proc. Natl. Acad. Sci. USA 66: 344, 1970 | – |
| P2N (leukemia, DBA/2; ATCC); Melling et al., J Immunol. 117: 1267–1274, 1976 | – |
| BCL1 (lymphoma, B/C; ATCC); Slavin and Strober, Nature 272: 624–626, 1977 | – |
| LSTRA (lymphoma, B/C); Glynn et al., Cancer Res. 28: 434–439, 1968 | – |
| E10 (lymphoma, B6); Glynn et al., Cancer Res. 28: 434–439, 1968 | – |

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A polypeptide consisting of an immunogenic portion of native WT1, wherein the immunogenic portion consists of the contiguous amino acids of SEQ ID NO:2.

2. A composition comprising an immunogenic portion of native WT1, wherein the immunogenic portion consists of the contiguous amino acids of SEQ ID NO:2.

* * * * *

UNITED STATES PATENT AND TRADEMARK OFFICE
CERTIFICATE OF CORRECTION

| | | |
|---|---|---|
| PATENT NO. | : 7,063,854 B1 | Page 1 of 1 |
| APPLICATION NO. | : 09/164223 | |
| DATED | : June 20, 2006 | |
| INVENTOR(S) | : Alexander Gaiger et al. | |

It is certified that error appears in the above-identified patent and that said Letters Patent is hereby corrected as shown below:

<u>Column 1</u>
Lines 6-10, "This invention was made with U.S. Government support. The Government may have certain rights in this invention" should read as --This invention was made with U.S. Government support under grant number #R37CA30558 awarded by U.S. Department of Health and Human Services, National Institutes of Health, National Cancer Institute. The U.S. Government has certain rights in this invention--.

Signed and Sealed this

Seventh Day of November, 2006

JON W. DUDAS
*Director of the United States Patent and Trademark Office*

UNITED STATES PATENT AND TRADEMARK OFFICE
CERTIFICATE OF CORRECTION

PATENT NO.        : 7,063,854 B1                                       Page 1 of 1
APPLICATION NO.   : 09/164223
DATED             : June 20, 2006
INVENTOR(S)       : Alexander Gaiger et al.

It is certified that error appears in the above-identified patent and that said Letters Patent is hereby corrected as shown below:

Column 1
Line 6, Statement Of Government Interest, "This invention was made with U.S. Government support under grant number R37CA30558 awarded by U.S. Department of Health and Human Services, National Institutes of Health, National Cancer Institute. The U.S. Government has certain rights in this invention" should read, --This invention was made with U.S. government support under Grant Numbers IR 43 CA81752-01A1 and NIH/NCI R37CA30558 awarded by the National Institutes of Health. The U.S. government has certain rights in this invention--.

Signed and Sealed this

Twenty-ninth Day of June, 2010

David J. Kappos
*Director of the United States Patent and Trademark Office*

SEQUENCE LISTING

<160> NUMBER OF SEQ ID NOS: 320

<210> SEQ ID NO 1
<211> LENGTH: 17
<212> TYPE: PRT
<213> ORGANISM: Homo sapiens

<400> SEQUENCE: 1

Arg Asp Leu Asn Ala Leu Leu Pro Ala Val Pro Ser Leu Gly Gly Gly
 1               5                  10                  15

Gly

<210> SEQ ID NO 2
<211> LENGTH: 23
<212> TYPE: PRT
<213> ORGANISM: Homo sapiens

-continued

```
<400> SEQUENCE: 2

Pro Ser Gln Ala Ser Ser Gly Gln Ala Arg Met Phe Pro Asn Ala Pro
 1               5                  10                  15

Tyr Leu Pro Ser Cys Leu Glu
            20

<210> SEQ ID NO 3
<211> LENGTH: 23
<212> TYPE: PRT
<213> ORGANISM: Mus musculus

<400> SEQUENCE: 3

Pro Ser Gln Ala Ser Ser Gly Gln Ala Arg Met Phe Pro Asn Ala Pro
 1               5                  10                  15

Tyr Leu Pro Ser Cys Leu Glu
            20

<210> SEQ ID NO 4
<211> LENGTH: 19
<212> TYPE: PRT
<213> ORGANISM: Homo sapiens

<400> SEQUENCE: 4

Gly Ala Thr Leu Lys Gly Val Ala Ala Gly Ser Ser Ser Ser Val Lys
 1               5                  10                  15

Trp Thr Glu

<210> SEQ ID NO 5
<211> LENGTH: 22
<212> TYPE: DNA
<213> ORGANISM: Artificial Sequence
<220> FEATURE:
<223> OTHER INFORMATION: Primer for Amplification of human WT1

<400> SEQUENCE: 5
gagagtcaga cttgaaagca gt                                        22

<210> SEQ ID NO 6
<211> LENGTH: 20
<212> TYPE: DNA
<213> ORGANISM: Artificial Sequence
<220> FEATURE:
<223> OTHER INFORMATION: Primer for Amplification of human WT1

<400> SEQUENCE: 6
ctgagcctca gcaaatgggc                                           20

<210> SEQ ID NO 7
<211> LENGTH: 27
<212> TYPE: DNA
<213> ORGANISM: Artificial Sequence
<220> FEATURE:
<223> OTHER INFORMATION: Primer for Amplification of human WT1

<400> SEQUENCE: 7
gagcatgcat gggctccgac gtgcggg                                   27

<210> SEQ ID NO 8
<211> LENGTH: 25
<212> TYPE: DNA
<213> ORGANISM: Artificial Sequence
<220> FEATURE:
<223> OTHER INFORMATION: Primer for Amplification of human WT1
```

-continued

```
<400> SEQUENCE: 8
ggggtaccca ctgaacggtc cccga                                            25

<210> SEQ ID NO 9
<211> LENGTH: 18
<212> TYPE: DNA
<213> ORGANISM: Artificial Sequence
<220> FEATURE:
<223> OTHER INFORMATION: Primer for amplification of mouse WT1

<400> SEQUENCE: 9
tccgagccgc acctcatg                                                    18

<210> SEQ ID NO 10
<211> LENGTH: 18
<212> TYPE: DNA
<213> ORGANISM: Artificial Sequence
<220> FEATURE:
<223> OTHER INFORMATION: Primer for amplification of mouse WT1

<400> SEQUENCE: 10
gcctgggatg ctggactg                                                    18

<210> SEQ ID NO 11
<211> LENGTH: 27
<212> TYPE: DNA
<213> ORGANISM: Artificial Sequence
<220> FEATURE:
<223> OTHER INFORMATION: Primer for amplification of mouse WT1

<400> SEQUENCE: 11
gagcatgcga tgggttccga cgtgcgg                                          27

<210> SEQ ID NO 12
<211> LENGTH: 29
<212> TYPE: DNA
<213> ORGANISM: Artificial Sequence
<220> FEATURE:
<223> OTHER INFORMATION: Primer for amplification of mouse WT1

<400> SEQUENCE: 12
ggggtacctc aaagcgccac gtggagttt                                        29

<210> SEQ ID NO 13
<211> LENGTH: 17
<212> TYPE: PRT
<213> ORGANISM: Mus musculus

<400> SEQUENCE: 13

Arg Asp Leu Asn Ala Leu Leu Pro Ala Val Ser Ser Leu Gly Gly Gly
 1               5                  10                  15

Gly

<210> SEQ ID NO 14
<211> LENGTH: 19
<212> TYPE: PRT
<213> ORGANISM: Mus musculus

<400> SEQUENCE: 14

Gly Ala Thr Leu Lys Gly Met Ala Ala Gly Ser Ser Ser Ser Val Lys
 1               5                  10                  15

Trp Thr Glu
```

-continued

```
<210> SEQ ID NO 15
<211> LENGTH: 15
<212> TYPE: PRT
<213> ORGANISM: Homo sapiens

<400> SEQUENCE: 15

Arg Ile His Thr His Gly Val Phe Arg Gly Ile Gln Asp Val Arg
 1               5                  10                  15

<210> SEQ ID NO 16
<211> LENGTH: 15
<212> TYPE: PRT
<213> ORGANISM: Mus musculus

<400> SEQUENCE: 16

Arg Ile His Thr His Gly Val Phe Arg Gly Ile Gln Asp Val Arg
 1               5                  10                  15

<210> SEQ ID NO 17
<211> LENGTH: 14
<212> TYPE: PRT
<213> ORGANISM: Mus musculus

<400> SEQUENCE: 17

Val Arg Arg Val Ser Gly Val Ala Pro Thr Leu Val Arg Ser
 1               5                  10

<210> SEQ ID NO 18
<211> LENGTH: 14
<212> TYPE: PRT
<213> ORGANISM: Homo sapiens

<400> SEQUENCE: 18

Val Arg Arg Val Pro Gly Val Ala Pro Thr Leu Val Arg Ser
 1               5                  10

<210> SEQ ID NO 19
<211> LENGTH: 15
<212> TYPE: PRT
<213> ORGANISM: Homo sapiens

<400> SEQUENCE: 19

Cys Gln Lys Lys Phe Ala Arg Ser Asp Glu Leu Val Arg His His
 1               5                  10                  15

<210> SEQ ID NO 20
<211> LENGTH: 15
<212> TYPE: PRT
<213> ORGANISM: Mus musculus

<400> SEQUENCE: 20

Cys Gln Lys Lys Phe Ala Arg Ser Asp Glu Leu Val Arg His His
 1               5                  10                  15

<210> SEQ ID NO 21
<211> LENGTH: 21
<212> TYPE: DNA
<213> ORGANISM: Artificial Sequence
<220> FEATURE:
<223> OTHER INFORMATION: Primer for amplification of mouse WT1

<400> SEQUENCE: 21
cccaggctgc aataagagat a                                           21

<210> SEQ ID NO 22
```

```
<211> LENGTH: 21
<212> TYPE: DNA
<213> ORGANISM: Artificial Sequence
<220> FEATURE:
<223> OTHER INFORMATION: Antisense primer for amplification of mouse WT1

<400> SEQUENCE: 22
atgttgtgat ggcggaccaa t                                              21

<210> SEQ ID NO 23
<211> LENGTH: 20
<212> TYPE: DNA
<213> ORGANISM: Artificial Sequence
<220> FEATURE:
<223> OTHER INFORMATION: Primer for amplification of Beta Actin

<400> SEQUENCE: 23
gtggggcgcc ccaggcacca                                                20

<210> SEQ ID NO 24
<211> LENGTH: 24
<212> TYPE: DNA
<213> ORGANISM: Artificial Sequence
<220> FEATURE:
<223> OTHER INFORMATION: Antisense primer for amplification of Beta
      Actin

<400> SEQUENCE: 24
gtccttaatg ctacgcacga tttc                                           24

<210> SEQ ID NO 25
<211> LENGTH: 21
<212> TYPE: DNA
<213> ORGANISM: Artificial Sequence
<220> FEATURE:
<223> OTHER INFORMATION: Primer for Amplification of human WT1

<400> SEQUENCE: 25
ggcatctgag accagtgaga a                                              21

<210> SEQ ID NO 26
<211> LENGTH: 21
<212> TYPE: DNA
<213> ORGANISM: Artificial Sequence
<220> FEATURE:
<223> OTHER INFORMATION: Primer for Amplification of human WT1

<400> SEQUENCE: 26
gctgtcccac ttacagatgc a                                              21

<210> SEQ ID NO 27
<211> LENGTH: 21
<212> TYPE: DNA
<213> ORGANISM: Artificial Sequence
<220> FEATURE:
<223> OTHER INFORMATION: Primer for Amplification of human WT1

<400> SEQUENCE: 27
tcaaagcgcc agctggagtt t                                              21

<210> SEQ ID NO 28
<211> LENGTH: 9
<212> TYPE: PRT
<213> ORGANISM: Homo sapiens

<400> SEQUENCE: 28
```

Ala Ala Gly Ser Ser Ser Ser Val Lys
 1               5

<210> SEQ ID NO 29
<211> LENGTH: 9
<212> TYPE: PRT
<213> ORGANISM: Homo sapiens

<400> SEQUENCE: 29

Ala Ala Gln Phe Pro Asn His Ser Phe
 1               5

<210> SEQ ID NO 30
<211> LENGTH: 9
<212> TYPE: PRT
<213> ORGANISM: Homo sapiens

<400> SEQUENCE: 30

Ala Glu Pro His Glu Glu Gln Cys Leu
 1               5

<210> SEQ ID NO 31
<211> LENGTH: 9
<212> TYPE: PRT
<213> ORGANISM: Homo sapiens

<400> SEQUENCE: 31

Ala Gly Ala Cys Arg Tyr Gly Pro Phe
 1               5

<210> SEQ ID NO 32
<211> LENGTH: 9
<212> TYPE: PRT
<213> ORGANISM: Homo sapiens

<400> SEQUENCE: 32

Ala Gly Ser Ser Ser Ser Val Lys Trp
 1               5

<210> SEQ ID NO 33
<211> LENGTH: 9
<212> TYPE: PRT
<213> ORGANISM: Homo sapiens

<400> SEQUENCE: 33

Ala Ile Arg Asn Gln Gly Tyr Ser Thr
 1               5

<210> SEQ ID NO 34
<211> LENGTH: 9
<212> TYPE: PRT
<213> ORGANISM: Homo sapiens

<400> SEQUENCE: 34

Ala Leu Leu Pro Ala Val Pro Ser Leu
 1               5

<210> SEQ ID NO 35
<211> LENGTH: 9
<212> TYPE: PRT
<213> ORGANISM: Homo sapiens

<400> SEQUENCE: 35

Ala Leu Leu Pro Ala Val Ser Ser Leu
 1               5

<210> SEQ ID NO 36
<211> LENGTH: 9
<212> TYPE: PRT
<213> ORGANISM: Homo sapiens

<400> SEQUENCE: 36

Ala Gln Phe Pro Asn His Ser Phe Lys
 1               5

<210> SEQ ID NO 37
<211> LENGTH: 9
<212> TYPE: PRT
<213> ORGANISM: Homo sapiens

<400> SEQUENCE: 37

Ala Gln Trp Ala Pro Val Leu Asp Phe
 1               5

<210> SEQ ID NO 38
<211> LENGTH: 9
<212> TYPE: PRT
<213> ORGANISM: Homo sapiens

<400> SEQUENCE: 38

Ala Arg Met Phe Pro Asn Ala Pro Tyr
 1               5

<210> SEQ ID NO 39
<211> LENGTH: 9
<212> TYPE: PRT
<213> ORGANISM: Homo sapiens

<400> SEQUENCE: 39

Ala Arg Ser Asp Glu Leu Val Arg His
 1               5

<210> SEQ ID NO 40
<211> LENGTH: 9
<212> TYPE: PRT
<213> ORGANISM: Homo sapiens

<400> SEQUENCE: 40

Ala Ser Ser Gly Gln Ala Arg Met Phe
 1               5

<210> SEQ ID NO 41
<211> LENGTH: 9
<212> TYPE: PRT
<213> ORGANISM: Homo sapiens

<400> SEQUENCE: 41

Ala Tyr Gly Ser Leu Gly Gly Pro Ala
 1               5

<210> SEQ ID NO 42
<211> LENGTH: 9
<212> TYPE: PRT
<213> ORGANISM: Homo sapiens

<400> SEQUENCE: 42

Ala Tyr Pro Gly Cys Asn Lys Arg Tyr
 1               5

```
<210> SEQ ID NO 43
<211> LENGTH: 9
<212> TYPE: PRT
<213> ORGANISM: Homo sapiens

<400> SEQUENCE: 43

Cys Ala Leu Pro Val Ser Gly Ala Ala
 1               5

<210> SEQ ID NO 44
<211> LENGTH: 9
<212> TYPE: PRT
<213> ORGANISM: Homo sapiens

<400> SEQUENCE: 44

Cys Ala Tyr Pro Gly Cys Asn Lys Arg
 1               5

<210> SEQ ID NO 45
<211> LENGTH: 9
<212> TYPE: PRT
<213> ORGANISM: Homo sapiens

<400> SEQUENCE: 45

Cys His Thr Pro Thr Asp Ser Cys Thr
 1               5

<210> SEQ ID NO 46
<211> LENGTH: 9
<212> TYPE: PRT
<213> ORGANISM: Homo sapiens

<400> SEQUENCE: 46

Cys Lys Thr Cys Gln Arg Lys Phe Ser
 1               5

<210> SEQ ID NO 47
<211> LENGTH: 9
<212> TYPE: PRT
<213> ORGANISM: Homo sapiens

<400> SEQUENCE: 47

Cys Leu Glu Ser Gln Pro Ala Ile Arg
 1               5

<210> SEQ ID NO 48
<211> LENGTH: 9
<212> TYPE: PRT
<213> ORGANISM: Homo sapiens

<400> SEQUENCE: 48

Cys Leu Ser Ala Phe Thr Val His Phe
 1               5

<210> SEQ ID NO 49
<211> LENGTH: 9
<212> TYPE: PRT
<213> ORGANISM: Homo sapiens

<400> SEQUENCE: 49

Cys Met Thr Trp Asn Gln Met Asn Leu
 1               5

<210> SEQ ID NO 50
<211> LENGTH: 9
```

```
<212> TYPE: PRT
<213> ORGANISM: Homo sapiens

<400> SEQUENCE: 50

Cys Arg Trp Pro Ser Cys Gln Lys Lys
 1               5

<210> SEQ ID NO 51
<211> LENGTH: 9
<212> TYPE: PRT
<213> ORGANISM: Homo sapiens

<400> SEQUENCE: 51

Cys Arg Tyr Gly Pro Phe Gly Pro Pro
 1               5

<210> SEQ ID NO 52
<211> LENGTH: 9
<212> TYPE: PRT
<213> ORGANISM: Homo sapiens

<400> SEQUENCE: 52

Cys Thr Gly Ser Gln Ala Leu Leu Leu
 1               5

<210> SEQ ID NO 53
<211> LENGTH: 9
<212> TYPE: PRT
<213> ORGANISM: Homo sapiens

<400> SEQUENCE: 53

Asp Glu Leu Val Arg His His Asn Met
 1               5

<210> SEQ ID NO 54
<211> LENGTH: 9
<212> TYPE: PRT
<213> ORGANISM: Homo sapiens

<400> SEQUENCE: 54

Asp Phe Ala Pro Pro Gly Ala Ser Ala
 1               5

<210> SEQ ID NO 55
<211> LENGTH: 9
<212> TYPE: PRT
<213> ORGANISM: Homo sapiens

<400> SEQUENCE: 55

Asp Phe Lys Asp Cys Glu Arg Arg Phe
 1               5

<210> SEQ ID NO 56
<211> LENGTH: 9
<212> TYPE: PRT
<213> ORGANISM: Homo sapiens

<400> SEQUENCE: 56

Asp Gly Thr Pro Ser Tyr Gly His Thr
 1               5

<210> SEQ ID NO 57
<211> LENGTH: 9
<212> TYPE: PRT
<213> ORGANISM: Homo sapiens
```

```
<400> SEQUENCE: 57

Asp His Leu Lys Thr His Thr Arg Thr
 1               5

<210> SEQ ID NO 58
<211> LENGTH: 9
<212> TYPE: PRT
<213> ORGANISM: Homo sapiens

<400> SEQUENCE: 58

Asp Leu Asn Ala Leu Leu Pro Ala Val
 1               5

<210> SEQ ID NO 59
<211> LENGTH: 9
<212> TYPE: PRT
<213> ORGANISM: Homo sapiens

<400> SEQUENCE: 59

Asp Pro Met Gly Gln Gln Gly Ser Leu
 1               5

<210> SEQ ID NO 60
<211> LENGTH: 9
<212> TYPE: PRT
<213> ORGANISM: Homo sapiens

<400> SEQUENCE: 60

Asp Gln Leu Lys Arg His Gln Arg Arg
 1               5

<210> SEQ ID NO 61
<211> LENGTH: 9
<212> TYPE: PRT
<213> ORGANISM: Homo sapiens

<400> SEQUENCE: 61

Asp Ser Cys Thr Gly Ser Gln Ala Leu
 1               5

<210> SEQ ID NO 62
<211> LENGTH: 9
<212> TYPE: PRT
<213> ORGANISM: Homo sapiens

<400> SEQUENCE: 62

Asp Val Arg Asp Leu Asn Ala Leu Leu
 1               5

<210> SEQ ID NO 63
<211> LENGTH: 9
<212> TYPE: PRT
<213> ORGANISM: Homo sapiens

<400> SEQUENCE: 63

Asp Val Arg Arg Val Pro Gly Val Ala
 1               5

<210> SEQ ID NO 64
<211> LENGTH: 9
<212> TYPE: PRT
<213> ORGANISM: Homo sapiens

<400> SEQUENCE: 64
```

Glu Asp Pro Met Gly Gln Gln Gly Ser
1               5

<210> SEQ ID NO 65
<211> LENGTH: 9
<212> TYPE: PRT
<213> ORGANISM: Homo sapiens

<400> SEQUENCE: 65

Glu Glu Gln Cys Leu Ser Ala Phe Thr
1               5

<210> SEQ ID NO 66
<211> LENGTH: 9
<212> TYPE: PRT
<213> ORGANISM: Homo sapiens

<400> SEQUENCE: 66

Glu Lys Pro Tyr Gln Cys Asp Phe Lys
1               5

<210> SEQ ID NO 67
<211> LENGTH: 9
<212> TYPE: PRT
<213> ORGANISM: Homo sapiens

<400> SEQUENCE: 67

Glu Lys Arg Pro Phe Met Cys Ala Tyr
1               5

<210> SEQ ID NO 68
<211> LENGTH: 9
<212> TYPE: PRT
<213> ORGANISM: Homo sapiens

<400> SEQUENCE: 68

Glu Pro His Glu Glu Gln Cys Leu Ser
1               5

<210> SEQ ID NO 69
<211> LENGTH: 9
<212> TYPE: PRT
<213> ORGANISM: Homo sapiens

<400> SEQUENCE: 69

Glu Gln Cys Leu Ser Ala Phe Thr Val
1               5

<210> SEQ ID NO 70
<211> LENGTH: 9
<212> TYPE: PRT
<213> ORGANISM: Homo sapiens

<400> SEQUENCE: 70

Glu Ser Asp Asn His Thr Ala Pro Ile
1               5

<210> SEQ ID NO 71
<211> LENGTH: 9
<212> TYPE: PRT
<213> ORGANISM: Homo sapiens

<400> SEQUENCE: 71

Glu Ser Asp Asn His Thr Thr Pro Ile

-continued

```
     1               5

<210> SEQ ID NO 72
<211> LENGTH: 9
<212> TYPE: PRT
<213> ORGANISM: Homo sapiens

<400> SEQUENCE: 72

Glu Ser Gln Pro Ala Ile Arg Asn Gln
  1               5

<210> SEQ ID NO 73
<211> LENGTH: 9
<212> TYPE: PRT
<213> ORGANISM: Homo sapiens

<400> SEQUENCE: 73

Glu Thr Ser Glu Lys Arg Pro Phe Met
  1               5

<210> SEQ ID NO 74
<211> LENGTH: 9
<212> TYPE: PRT
<213> ORGANISM: Homo sapiens

<400> SEQUENCE: 74

Phe Ala Pro Pro Gly Ala Ser Ala Tyr
  1               5

<210> SEQ ID NO 75
<211> LENGTH: 9
<212> TYPE: PRT
<213> ORGANISM: Homo sapiens

<400> SEQUENCE: 75

Phe Ala Arg Ser Asp Glu Leu Val Arg
  1               5

<210> SEQ ID NO 76
<211> LENGTH: 9
<212> TYPE: PRT
<213> ORGANISM: Homo sapiens

<400> SEQUENCE: 76

Phe Gly Pro Pro Pro Ser Gln Ala
  1               5

<210> SEQ ID NO 77
<211> LENGTH: 9
<212> TYPE: PRT
<213> ORGANISM: Homo sapiens

<400> SEQUENCE: 77

Phe Lys Asp Cys Glu Arg Arg Phe Ser
  1               5

<210> SEQ ID NO 78
<211> LENGTH: 9
<212> TYPE: PRT
<213> ORGANISM: Homo sapiens

<400> SEQUENCE: 78

Phe Lys Leu Ser His Leu Gln Met His
  1               5
```

```
<210> SEQ ID NO 79
<211> LENGTH: 9
<212> TYPE: PRT
<213> ORGANISM: Homo sapiens

<400> SEQUENCE: 79

Phe Pro Asn Ala Pro Tyr Leu Pro Ser
 1               5

<210> SEQ ID NO 80
<211> LENGTH: 9
<212> TYPE: PRT
<213> ORGANISM: Homo sapiens

<400> SEQUENCE: 80

Phe Gln Cys Lys Thr Cys Gln Arg Lys
 1               5

<210> SEQ ID NO 81
<211> LENGTH: 9
<212> TYPE: PRT
<213> ORGANISM: Homo sapiens

<400> SEQUENCE: 81

Phe Arg Gly Ile Gln Asp Val Arg Arg
 1               5

<210> SEQ ID NO 82
<211> LENGTH: 9
<212> TYPE: PRT
<213> ORGANISM: Homo sapiens

<400> SEQUENCE: 82

Phe Ser Gly Gln Phe Thr Gly Thr Ala
 1               5

<210> SEQ ID NO 83
<211> LENGTH: 9
<212> TYPE: PRT
<213> ORGANISM: Homo sapiens

<400> SEQUENCE: 83

Phe Ser Arg Ser Asp Gln Leu Lys Arg
 1               5

<210> SEQ ID NO 84
<211> LENGTH: 9
<212> TYPE: PRT
<213> ORGANISM: Homo sapiens

<400> SEQUENCE: 84

Phe Thr Gly Thr Ala Gly Ala Cys Arg
 1               5

<210> SEQ ID NO 85
<211> LENGTH: 9
<212> TYPE: PRT
<213> ORGANISM: Homo sapiens

<400> SEQUENCE: 85

Phe Thr Val His Phe Ser Gly Gln Phe
 1               5

<210> SEQ ID NO 86
```

```
<211> LENGTH: 9
<212> TYPE: PRT
<213> ORGANISM: Homo sapiens

<400> SEQUENCE: 86

Gly Ala Ala Gln Trp Ala Pro Val Leu
 1               5

<210> SEQ ID NO 87
<211> LENGTH: 9
<212> TYPE: PRT
<213> ORGANISM: Homo sapiens

<400> SEQUENCE: 87

Gly Ala Glu Pro His Glu Glu Gln Cys
 1               5

<210> SEQ ID NO 88
<211> LENGTH: 9
<212> TYPE: PRT
<213> ORGANISM: Homo sapiens

<400> SEQUENCE: 88

Gly Ala Thr Leu Lys Gly Val Ala Ala
 1               5

<210> SEQ ID NO 89
<211> LENGTH: 9
<212> TYPE: PRT
<213> ORGANISM: Homo sapiens

<400> SEQUENCE: 89

Gly Cys Ala Leu Pro Val Ser Gly Ala
 1               5

<210> SEQ ID NO 90
<211> LENGTH: 9
<212> TYPE: PRT
<213> ORGANISM: Homo sapiens

<400> SEQUENCE: 90

Gly Cys Asn Lys Arg Tyr Phe Lys Leu
 1               5

<210> SEQ ID NO 91
<211> LENGTH: 9
<212> TYPE: PRT
<213> ORGANISM: Homo sapiens

<400> SEQUENCE: 91

Gly Glu Lys Pro Tyr Gln Cys Asp Phe
 1               5

<210> SEQ ID NO 92
<211> LENGTH: 9
<212> TYPE: PRT
<213> ORGANISM: Homo sapiens

<400> SEQUENCE: 92

Gly Gly Gly Gly Cys Ala Leu Pro Val
 1               5

<210> SEQ ID NO 93
<211> LENGTH: 9
<212> TYPE: PRT
```

```
<213> ORGANISM: Homo sapiens

<400> SEQUENCE: 93

Gly Gly Pro Ala Pro Pro Ala Pro
 1               5

<210> SEQ ID NO 94
<211> LENGTH: 9
<212> TYPE: PRT
<213> ORGANISM: Homo sapiens

<400> SEQUENCE: 94

Gly His Thr Pro Ser His His Ala Ala
 1               5

<210> SEQ ID NO 95
<211> LENGTH: 9
<212> TYPE: PRT
<213> ORGANISM: Homo sapiens

<400> SEQUENCE: 95

Gly Lys Thr Ser Glu Lys Pro Phe Ser
 1               5

<210> SEQ ID NO 96
<211> LENGTH: 9
<212> TYPE: PRT
<213> ORGANISM: Homo sapiens

<400> SEQUENCE: 96

Gly Pro Phe Gly Pro Pro Pro Ser
 1               5

<210> SEQ ID NO 97
<211> LENGTH: 9
<212> TYPE: PRT
<213> ORGANISM: Homo sapiens

<400> SEQUENCE: 97

Gly Pro Pro Pro Ser Gln Ala Ser
 1               5

<210> SEQ ID NO 98
<211> LENGTH: 9
<212> TYPE: PRT
<213> ORGANISM: Homo sapiens

<400> SEQUENCE: 98

Gly Gln Ala Arg Met Phe Pro Asn Ala
 1               5

<210> SEQ ID NO 99
<211> LENGTH: 9
<212> TYPE: PRT
<213> ORGANISM: Homo sapiens

<400> SEQUENCE: 99

Gly Gln Phe Thr Gly Thr Ala Gly Ala
 1               5

<210> SEQ ID NO 100
<211> LENGTH: 9
<212> TYPE: PRT
<213> ORGANISM: Homo sapiens
```

```
<400> SEQUENCE: 100

Gly Gln Ser Asn His Ser Thr Gly Tyr
 1               5

<210> SEQ ID NO 101
<211> LENGTH: 9
<212> TYPE: PRT
<213> ORGANISM: Homo sapiens

<400> SEQUENCE: 101

Gly Ser Asp Val Arg Asp Leu Asn Ala
 1               5

<210> SEQ ID NO 102
<211> LENGTH: 9
<212> TYPE: PRT
<213> ORGANISM: Homo sapiens

<400> SEQUENCE: 102

Gly Ser Gln Ala Leu Leu Leu Arg Thr
 1               5

<210> SEQ ID NO 103
<211> LENGTH: 9
<212> TYPE: PRT
<213> ORGANISM: Homo sapiens

<400> SEQUENCE: 103

Gly Val Phe Arg Gly Ile Gln Asp Val
 1               5

<210> SEQ ID NO 104
<211> LENGTH: 9
<212> TYPE: PRT
<213> ORGANISM: Homo sapiens

<400> SEQUENCE: 104

Gly Val Lys Pro Phe Gln Cys Lys Thr
 1               5

<210> SEQ ID NO 105
<211> LENGTH: 9
<212> TYPE: PRT
<213> ORGANISM: Homo sapiens

<400> SEQUENCE: 105

Gly Tyr Glu Ser Asp Asn His Thr Ala
 1               5

<210> SEQ ID NO 106
<211> LENGTH: 9
<212> TYPE: PRT
<213> ORGANISM: Homo sapiens

<400> SEQUENCE: 106

Gly Tyr Glu Ser Asp Asn His Thr Thr
 1               5

<210> SEQ ID NO 107
<211> LENGTH: 9
<212> TYPE: PRT
<213> ORGANISM: Homo sapiens

<400> SEQUENCE: 107
```

His Glu Gln Cys Leu Ser Ala Phe
1               5

<210> SEQ ID NO 108
<211> LENGTH: 9
<212> TYPE: PRT
<213> ORGANISM: Homo sapiens

<400> SEQUENCE: 108

His His Asn Met His Gln Arg Asn Met
1               5

<210> SEQ ID NO 109
<211> LENGTH: 9
<212> TYPE: PRT
<213> ORGANISM: Homo sapiens

<400> SEQUENCE: 109

His Gln Arg Arg His Thr Gly Val Lys
1               5

<210> SEQ ID NO 110
<211> LENGTH: 9
<212> TYPE: PRT
<213> ORGANISM: Homo sapiens

<400> SEQUENCE: 110

His Ser Phe Lys His Glu Asp Pro Met
1               5

<210> SEQ ID NO 111
<211> LENGTH: 9
<212> TYPE: PRT
<213> ORGANISM: Homo sapiens

<400> SEQUENCE: 111

His Ser Arg Lys His Thr Gly Glu Lys
1               5

<210> SEQ ID NO 112
<211> LENGTH: 9
<212> TYPE: PRT
<213> ORGANISM: Homo sapiens

<400> SEQUENCE: 112

His Thr Gly Glu Lys Pro Tyr Gln Cys
1               5

<210> SEQ ID NO 113
<211> LENGTH: 9
<212> TYPE: PRT
<213> ORGANISM: Homo sapiens

<400> SEQUENCE: 113

His Thr His Gly Val Phe Arg Gly Ile
1               5

<210> SEQ ID NO 114
<211> LENGTH: 9
<212> TYPE: PRT
<213> ORGANISM: Homo sapiens

<400> SEQUENCE: 114

His Thr Arg Thr His Thr Gly Lys Thr
1               5

<210> SEQ ID NO 115
<211> LENGTH: 9
<212> TYPE: PRT
<213> ORGANISM: Homo sapiens

<400> SEQUENCE: 115

His Thr Thr Pro Ile Leu Cys Gly Ala
 1               5

<210> SEQ ID NO 116
<211> LENGTH: 9
<212> TYPE: PRT
<213> ORGANISM: Homo sapiens

<400> SEQUENCE: 116

Ile Leu Cys Gly Ala Gln Tyr Arg Ile
 1               5

<210> SEQ ID NO 117
<211> LENGTH: 9
<212> TYPE: PRT
<213> ORGANISM: Homo sapiens

<400> SEQUENCE: 117

Ile Arg Asn Gln Gly Tyr Ser Thr Val
 1               5

<210> SEQ ID NO 118
<211> LENGTH: 9
<212> TYPE: PRT
<213> ORGANISM: Homo sapiens

<400> SEQUENCE: 118

Lys Asp Cys Glu Arg Arg Phe Ser Arg
 1               5

<210> SEQ ID NO 119
<211> LENGTH: 9
<212> TYPE: PRT
<213> ORGANISM: Homo sapiens

<400> SEQUENCE: 119

Lys Phe Ala Arg Ser Asp Glu Leu Val
 1               5

<210> SEQ ID NO 120
<211> LENGTH: 9
<212> TYPE: PRT
<213> ORGANISM: Homo sapiens

<400> SEQUENCE: 120

Lys Phe Ser Arg Ser Asp His Leu Lys
 1               5

<210> SEQ ID NO 121
<211> LENGTH: 9
<212> TYPE: PRT
<213> ORGANISM: Homo sapiens

<400> SEQUENCE: 121

Lys His Glu Asp Pro Met Gly Gln Gln
 1               5

<210> SEQ ID NO 122
<211> LENGTH: 9
<212> TYPE: PRT
<213> ORGANISM: Homo sapiens

<400> SEQUENCE: 122

Lys Lys Phe Ala Arg Ser Asp Glu Leu
 1               5

<210> SEQ ID NO 123
<211> LENGTH: 9
<212> TYPE: PRT
<213> ORGANISM: Homo sapiens

<400> SEQUENCE: 123

Lys Pro Phe Ser Cys Arg Trp Pro Ser
 1               5

<210> SEQ ID NO 124
<211> LENGTH: 9
<212> TYPE: PRT
<213> ORGANISM: Homo sapiens

<400> SEQUENCE: 124

Lys Pro Tyr Gln Cys Asp Phe Lys Asp
 1               5

<210> SEQ ID NO 125
<211> LENGTH: 9
<212> TYPE: PRT
<213> ORGANISM: Homo sapiens

<400> SEQUENCE: 125

Lys Gln Glu Pro Ser Trp Gly Gly Ala
 1               5

<210> SEQ ID NO 126
<211> LENGTH: 9
<212> TYPE: PRT
<213> ORGANISM: Homo sapiens

<400> SEQUENCE: 126

Lys Arg His Gln Arg Arg His Thr Gly
 1               5

<210> SEQ ID NO 127
<211> LENGTH: 9
<212> TYPE: PRT
<213> ORGANISM: Homo sapiens

<400> SEQUENCE: 127

Lys Arg Tyr Phe Lys Leu Ser His Leu
 1               5

<210> SEQ ID NO 128
<211> LENGTH: 9
<212> TYPE: PRT
<213> ORGANISM: Homo sapiens

<400> SEQUENCE: 128

Lys Thr Cys Gln Arg Lys Phe Ser Arg
 1               5

<210> SEQ ID NO 129
<211> LENGTH: 9

```
<212> TYPE: PRT
<213> ORGANISM: Homo sapiens

<400> SEQUENCE: 129

Lys Thr Ser Glu Lys Pro Phe Ser Cys
 1               5

<210> SEQ ID NO 130
<211> LENGTH: 9
<212> TYPE: PRT
<213> ORGANISM: Homo sapiens

<400> SEQUENCE: 130

Leu Asp Phe Ala Pro Pro Gly Ala Ser
 1               5

<210> SEQ ID NO 131
<211> LENGTH: 9
<212> TYPE: PRT
<213> ORGANISM: Homo sapiens

<400> SEQUENCE: 131

Leu Glu Cys Met Thr Trp Asn Gln Met
 1               5

<210> SEQ ID NO 132
<211> LENGTH: 9
<212> TYPE: PRT
<213> ORGANISM: Homo sapiens

<400> SEQUENCE: 132

Leu Glu Ser Gln Pro Ala Ile Arg Asn
 1               5

<210> SEQ ID NO 133
<211> LENGTH: 9
<212> TYPE: PRT
<213> ORGANISM: Homo sapiens

<400> SEQUENCE: 133

Leu Gly Ala Thr Leu Lys Gly Val Ala
 1               5

<210> SEQ ID NO 134
<211> LENGTH: 9
<212> TYPE: PRT
<213> ORGANISM: Homo sapiens

<400> SEQUENCE: 134

Leu Gly Gly Gly Gly Gly Cys Ala Leu
 1               5

<210> SEQ ID NO 135
<211> LENGTH: 9
<212> TYPE: PRT
<213> ORGANISM: Homo sapiens

<400> SEQUENCE: 135

Leu Lys Gly Val Ala Ala Gly Ser Ser
 1               5

<210> SEQ ID NO 136
<211> LENGTH: 9
<212> TYPE: PRT
<213> ORGANISM: Homo sapiens
```

```
<400> SEQUENCE: 136

Leu Lys Arg His Gln Arg Arg His Thr
 1               5

<210> SEQ ID NO 137
<211> LENGTH: 9
<212> TYPE: PRT
<213> ORGANISM: Homo sapiens

<400> SEQUENCE: 137

Leu Lys Thr His Thr Arg Thr His Thr
 1               5

<210> SEQ ID NO 138
<211> LENGTH: 9
<212> TYPE: PRT
<213> ORGANISM: Homo sapiens

<400> SEQUENCE: 138

Leu Pro Val Ser Gly Ala Ala Gln Trp
 1               5

<210> SEQ ID NO 139
<211> LENGTH: 9
<212> TYPE: PRT
<213> ORGANISM: Homo sapiens

<400> SEQUENCE: 139

Leu Gln Met His Ser Arg Lys His Thr
 1               5

<210> SEQ ID NO 140
<211> LENGTH: 9
<212> TYPE: PRT
<213> ORGANISM: Homo sapiens

<400> SEQUENCE: 140

Leu Arg Thr Pro Tyr Ser Ser Asp Asn
 1               5

<210> SEQ ID NO 141
<211> LENGTH: 9
<212> TYPE: PRT
<213> ORGANISM: Homo sapiens

<400> SEQUENCE: 141

Leu Ser His Leu Gln Met His Ser Arg
 1               5

<210> SEQ ID NO 142
<211> LENGTH: 9
<212> TYPE: PRT
<213> ORGANISM: Homo sapiens

<400> SEQUENCE: 142

Met Cys Ala Tyr Pro Gly Cys Asn Lys
 1               5

<210> SEQ ID NO 143
<211> LENGTH: 9
<212> TYPE: PRT
<213> ORGANISM: Homo sapiens

<400> SEQUENCE: 143
```

Met His Gln Arg Asn Met Thr Lys Leu
1               5

<210> SEQ ID NO 144
<211> LENGTH: 9
<212> TYPE: PRT
<213> ORGANISM: Homo sapiens

<400> SEQUENCE: 144

Asn Ala Pro Tyr Leu Pro Ser Cys Leu
1               5

<210> SEQ ID NO 145
<211> LENGTH: 9
<212> TYPE: PRT
<213> ORGANISM: Homo sapiens

<400> SEQUENCE: 145

Asn Lys Arg Tyr Phe Lys Leu Ser His
1               5

<210> SEQ ID NO 146
<211> LENGTH: 9
<212> TYPE: PRT
<213> ORGANISM: Homo sapiens

<400> SEQUENCE: 146

Asn Leu Gly Ala Thr Leu Lys Gly Val
1               5

<210> SEQ ID NO 147
<211> LENGTH: 9
<212> TYPE: PRT
<213> ORGANISM: Homo sapiens

<400> SEQUENCE: 147

Asn Leu Tyr Gln Met Thr Ser Gln Leu
1               5

<210> SEQ ID NO 148
<211> LENGTH: 9
<212> TYPE: PRT
<213> ORGANISM: Homo sapiens

<400> SEQUENCE: 148

Asn Met His Gln Arg Asn Met Thr Lys
1               5

<210> SEQ ID NO 149
<211> LENGTH: 9
<212> TYPE: PRT
<213> ORGANISM: Homo sapiens

<400> SEQUENCE: 149

Asn Met Thr Lys Leu Gln Leu Ala Leu
1               5

<210> SEQ ID NO 150
<211> LENGTH: 9
<212> TYPE: PRT
<213> ORGANISM: Homo sapiens

<400> SEQUENCE: 150

Asn Gln Gly Tyr Ser Thr Val Thr Phe

-continued

<210> SEQ ID NO 151
<211> LENGTH: 9
<212> TYPE: PRT
<213> ORGANISM: Homo sapiens

<400> SEQUENCE: 151

Asn Gln Met Asn Leu Gly Ala Thr Leu
 1               5

<210> SEQ ID NO 152
<211> LENGTH: 9
<212> TYPE: PRT
<213> ORGANISM: Homo sapiens

<400> SEQUENCE: 152

Pro Ala Ile Arg Asn Gln Gly Tyr Ser
 1               5

<210> SEQ ID NO 153
<211> LENGTH: 9
<212> TYPE: PRT
<213> ORGANISM: Homo sapiens

<400> SEQUENCE: 153

Pro Gly Ala Ser Ala Tyr Gly Ser Leu
 1               5

<210> SEQ ID NO 154
<211> LENGTH: 9
<212> TYPE: PRT
<213> ORGANISM: Homo sapiens

<400> SEQUENCE: 154

Pro His Glu Glu Gln Cys Leu Ser Ala
 1               5

<210> SEQ ID NO 155
<211> LENGTH: 9
<212> TYPE: PRT
<213> ORGANISM: Homo sapiens

<400> SEQUENCE: 155

Pro Ile Leu Cys Gly Ala Gln Tyr Arg
 1               5

<210> SEQ ID NO 156
<211> LENGTH: 9
<212> TYPE: PRT
<213> ORGANISM: Homo sapiens

<400> SEQUENCE: 156

Pro Pro Pro Pro His Ser Phe Ile Lys
 1               5

<210> SEQ ID NO 157
<211> LENGTH: 9
<212> TYPE: PRT
<213> ORGANISM: Homo sapiens

<400> SEQUENCE: 157

Pro Pro Pro Pro Pro His Ser Phe Ile
 1               5

```
<210> SEQ ID NO 158
<211> LENGTH: 9
<212> TYPE: PRT
<213> ORGANISM: Homo sapiens

<400> SEQUENCE: 158

Pro Pro Pro Pro Pro Pro His Ser Phe
 1               5

<210> SEQ ID NO 159
<211> LENGTH: 9
<212> TYPE: PRT
<213> ORGANISM: Homo sapiens

<400> SEQUENCE: 159

Pro Ser Cys Gln Lys Lys Phe Ala Arg
 1               5

<210> SEQ ID NO 160
<211> LENGTH: 9
<212> TYPE: PRT
<213> ORGANISM: Homo sapiens

<400> SEQUENCE: 160

Gln Ala Leu Leu Leu Arg Thr Pro Tyr
 1               5

<210> SEQ ID NO 161
<211> LENGTH: 9
<212> TYPE: PRT
<213> ORGANISM: Homo sapiens

<400> SEQUENCE: 161

Gln Ala Ser Ser Gly Gln Ala Arg Met
 1               5

<210> SEQ ID NO 162
<211> LENGTH: 9
<212> TYPE: PRT
<213> ORGANISM: Homo sapiens

<400> SEQUENCE: 162

Gln Cys Asp Phe Lys Asp Cys Glu Arg
 1               5

<210> SEQ ID NO 163
<211> LENGTH: 9
<212> TYPE: PRT
<213> ORGANISM: Homo sapiens

<400> SEQUENCE: 163

Gln Cys Lys Thr Cys Gln Arg Lys Phe
 1               5

<210> SEQ ID NO 164
<211> LENGTH: 9
<212> TYPE: PRT
<213> ORGANISM: Homo sapiens

<400> SEQUENCE: 164

Gln Asp Val Arg Arg Val Pro Gly Val
 1               5

<210> SEQ ID NO 165
```

-continued

```
<211> LENGTH: 9
<212> TYPE: PRT
<213> ORGANISM: Homo sapiens

<400> SEQUENCE: 165

Gln Phe Thr Gly Thr Ala Gly Ala Cys
  1               5

<210> SEQ ID NO 166
<211> LENGTH: 9
<212> TYPE: PRT
<213> ORGANISM: Homo sapiens

<400> SEQUENCE: 166

Gln Gly Ser Leu Gly Glu Gln Gln Tyr
  1               5

<210> SEQ ID NO 167
<211> LENGTH: 9
<212> TYPE: PRT
<213> ORGANISM: Homo sapiens

<400> SEQUENCE: 167

Gln Leu Glu Cys Met Thr Trp Asn Gln
  1               5

<210> SEQ ID NO 168
<211> LENGTH: 9
<212> TYPE: PRT
<213> ORGANISM: Homo sapiens

<400> SEQUENCE: 168

Gln Met Asn Leu Gly Ala Thr Leu Lys
  1               5

<210> SEQ ID NO 169
<211> LENGTH: 9
<212> TYPE: PRT
<213> ORGANISM: Homo sapiens

<400> SEQUENCE: 169

Gln Met Thr Ser Gln Leu Glu Cys Met
  1               5

<210> SEQ ID NO 170
<211> LENGTH: 9
<212> TYPE: PRT
<213> ORGANISM: Homo sapiens

<400> SEQUENCE: 170

Gln Pro Ala Ile Arg Asn Gln Gly Tyr
  1               5

<210> SEQ ID NO 171
<211> LENGTH: 9
<212> TYPE: PRT
<213> ORGANISM: Homo sapiens

<400> SEQUENCE: 171

Gln Gln Tyr Ser Val Pro Pro Pro Val
  1               5

<210> SEQ ID NO 172
<211> LENGTH: 9
<212> TYPE: PRT
```

<213> ORGANISM: Homo sapiens

<400> SEQUENCE: 172

Gln Arg Lys Phe Ser Arg Ser Asp His
 1               5

<210> SEQ ID NO 173
<211> LENGTH: 9
<212> TYPE: PRT
<213> ORGANISM: Homo sapiens

<400> SEQUENCE: 173

Gln Arg Asn Met Thr Lys Leu Gln Leu
 1               5

<210> SEQ ID NO 174
<211> LENGTH: 9
<212> TYPE: PRT
<213> ORGANISM: Homo sapiens

<400> SEQUENCE: 174

Gln Trp Ala Pro Val Leu Asp Phe Ala
 1               5

<210> SEQ ID NO 175
<211> LENGTH: 9
<212> TYPE: PRT
<213> ORGANISM: Homo sapiens

<400> SEQUENCE: 175

Gln Tyr Arg Ile His Thr His Gly Val
 1               5

<210> SEQ ID NO 176
<211> LENGTH: 9
<212> TYPE: PRT
<213> ORGANISM: Homo sapiens

<400> SEQUENCE: 176

Gln Tyr Ser Val Pro Pro Pro Val Tyr
 1               5

<210> SEQ ID NO 177
<211> LENGTH: 9
<212> TYPE: PRT
<213> ORGANISM: Homo sapiens

<400> SEQUENCE: 177

Arg Asp Leu Asn Ala Leu Leu Pro Ala
 1               5

<210> SEQ ID NO 178
<211> LENGTH: 9
<212> TYPE: PRT
<213> ORGANISM: Homo sapiens

<400> SEQUENCE: 178

Arg Phe Ser Arg Ser Asp Gln Leu Lys
 1               5

<210> SEQ ID NO 179
<211> LENGTH: 9
<212> TYPE: PRT
<213> ORGANISM: Homo sapiens

```
<400> SEQUENCE: 179

Arg Gly Ile Gln Asp Val Arg Arg Val
 1               5

<210> SEQ ID NO 180
<211> LENGTH: 9
<212> TYPE: PRT
<213> ORGANISM: Homo sapiens

<400> SEQUENCE: 180

Arg His His Asn Met His Gln Arg Asn
 1               5

<210> SEQ ID NO 181
<211> LENGTH: 9
<212> TYPE: PRT
<213> ORGANISM: Homo sapiens

<400> SEQUENCE: 181

Arg His Gln Arg Arg His Thr Gly Val
 1               5

<210> SEQ ID NO 182
<211> LENGTH: 9
<212> TYPE: PRT
<213> ORGANISM: Homo sapiens

<400> SEQUENCE: 182

Arg Ile His Thr His Gly Val Phe Arg
 1               5

<210> SEQ ID NO 183
<211> LENGTH: 9
<212> TYPE: PRT
<213> ORGANISM: Homo sapiens

<400> SEQUENCE: 183

Arg Lys Phe Ser Arg Ser Asp His Leu
 1               5

<210> SEQ ID NO 184
<211> LENGTH: 9
<212> TYPE: PRT
<213> ORGANISM: Homo sapiens

<400> SEQUENCE: 184

Arg Lys His Thr Gly Glu Lys Pro Tyr
 1               5

<210> SEQ ID NO 185
<211> LENGTH: 9
<212> TYPE: PRT
<213> ORGANISM: Homo sapiens

<400> SEQUENCE: 185

Arg Met Phe Pro Asn Ala Pro Tyr Leu
 1               5

<210> SEQ ID NO 186
<211> LENGTH: 9
<212> TYPE: PRT
<213> ORGANISM: Homo sapiens

<400> SEQUENCE: 186
```

Arg Asn Met Thr Lys Leu Gln Leu Ala
1               5

<210> SEQ ID NO 187
<211> LENGTH: 9
<212> TYPE: PRT
<213> ORGANISM: Homo sapiens

<400> SEQUENCE: 187

Arg Arg Phe Ser Arg Ser Asp Gln Leu
1               5

<210> SEQ ID NO 188
<211> LENGTH: 9
<212> TYPE: PRT
<213> ORGANISM: Homo sapiens

<400> SEQUENCE: 188

Arg Arg His Thr Gly Val Lys Pro Phe
1               5

<210> SEQ ID NO 189
<211> LENGTH: 9
<212> TYPE: PRT
<213> ORGANISM: Homo sapiens

<400> SEQUENCE: 189

Arg Arg Val Pro Gly Val Ala Pro Thr
1               5

<210> SEQ ID NO 190
<211> LENGTH: 9
<212> TYPE: PRT
<213> ORGANISM: Homo sapiens

<400> SEQUENCE: 190

Arg Ser Ala Ser Glu Thr Ser Glu Lys
1               5

<210> SEQ ID NO 191
<211> LENGTH: 9
<212> TYPE: PRT
<213> ORGANISM: Homo sapiens

<400> SEQUENCE: 191

Arg Ser Asp Glu Leu Val Arg His His
1               5

<210> SEQ ID NO 192
<211> LENGTH: 9
<212> TYPE: PRT
<213> ORGANISM: Homo sapiens

<400> SEQUENCE: 192

Arg Ser Asp His Leu Lys Thr His Thr
1               5

<210> SEQ ID NO 193
<211> LENGTH: 9
<212> TYPE: PRT
<213> ORGANISM: Homo sapiens

<400> SEQUENCE: 193

Arg Ser Asp Gln Leu Lys Arg His Gln
1               5

<210> SEQ ID NO 194
<211> LENGTH: 9
<212> TYPE: PRT
<213> ORGANISM: Homo sapiens

<400> SEQUENCE: 194

Arg Thr Pro Tyr Ser Ser Asp Asn Leu
 1               5

<210> SEQ ID NO 195
<211> LENGTH: 9
<212> TYPE: PRT
<213> ORGANISM: Homo sapiens

<400> SEQUENCE: 195

Arg Val Pro Gly Val Ala Pro Thr Leu
 1               5

<210> SEQ ID NO 196
<211> LENGTH: 9
<212> TYPE: PRT
<213> ORGANISM: Homo sapiens

<400> SEQUENCE: 196

Arg Trp Pro Ser Cys Gln Lys Lys Phe
 1               5

<210> SEQ ID NO 197
<211> LENGTH: 9
<212> TYPE: PRT
<213> ORGANISM: Homo sapiens

<400> SEQUENCE: 197

Ser Ala Ser Glu Thr Ser Glu Lys Arg
 1               5

<210> SEQ ID NO 198
<211> LENGTH: 9
<212> TYPE: PRT
<213> ORGANISM: Homo sapiens

<400> SEQUENCE: 198

Ser Cys Leu Glu Ser Gln Pro Ala Ile
 1               5

<210> SEQ ID NO 199
<211> LENGTH: 9
<212> TYPE: PRT
<213> ORGANISM: Homo sapiens

<400> SEQUENCE: 199

Ser Cys Leu Glu Ser Gln Pro Thr Ile
 1               5

<210> SEQ ID NO 200
<211> LENGTH: 9
<212> TYPE: PRT
<213> ORGANISM: Homo sapiens

<400> SEQUENCE: 200

Ser Cys Gln Lys Lys Phe Ala Arg Ser
 1               5

-continued

```
<210> SEQ ID NO 201
<211> LENGTH: 9
<212> TYPE: PRT
<213> ORGANISM: Homo sapiens

<400> SEQUENCE: 201

Ser Cys Arg Trp Pro Ser Cys Gln Lys
 1               5

<210> SEQ ID NO 202
<211> LENGTH: 9
<212> TYPE: PRT
<213> ORGANISM: Homo sapiens

<400> SEQUENCE: 202

Ser Cys Thr Gly Ser Gln Ala Leu Leu
 1               5

<210> SEQ ID NO 203
<211> LENGTH: 9
<212> TYPE: PRT
<213> ORGANISM: Homo sapiens

<400> SEQUENCE: 203

Ser Asp Glu Leu Val Arg His His Asn
 1               5

<210> SEQ ID NO 204
<211> LENGTH: 9
<212> TYPE: PRT
<213> ORGANISM: Homo sapiens

<400> SEQUENCE: 204

Ser Asp Asn His Thr Thr Pro Ile Leu
 1               5

<210> SEQ ID NO 205
<211> LENGTH: 9
<212> TYPE: PRT
<213> ORGANISM: Homo sapiens

<400> SEQUENCE: 205

Ser Asp Asn Leu Tyr Gln Met Thr Ser
 1               5

<210> SEQ ID NO 206
<211> LENGTH: 9
<212> TYPE: PRT
<213> ORGANISM: Homo sapiens

<400> SEQUENCE: 206

Ser Asp Val Arg Asp Leu Asn Ala Leu
 1               5

<210> SEQ ID NO 207
<211> LENGTH: 9
<212> TYPE: PRT
<213> ORGANISM: Homo sapiens

<400> SEQUENCE: 207

Ser Glu Lys Pro Phe Ser Cys Arg Trp
 1               5

<210> SEQ ID NO 208
<211> LENGTH: 9
```

```
<212> TYPE: PRT
<213> ORGANISM: Homo sapiens

<400> SEQUENCE: 208

Ser Glu Lys Arg Pro Phe Met Cys Ala
 1               5

<210> SEQ ID NO 209
<211> LENGTH: 9
<212> TYPE: PRT
<213> ORGANISM: Homo sapiens

<400> SEQUENCE: 209

Ser Glu Thr Ser Glu Lys Arg Pro Phe
 1               5

<210> SEQ ID NO 210
<211> LENGTH: 9
<212> TYPE: PRT
<213> ORGANISM: Homo sapiens

<400> SEQUENCE: 210

Ser Phe Ile Lys Gln Glu Pro Ser Trp
 1               5

<210> SEQ ID NO 211
<211> LENGTH: 9
<212> TYPE: PRT
<213> ORGANISM: Homo sapiens

<400> SEQUENCE: 211

Ser Gly Ala Ala Gln Trp Ala Pro Val
 1               5

<210> SEQ ID NO 212
<211> LENGTH: 9
<212> TYPE: PRT
<213> ORGANISM: Homo sapiens

<400> SEQUENCE: 212

Ser Gly Gln Ala Arg Met Phe Pro Asn
 1               5

<210> SEQ ID NO 213
<211> LENGTH: 9
<212> TYPE: PRT
<213> ORGANISM: Homo sapiens

<400> SEQUENCE: 213

Ser His His Ala Ala Gln Phe Pro Asn
 1               5

<210> SEQ ID NO 214
<211> LENGTH: 9
<212> TYPE: PRT
<213> ORGANISM: Homo sapiens

<400> SEQUENCE: 214

Ser Leu Gly Glu Gln Gln Tyr Ser Val
 1               5

<210> SEQ ID NO 215
<211> LENGTH: 9
<212> TYPE: PRT
<213> ORGANISM: Homo sapiens
```

```
<400> SEQUENCE: 215

Ser Leu Gly Gly Gly Gly Cys Ala
 1               5

<210> SEQ ID NO 216
<211> LENGTH: 9
<212> TYPE: PRT
<213> ORGANISM: Homo sapiens

<400> SEQUENCE: 216

Ser Gln Ala Ser Ser Gly Gln Ala Arg
 1               5

<210> SEQ ID NO 217
<211> LENGTH: 9
<212> TYPE: PRT
<213> ORGANISM: Homo sapiens

<400> SEQUENCE: 217

Ser Ser Asp Asn Leu Tyr Gln Met Thr
 1               5

<210> SEQ ID NO 218
<211> LENGTH: 9
<212> TYPE: PRT
<213> ORGANISM: Homo sapiens

<400> SEQUENCE: 218

Ser Val Pro Pro Pro Val Tyr Gly Cys
 1               5

<210> SEQ ID NO 219
<211> LENGTH: 9
<212> TYPE: PRT
<213> ORGANISM: Homo sapiens

<400> SEQUENCE: 219

Thr Cys Gln Arg Lys Phe Ser Arg Ser
 1               5

<210> SEQ ID NO 220
<211> LENGTH: 9
<212> TYPE: PRT
<213> ORGANISM: Homo sapiens

<400> SEQUENCE: 220

Thr Asp Ser Cys Thr Gly Ser Gln Ala
 1               5

<210> SEQ ID NO 221
<211> LENGTH: 9
<212> TYPE: PRT
<213> ORGANISM: Homo sapiens

<400> SEQUENCE: 221

Thr Glu Gly Gln Ser Asn His Ser Thr
 1               5

<210> SEQ ID NO 222
<211> LENGTH: 9
<212> TYPE: PRT
<213> ORGANISM: Homo sapiens

<400> SEQUENCE: 222
```

```
Thr Gly Lys Thr Ser Glu Lys Pro Phe
  1               5
```

<210> SEQ ID NO 223
<211> LENGTH: 9
<212> TYPE: PRT
<213> ORGANISM: Homo sapiens

<400> SEQUENCE: 223

```
Thr Gly Ser Gln Ala Leu Leu Leu Arg
  1               5
```

<210> SEQ ID NO 224
<211> LENGTH: 9
<212> TYPE: PRT
<213> ORGANISM: Homo sapiens

<400> SEQUENCE: 224

```
Thr Gly Thr Ala Gly Ala Cys Arg Tyr
  1               5
```

<210> SEQ ID NO 225
<211> LENGTH: 9
<212> TYPE: PRT
<213> ORGANISM: Homo sapiens

<400> SEQUENCE: 225

```
Thr Gly Tyr Glu Ser Asp Asn His Thr
  1               5
```

<210> SEQ ID NO 226
<211> LENGTH: 9
<212> TYPE: PRT
<213> ORGANISM: Homo sapiens

<400> SEQUENCE: 226

```
Thr Leu Val Arg Ser Ala Ser Glu Thr
  1               5
```

<210> SEQ ID NO 227
<211> LENGTH: 9
<212> TYPE: PRT
<213> ORGANISM: Homo sapiens

<400> SEQUENCE: 227

```
Thr Pro Ile Leu Cys Gly Ala Gln Tyr
  1               5
```

<210> SEQ ID NO 228
<211> LENGTH: 9
<212> TYPE: PRT
<213> ORGANISM: Homo sapiens

<400> SEQUENCE: 228

```
Thr Pro Ser His His Ala Ala Gln Phe
  1               5
```

<210> SEQ ID NO 229
<211> LENGTH: 9
<212> TYPE: PRT
<213> ORGANISM: Homo sapiens

<400> SEQUENCE: 229

```
Thr Pro Ser Tyr Gly His Thr Pro Ser
```

```
<210> SEQ ID NO 230
<211> LENGTH: 9
<212> TYPE: PRT
<213> ORGANISM: Homo sapiens

<400> SEQUENCE: 230

Thr Pro Thr Asp Ser Cys Thr Gly Ser
 1               5

<210> SEQ ID NO 231
<211> LENGTH: 9
<212> TYPE: PRT
<213> ORGANISM: Homo sapiens

<400> SEQUENCE: 231

Thr Pro Tyr Ser Ser Asp Asn Leu Tyr
 1               5

<210> SEQ ID NO 232
<211> LENGTH: 9
<212> TYPE: PRT
<213> ORGANISM: Homo sapiens

<400> SEQUENCE: 232

Thr Ser Glu Lys Pro Phe Ser Cys Arg
 1               5

<210> SEQ ID NO 233
<211> LENGTH: 9
<212> TYPE: PRT
<213> ORGANISM: Homo sapiens

<400> SEQUENCE: 233

Thr Ser Glu Lys Arg Pro Phe Met Cys
 1               5

<210> SEQ ID NO 234
<211> LENGTH: 9
<212> TYPE: PRT
<213> ORGANISM: Homo sapiens

<400> SEQUENCE: 234

Thr Ser Gln Leu Glu Cys Met Thr Trp
 1               5

<210> SEQ ID NO 235
<211> LENGTH: 9
<212> TYPE: PRT
<213> ORGANISM: Homo sapiens

<400> SEQUENCE: 235

Thr Val His Phe Ser Gly Gln Phe Thr
 1               5

<210> SEQ ID NO 236
<211> LENGTH: 9
<212> TYPE: PRT
<213> ORGANISM: Homo sapiens

<400> SEQUENCE: 236

Val Ala Ala Gly Ser Ser Ser Ser Val
 1               5
```

```
<210> SEQ ID NO 237
<211> LENGTH: 9
<212> TYPE: PRT
<213> ORGANISM: Homo sapiens

<400> SEQUENCE: 237

Val Ala Pro Thr Leu Val Arg Ser Ala
 1               5

<210> SEQ ID NO 238
<211> LENGTH: 9
<212> TYPE: PRT
<213> ORGANISM: Homo sapiens

<400> SEQUENCE: 238

Val Phe Arg Gly Ile Gln Asp Val Arg
 1               5

<210> SEQ ID NO 239
<211> LENGTH: 9
<212> TYPE: PRT
<213> ORGANISM: Homo sapiens

<400> SEQUENCE: 239

Val Lys Pro Phe Gln Cys Lys Thr Cys
 1               5

<210> SEQ ID NO 240
<211> LENGTH: 9
<212> TYPE: PRT
<213> ORGANISM: Homo sapiens

<400> SEQUENCE: 240

Val Lys Trp Thr Glu Gly Gln Ser Asn
 1               5

<210> SEQ ID NO 241
<211> LENGTH: 9
<212> TYPE: PRT
<213> ORGANISM: Homo sapiens

<400> SEQUENCE: 241

Val Leu Asp Phe Ala Pro Pro Gly Ala
 1               5

<210> SEQ ID NO 242
<211> LENGTH: 9
<212> TYPE: PRT
<213> ORGANISM: Homo sapiens

<400> SEQUENCE: 242

Val Pro Gly Val Ala Pro Thr Leu Val
 1               5

<210> SEQ ID NO 243
<211> LENGTH: 9
<212> TYPE: PRT
<213> ORGANISM: Homo sapiens

<400> SEQUENCE: 243

Val Arg His His Asn Met His Gln Arg
 1               5

<210> SEQ ID NO 244
```

```
<211> LENGTH: 9
<212> TYPE: PRT
<213> ORGANISM: Homo sapiens

<400> SEQUENCE: 244

Val Thr Phe Asp Gly Thr Pro Ser Tyr
 1               5

<210> SEQ ID NO 245
<211> LENGTH: 9
<212> TYPE: PRT
<213> ORGANISM: Homo sapiens

<400> SEQUENCE: 245

Trp Asn Gln Met Asn Leu Gly Ala Thr
 1               5

<210> SEQ ID NO 246
<211> LENGTH: 9
<212> TYPE: PRT
<213> ORGANISM: Homo sapiens

<400> SEQUENCE: 246

Trp Pro Ser Cys Gln Lys Lys Phe Ala
 1               5

<210> SEQ ID NO 247
<211> LENGTH: 9
<212> TYPE: PRT
<213> ORGANISM: Homo sapiens

<400> SEQUENCE: 247

Trp Thr Glu Gly Gln Ser Asn His Ser
 1               5

<210> SEQ ID NO 248
<211> LENGTH: 9
<212> TYPE: PRT
<213> ORGANISM: Homo sapiens

<400> SEQUENCE: 248

Tyr Phe Lys Leu Ser His Leu Gln Met
 1               5

<210> SEQ ID NO 249
<211> LENGTH: 9
<212> TYPE: PRT
<213> ORGANISM: Homo sapiens

<400> SEQUENCE: 249

Tyr Gly His Thr Pro Ser His His Ala
 1               5

<210> SEQ ID NO 250
<211> LENGTH: 9
<212> TYPE: PRT
<213> ORGANISM: Homo sapiens

<400> SEQUENCE: 250

Tyr Pro Gly Cys Asn Lys Arg Tyr Phe
 1               5

<210> SEQ ID NO 251
<211> LENGTH: 9
<212> TYPE: PRT
```

<213> ORGANISM: Homo sapiens

<400> SEQUENCE: 251

Tyr Gln Met Thr Ser Gln Leu Glu Cys
 1               5

<210> SEQ ID NO 252
<211> LENGTH: 9
<212> TYPE: PRT
<213> ORGANISM: Homo sapiens

<400> SEQUENCE: 252

Tyr Arg Ile His Thr His Gly Val Phe
 1               5

<210> SEQ ID NO 253
<211> LENGTH: 9
<212> TYPE: PRT
<213> ORGANISM: Homo sapiens

<400> SEQUENCE: 253

Tyr Ser Ser Asp Asn Leu Tyr Gln Met
 1               5

<210> SEQ ID NO 254
<211> LENGTH: 9
<212> TYPE: PRT
<213> ORGANISM: Mus musculus

<400> SEQUENCE: 254

Ala Glu Pro His Glu Glu Gln Cys Leu
 1               5

<210> SEQ ID NO 255
<211> LENGTH: 9
<212> TYPE: PRT
<213> ORGANISM: Mus musculus

<400> SEQUENCE: 255

Ala Leu Leu Pro Ala Val Ser Ser Leu
 1               5

<210> SEQ ID NO 256
<211> LENGTH: 9
<212> TYPE: PRT
<213> ORGANISM: Mus musculus

<400> SEQUENCE: 256

Ala Tyr Gly Ser Leu Gly Gly Pro Ala
 1               5

<210> SEQ ID NO 257
<211> LENGTH: 9
<212> TYPE: PRT
<213> ORGANISM: Mus musculus

<400> SEQUENCE: 257

Ala Tyr Pro Gly Cys Asn Lys Arg Tyr
 1               5

<210> SEQ ID NO 258
<211> LENGTH: 9
<212> TYPE: PRT
<213> ORGANISM: Mus musculus

```
<400> SEQUENCE: 258

Cys Met Thr Trp Asn Gln Met Asn Leu
 1               5

<210> SEQ ID NO 259
<211> LENGTH: 9
<212> TYPE: PRT
<213> ORGANISM: Mus musculus

<400> SEQUENCE: 259

Cys Thr Gly Ser Gln Ala Leu Leu Leu
 1               5

<210> SEQ ID NO 260
<211> LENGTH: 9
<212> TYPE: PRT
<213> ORGANISM: Mus musculus

<400> SEQUENCE: 260

Asp Gly Ala Pro Ser Tyr Gly His Thr
 1               5

<210> SEQ ID NO 261
<211> LENGTH: 9
<212> TYPE: PRT
<213> ORGANISM: Mus musculus

<400> SEQUENCE: 261

Asp Leu Asn Ala Leu Leu Pro Ala Val
 1               5

<210> SEQ ID NO 262
<211> LENGTH: 9
<212> TYPE: PRT
<213> ORGANISM: Mus musculus

<400> SEQUENCE: 262

Asp Pro Met Gly Gln Gln Gly Ser Leu
 1               5

<210> SEQ ID NO 263
<211> LENGTH: 9
<212> TYPE: PRT
<213> ORGANISM: Mus musculus

<400> SEQUENCE: 263

Asp Ser Cys Thr Gly Ser Gln Ala Leu
 1               5

<210> SEQ ID NO 264
<211> LENGTH: 9
<212> TYPE: PRT
<213> ORGANISM: Mus musculus

<400> SEQUENCE: 264

Asp Val Arg Asp Leu Asn Ala Leu Leu
 1               5

<210> SEQ ID NO 265
<211> LENGTH: 9
<212> TYPE: PRT
<213> ORGANISM: Mus musculus

<400> SEQUENCE: 265
```

```
Glu Gln Cys Leu Ser Ala Phe Thr Leu
 1               5
```

<210> SEQ ID NO 266
<211> LENGTH: 9
<212> TYPE: PRT
<213> ORGANISM: Mus musculus

<400> SEQUENCE: 266

```
Glu Ser Asp Asn His Thr Ala Pro Ile
 1               5
```

<210> SEQ ID NO 267
<211> LENGTH: 9
<212> TYPE: PRT
<213> ORGANISM: Mus musculus

<400> SEQUENCE: 267

```
Phe Pro Asn Ala Pro Tyr Leu Pro Ser
 1               5
```

<210> SEQ ID NO 268
<211> LENGTH: 9
<212> TYPE: PRT
<213> ORGANISM: Mus musculus

<400> SEQUENCE: 268

```
Gly Cys Asn Lys Arg Tyr Phe Lys Leu
 1               5
```

<210> SEQ ID NO 269
<211> LENGTH: 9
<212> TYPE: PRT
<213> ORGANISM: Mus musculus

<400> SEQUENCE: 269

```
Gly Gln Ala Arg Met Phe Pro Asn Ala
 1               5
```

<210> SEQ ID NO 270
<211> LENGTH: 9
<212> TYPE: PRT
<213> ORGANISM: Mus musculus

<400> SEQUENCE: 270

```
Gly Val Phe Arg Gly Ile Gln Asp Val
 1               5
```

<210> SEQ ID NO 271
<211> LENGTH: 9
<212> TYPE: PRT
<213> ORGANISM: Mus musculus

<400> SEQUENCE: 271

```
Gly Tyr Glu Ser Asp Asn His Thr Ala
 1               5
```

<210> SEQ ID NO 272
<211> LENGTH: 9
<212> TYPE: PRT
<213> ORGANISM: Mus musculus

<400> SEQUENCE: 272

```
His Ser Phe Lys His Glu Asp Pro Met
 1               5
```

<210> SEQ ID NO 273
<211> LENGTH: 9
<212> TYPE: PRT
<213> ORGANISM: Mus musculus

<400> SEQUENCE: 273

His Thr His Gly Val Phe Arg Gly Ile
 1               5

<210> SEQ ID NO 274
<211> LENGTH: 9
<212> TYPE: PRT
<213> ORGANISM: Mus musculus

<400> SEQUENCE: 274

Ile Leu Cys Gly Ala Gln Tyr Arg Ile
 1               5

<210> SEQ ID NO 275
<211> LENGTH: 9
<212> TYPE: PRT
<213> ORGANISM: Mus musculus

<400> SEQUENCE: 275

Lys Phe Ala Arg Ser Asp Glu Leu Val
 1               5

<210> SEQ ID NO 276
<211> LENGTH: 9
<212> TYPE: PRT
<213> ORGANISM: Mus musculus

<400> SEQUENCE: 276

Lys Arg Tyr Phe Lys Leu Ser His Leu
 1               5

<210> SEQ ID NO 277
<211> LENGTH: 9
<212> TYPE: PRT
<213> ORGANISM: Mus musculus

<400> SEQUENCE: 277

Lys Thr Ser Glu Lys Pro Phe Ser Cys
 1               5

<210> SEQ ID NO 278
<211> LENGTH: 9
<212> TYPE: PRT
<213> ORGANISM: Mus musculus

<400> SEQUENCE: 278

Leu Glu Cys Met Thr Trp Asn Gln Met
 1               5

<210> SEQ ID NO 279
<211> LENGTH: 9
<212> TYPE: PRT
<213> ORGANISM: Mus musculus

<400> SEQUENCE: 279

Leu Gly Gly Gly Gly Cys Gly Leu
 1               5

```
<210> SEQ ID NO 280
<211> LENGTH: 9
<212> TYPE: PRT
<213> ORGANISM: Mus musculus

<400> SEQUENCE: 280

Leu Gln Met His Ser Arg Lys His Thr
 1               5

<210> SEQ ID NO 281
<211> LENGTH: 9
<212> TYPE: PRT
<213> ORGANISM: Mus musculus

<400> SEQUENCE: 281

Met His Gln Arg Asn Met Thr Lys Leu
 1               5

<210> SEQ ID NO 282
<211> LENGTH: 9
<212> TYPE: PRT
<213> ORGANISM: Mus musculus

<400> SEQUENCE: 282

Asn Ala Pro Tyr Leu Pro Ser Cys Leu
 1               5

<210> SEQ ID NO 283
<211> LENGTH: 9
<212> TYPE: PRT
<213> ORGANISM: Mus musculus

<400> SEQUENCE: 283

Asn Leu Gly Ala Thr Leu Lys Gly Met
 1               5

<210> SEQ ID NO 284
<211> LENGTH: 9
<212> TYPE: PRT
<213> ORGANISM: Mus musculus

<400> SEQUENCE: 284

Asn Leu Tyr Gln Met Thr Ser Gln Leu
 1               5

<210> SEQ ID NO 285
<211> LENGTH: 9
<212> TYPE: PRT
<213> ORGANISM: Mus musculus

<400> SEQUENCE: 285

Asn Met Thr Lys Leu His Val Ala Leu
 1               5

<210> SEQ ID NO 286
<211> LENGTH: 9
<212> TYPE: PRT
<213> ORGANISM: Mus musculus

<400> SEQUENCE: 286

Asn Gln Met Asn Leu Gly Ala Thr Leu
 1               5

<210> SEQ ID NO 287
<211> LENGTH: 9
```

```
<212> TYPE: PRT
<213> ORGANISM: Mus musculus

<400> SEQUENCE: 287

Pro Gly Ala Ser Ala Tyr Gly Ser Leu
 1               5

<210> SEQ ID NO 288
<211> LENGTH: 9
<212> TYPE: PRT
<213> ORGANISM: Mus musculus

<400> SEQUENCE: 288

Gln Ala Ser Ser Gly Gln Ala Arg Met
 1               5

<210> SEQ ID NO 289
<211> LENGTH: 9
<212> TYPE: PRT
<213> ORGANISM: Mus musculus

<400> SEQUENCE: 289

Gln Met Thr Ser Gln Leu Glu Cys Met
 1               5

<210> SEQ ID NO 290
<211> LENGTH: 9
<212> TYPE: PRT
<213> ORGANISM: Mus musculus

<400> SEQUENCE: 290

Gln Gln Tyr Ser Val Pro Pro Pro Val
 1               5

<210> SEQ ID NO 291
<211> LENGTH: 9
<212> TYPE: PRT
<213> ORGANISM: Mus musculus

<400> SEQUENCE: 291

Gln Tyr Arg Ile His Thr His Gly Val
 1               5

<210> SEQ ID NO 292
<211> LENGTH: 9
<212> TYPE: PRT
<213> ORGANISM: Mus musculus

<400> SEQUENCE: 292

Gln Tyr Ser Val Pro Pro Pro Val Tyr
 1               5

<210> SEQ ID NO 293
<211> LENGTH: 9
<212> TYPE: PRT
<213> ORGANISM: Mus musculus

<400> SEQUENCE: 293

Arg Met Phe Pro Asn Ala Pro Tyr Leu
 1               5

<210> SEQ ID NO 294
<211> LENGTH: 9
<212> TYPE: PRT
<213> ORGANISM: Mus musculus
```

```
<400> SEQUENCE: 294

Arg Thr Pro Tyr Ser Ser Asp Asn Leu
  1               5

<210> SEQ ID NO 295
<211> LENGTH: 9
<212> TYPE: PRT
<213> ORGANISM: Mus musculus

<400> SEQUENCE: 295

Arg Val Ser Gly Val Ala Pro Thr Leu
  1               5

<210> SEQ ID NO 296
<211> LENGTH: 9
<212> TYPE: PRT
<213> ORGANISM: Mus musculus

<400> SEQUENCE: 296

Ser Cys Leu Glu Ser Gln Pro Thr Ile
  1               5

<210> SEQ ID NO 297
<211> LENGTH: 9
<212> TYPE: PRT
<213> ORGANISM: Mus musculus

<400> SEQUENCE: 297

Ser Cys Gln Lys Lys Phe Ala Arg Ser
  1               5

<210> SEQ ID NO 298
<211> LENGTH: 9
<212> TYPE: PRT
<213> ORGANISM: Mus musculus

<400> SEQUENCE: 298

Ser Asp Val Arg Asp Leu Asn Ala Leu
  1               5

<210> SEQ ID NO 299
<211> LENGTH: 9
<212> TYPE: PRT
<213> ORGANISM: Mus musculus

<400> SEQUENCE: 299

Ser Leu Gly Glu Gln Gln Tyr Ser Val
  1               5

<210> SEQ ID NO 300
<211> LENGTH: 9
<212> TYPE: PRT
<213> ORGANISM: Mus musculus

<400> SEQUENCE: 300

Thr Cys Gln Arg Lys Phe Ser Arg Ser
  1               5

<210> SEQ ID NO 301
<211> LENGTH: 9
<212> TYPE: PRT
<213> ORGANISM: Mus musculus

<400> SEQUENCE: 301
```

Thr Glu Gly Gln Ser Asn His Gly Ile
1               5

<210> SEQ ID NO 302
<211> LENGTH: 9
<212> TYPE: PRT
<213> ORGANISM: Mus musculus

<400> SEQUENCE: 302

Thr Leu His Phe Ser Gly Gln Phe Thr
1               5

<210> SEQ ID NO 303
<211> LENGTH: 9
<212> TYPE: PRT
<213> ORGANISM: Mus musculus

<400> SEQUENCE: 303

Thr Leu Val Arg Ser Ala Ser Glu Thr
1               5

<210> SEQ ID NO 304
<211> LENGTH: 9
<212> TYPE: PRT
<213> ORGANISM: Mus musculus

<400> SEQUENCE: 304

Val Leu Asp Phe Ala Pro Pro Gly Ala
1               5

<210> SEQ ID NO 305
<211> LENGTH: 9
<212> TYPE: PRT
<213> ORGANISM: Mus musculus

<400> SEQUENCE: 305

Trp Asn Gln Met Asn Leu Gly Ala Thr
1               5

<210> SEQ ID NO 306
<211> LENGTH: 9
<212> TYPE: PRT
<213> ORGANISM: Mus musculus

<400> SEQUENCE: 306

Tyr Phe Lys Leu Ser His Leu Gln Met
1               5

<210> SEQ ID NO 307
<211> LENGTH: 9
<212> TYPE: PRT
<213> ORGANISM: Mus musculus

<400> SEQUENCE: 307

Tyr Gln Met Thr Ser Gln Leu Glu Cys
1               5

<210> SEQ ID NO 308
<211> LENGTH: 9
<212> TYPE: PRT
<213> ORGANISM: Mus musculus

<400> SEQUENCE: 308

Tyr Ser Ser Asp Asn Leu Tyr Gln Met

```
                               1               5

<210> SEQ ID NO 309
<211> LENGTH: 6
<212> TYPE: PRT
<213> ORGANISM: Homo sapiens

<400> SEQUENCE: 309

Gly Ala Ala Gln Trp Ala
 1               5

<210> SEQ ID NO 310
<211> LENGTH: 12
<212> TYPE: PRT
<213> ORGANISM: Homo sapiens

<400> SEQUENCE: 310

Ala Ser Ala Tyr Gly Ser Leu Gly Gly Pro Ala Pro
 1               5                  10

<210> SEQ ID NO 311
<211> LENGTH: 15
<212> TYPE: PRT
<213> ORGANISM: Homo sapiens

<400> SEQUENCE: 311

Ala Phe Thr Val His Phe Ser Gly Gln Phe Thr Gly Thr Ala Gly
 1               5                  10                  15

<210> SEQ ID NO 312
<211> LENGTH: 5
<212> TYPE: PRT
<213> ORGANISM: Homo sapiens

<400> SEQUENCE: 312

His Ala Ala Gln Phe
 1               5

<210> SEQ ID NO 313
<211> LENGTH: 32
<212> TYPE: PRT
<213> ORGANISM: Homo sapiens

<400> SEQUENCE: 313

Cys His Thr Pro Thr Asp Ser Cys Thr Gly Ser Gln Ala Leu Leu Leu
 1               5                  10                  15

Arg Thr Pro Tyr Ser Ser Asp Asn Leu Tyr Gln Met Thr Ser Gln Leu
                20                  25                  30

<210> SEQ ID NO 314
<211> LENGTH: 32
<212> TYPE: PRT
<213> ORGANISM: Homo sapiens

<400> SEQUENCE: 314

Arg Ile His Thr His Gly Val Phe Arg Gly Ile Gln Asp Val Arg Arg
 1               5                  10                  15

Val Pro Gly Val Ala Pro Thr Leu Val Arg Ser Ala Ser Glu Thr Ser
                20                  25                  30

<210> SEQ ID NO 315
<211> LENGTH: 4
<212> TYPE: PRT
<213> ORGANISM: Homo sapiens
```

```
<400> SEQUENCE: 315

Arg Tyr Phe Lys
  1

<210> SEQ ID NO 316
<211> LENGTH: 14
<212> TYPE: PRT
<213> ORGANISM: Homo sapiens

<400> SEQUENCE: 316

Glu Arg Arg Phe Ser Arg Ser Asp Gln Leu Lys Arg His Gln
  1               5                  10

<210> SEQ ID NO 317
<211> LENGTH: 22
<212> TYPE: PRT
<213> ORGANISM: Homo sapiens

<400> SEQUENCE: 317

Gln Arg Lys Phe Ser Arg Ser Asp His Leu Lys Thr His Thr Arg Thr
  1               5                  10                  15

His Thr Gly Lys Thr Ser
             20

<210> SEQ ID NO 318
<211> LENGTH: 21
<212> TYPE: PRT
<213> ORGANISM: Homo sapiens

<400> SEQUENCE: 318

Cys Gln Lys Lys Phe Ala Arg Ser Asp Glu Leu Val Arg His His Asn
  1               5                  10                  15

Met His Gln Arg Asn
             20

<210> SEQ ID NO 319
<211> LENGTH: 449
<212> TYPE: PRT
<213> ORGANISM: Homo sapiens

<400> SEQUENCE: 319

Met Gly Ser Asp Val Arg Asp Leu Asn Ala Leu Leu Pro Ala Val Pro
  1               5                  10                  15

Ser Leu Gly Gly Gly Gly Gly Cys Ala Leu Pro Val Ser Gly Ala Ala
                 20                  25                  30

Gln Trp Ala Pro Val Leu Asp Phe Ala Pro Pro Gly Ala Ser Ala Tyr
             35                  40                  45

Gly Ser Leu Gly Gly Pro Ala Pro Pro Ala Pro Pro Pro Pro
         50                  55                  60

Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Ala Ile
            130                 135                 140
```

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 320
<211> LENGTH: 449
<212> TYPE: PRT
<213> ORGANISM: Mus musculus

<400> SEQUENCE: 320

Met Gly Ser Asp Val Arg Asp Leu Asn Ala Leu Leu Pro Ala Val Ser
1               5                   10                  15

Ser Leu Gly Gly Gly Gly Gly Cys Gly Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro Pro Pro
    50                  55                  60

-continued

```
Pro Pro Pro Pro His Ser Phe Ile Lys Gln Glu Pro Ser Trp Gly Gly
 65                  70                  75                  80

Ala Glu Pro His Glu Gln Cys Leu Ser Ala Phe Thr Leu His Phe
                 85                  90                  95

Ser Gly Gln Phe Thr Gly Thr Ala Gly Ala Cys Arg Tyr Gly Pro Phe
                100                 105                 110

Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Thr Ile
130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Met Ala Ala Gly Ser Ser Ser
                245                 250                 255

Ser Val Lys Trp Thr Glu Gly Gln Ser Asn His Gly Ile Gly Tyr Glu
            260                 265                 270

Ser Asp Asn His Thr Ala Pro Ile Leu Cys Gly Ala Gln Tyr Arg Ile
                275                 280                 285

His Thr His Gly Val Phe Arg Gly Ile Gln Asp Val Arg Arg Val Ser
290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp His Ser Cys Gln Lys Lys Phe Ala Arg Ser Asp Glu Leu Val
            420                 425                 430

Arg His His Asn Met His Gln Arg Asn Met Thr Lys Leu His Val Ala
                435                 440                 445

Leu
```